(12) United States Patent
Haas et al.

(10) Patent No.: US 11,899,022 B2
(45) Date of Patent: Feb. 13, 2024

(54) MULTIPLEXED PROTEOMICS AND PREDICTIVE DRUG CANDIDATE ASSESSMENT

(71) Applicant: The General Hospital Corporation, Boston, MA (US)

(72) Inventors: Wilhelm Haas, Boston, MA (US); Cyril Benes, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 680 days.

(21) Appl. No.: 16/641,365

(22) PCT Filed: Aug. 23, 2018

(86) PCT No.: PCT/US2018/047765
§ 371 (c)(1),
(2) Date: Feb. 24, 2020

(87) PCT Pub. No.: WO2019/040757
PCT Pub. Date: Feb. 28, 2019

(65) Prior Publication Data
US 2020/0225242 A1    Jul. 16, 2020

Related U.S. Application Data

(60) Provisional application No. 62/549,417, filed on Aug. 23, 2017.

(51) Int. Cl.
*G01N 33/68* (2006.01)
*G16B 5/00* (2019.01)
(Continued)

(52) U.S. Cl.
CPC ..... *G01N 33/6848* (2013.01); *G01N 33/6845* (2013.01); *G16B 5/00* (2019.02);
(Continued)

(58) Field of Classification Search
USPC .............................................. 702/19
See application file for complete search history.

(56) References Cited

U.S. PATENT DOCUMENTS

2002/0182649 A1   12/2002   Weinberger et al.
2003/0119002 A1   6/2003   Nandabalan et al.
(Continued)

OTHER PUBLICATIONS

Force, T., et al. Inhibitors of Protein Kinase Signaling Pathways Emerging Therapies for Cardiovascular Disease, Circulation, Mar. 16, 2004, 1196-1205 (Year: 2004).*
(Continued)

*Primary Examiner* — Xiaoyun R Xu
(74) *Attorney, Agent, or Firm* — Fish & Richardson P.C.

(57) ABSTRACT

The disclosure features methods of identifying specific drug candidates for disease treatment, the methods including: for pairs of associated expressed proteins in a protein-protein interaction network for a plurality of biological samples, comparing relative concentration values of the associated proteins in each of the biological samples to identify outliers among a distribution of the relative concentration values, identifying a set of proteins involved in dysregulated protein-protein interactions in the network based on the outliers, and predicting an efficacy of one or more drug candidates from among a set of drug candidates for treating a disease based on the identified set of proteins and information about one or more of proteins, protein complexes, biological pathways, and functional modules targeted by the set of drug candidates.

20 Claims, 49 Drawing Sheets

(51) Int. Cl.
  *G16B 40/10* (2019.01)
  *H01J 49/00* (2006.01)
(52) U.S. Cl.
  CPC .......... *G16B 40/10* (2019.02); *H01J 49/0036*
    (2013.01); *G01N 2560/00* (2013.01); *G01N*
    *2800/52* (2013.01)

(56) References Cited

U.S. PATENT DOCUMENTS

| | | | |
|---|---|---|---|
| 2005/0221280 | A1 | 10/2005 | Westwick et al. |
| 2011/0093204 | A1* | 4/2011 | Zucht ................. C07K 14/4711 |
| | | | 702/19 |
| 2013/0185089 | A1 | 7/2013 | Michelson et al. |
| 2016/0186266 | A1 | 6/2016 | Alarcon |
| 2017/0023577 | A1 | 1/2017 | Mulligan et al. |
| 2017/0067875 | A1 | 3/2017 | Laing et al. |
| 2017/0082634 | A1 | 3/2017 | Haas |

OTHER PUBLICATIONS

Barabasi and Albert, "Emergence of scaling in random networks," Science, Oct. 1999, 286: 509-512.
Bensimon et al., "Mass spectrometry-based proteomics and network biology," Annu Rev Biochem, Jul. 2012, 81: 379-405.
Choudhary et al., "Lysine acetylation targets protein complexes and co-regulates major cellular functions," Science, 2009, 325, 834-840.
Cox and Mann, "Quantitative, high-resolution proteomics for data-driven systems biology," Annu Rev Biochem, 2011, 80: 273-299.
Dephoure et al., "Quantitative proteomic analysis reveals post-translational responses to aneuploidy in yeast," Elife, 2014, 3: e03023.
Gry et al., "Correlations between RNA and protein expression profiles in 23 human cell lines," BMC Genomics, 2009, 10: 365.
Gunawardana et al., "Outlier detection at the transcriptome-proteome interface," Bioinformatics, 2015, 31(15):2530-2536.
Guruharsha et al., "A protein complex network of *Drosophila melanogaster*," Cell, 2011, 147: 690-703.
Gygi et al., "Correlation between protein and mRNA abundance in yeast," Mol Cell Biol, Mar. 1999, 19: 1720-1730.
Herschkowitz et al., "Identification of conserved gene expression features between murine mammary carcinoma models and human breast tumors," Genome Biol, 2007, 8: R76.
Ho et al., "Systematic identification of protein complexes in *Saccharomyces cerevisiae* by mass spectrometry," Nature, 2002, 415: 180-183.
Huang et al., "Systematic and integrative analysis of large gene lists using DAVID bioinformatics resources," Nat Protoc., 2009, 4: 44-57.
Huttlin et al., "A tissue-specific atlas of mouse protein phosphorylation and expression," Cell, 2010, 143: 1174-1189.
Kim et al., "Systematic and quantitative assessment of the ubiquitin-modified proteome," Mol Cell, 2011, 44: 325-340.
Klijn et al., "A comprehensive transcriptional portrait of human cancer cell lines," Nat Biotechnol, Mar. 2015, 33: 306-312.
Kramer et al., "Photo-cross-linking and high-resolution mass spectrometry for assignment of RNA-binding sites in RNA-binding proteins," Nat Methods, 2014, 11: 1064-1070.
Lundberg et al., "Defining the transcriptome and proteome in three functionally different human cell lines," Mol Syst Biol, 2010, 6:450.
McAlister et al., "MultiNotch MS3 enables accurate, sensitive, and multiplexed detection of differential expression across cancer cell line proteomes," Anal Chem, 2014, 86:7150-7158.
Neve et al., "A collection of breast cancer cell lines for the study of functionally distinct cancer subtypes," Cancer Cell, 2006, 10:515-527.
Ong et al., "Identifying the proteins to which small-molecule probes and drugs bind in cells," PNAS, Mar. 2009, 106:4617-4622.
Ross et al., "Multiplexed protein quantitation in *Saccharomyces cerevisiae* using amine-reactive isobaric tagging reagents," Mol Cell Proteomics, 2004, 3:1154-1169.
Ruepp et al., "CORUM: the comprehensive resource of mammalian protein complexes—2009," Nucleic Acids Res, 2010, 38:D497-501.
Sharma et al., "Ultradeep human phosphoproteome reveals a distinct regulatory nature of Tyr and Ser/Thr-based signaling." Cell Rep, 2014, 8:1583-1594.
Sotiriou et al., "Breast cancer classification and prognosis based on gene expression profiles from a population-based study," PNAS, Sep. 2003, 100:10393-10398.
Stingele et al., "Global analysis of genome, transcriptome and proteome reveals the response to aneuploidy in human cells," Mol Syst Biol, 2012, 8:608.
Szklarczyk et al., "The STRING database in 2011: functional interaction networks of proteins, globally integrated and scored," Nucleic Acids Res, 2011, 39:D561-568.
Ting et al., "MS3 eliminates ratio distortion in isobaric multiplexed quantitative proteomics," Nat Methods, 2011, 8:937-940.
Wu et al., "Multilayered genetic and omics dissection of mitochondrial activity in a mouse reference population," Cell, 2014, 158:1415-1430.
Zhang et al., "Proteogenomic characterization of human colon and rectal cancer," Nature, 2014, 513:382-387.
Benjamini et al., "Controlling the false discovery rate: a practical and powerful approach to multiple testing," J. R. Statist. Soc. Jan. 1995, 57(1):289-300.
Elias et al., "Target-decoy search strategy for increased confidence in large-scale protein identifications by mass spectrometry," Nat. Methods, Mar. 2007, 4(3):207-214.
Horn et al., "KinomeXplorer: an integrated platform for kinome biology studies," Nature Methods, Jun. 2014, 11(6):603-604.
Hu et al., "The Orbitrap: a new mass spectrometer," J. Mass Spectrom., Apr. 2005, 40(4):430-443.
Huang et al., "Bioinformatics enrichment tools: paths toward the comprehensive functional analysis of large gene lists," Nucleic Acids Res., Jan. 2009, 37(1):1-13.
Marcotte et al., "Essential gene profiles in breast, pancreatic, and ovarian cancer cells," Cancer Discov., Feb. 2012, 2(2):172-189.
Marcotte et al., "Functional Genomic Landscape of Human Breast Cancer Drivers, Vulnerabilities, and Resistance," Cell , Jan. 2016, 164(1-2):293-309.
McAlister et al., "Increasing the multiplexing capacity of TMTs using reporter ion isotopologues with isobaric masses," Analytical Chemistry, Sep. 2012, 84(17):7469-7478.
PCT International Preliminary Report on Patentability in International Appln. No. PCT/US2018/047765, dated Feb. 25, 2020, 10 pages.
PCT International Search Report and Written Opinion in International Appln. No. PCT/US2018/047765, dated Oct. 19, 2018, 15 pages.
Perry et al., "Orbitrap mass spectrometry: instrumentation, ion motion and applications," Mass Spectrom. Rev. Nov. 2008, 27(6):661-699.
Riley et al., "Phosphoproteomics in the Age of Rapid and Deep Proteome Profiling," Analytical Chemistry, Jan. 2016, 88(1):74-94.
Sadygov et al., "Large-scale database searching using tandem mass spectra: looking up the answer in the back of the book," Nat. Methods, Dec. 2004, 1(3):195-202.
Thompson et al., "Tandem mass tags: a novel quantification strategy for comparative analysis of complex protein mixtures by MS/MS," Analytical Chemistry, Apr. 2003, 75(8):1895-1904.
Lamerz et al., "Correlation-associated peptide networks of human cerebrospinal fluid," Proteomics, Jul. 2005, 5(11):2789-98.
Schrader et al., "Historical perspective of peptidomics," EuPA Open Proteomics, Jun. 2014, 3:171-182.

* cited by examiner

FIG. 6A
FIG. 6B
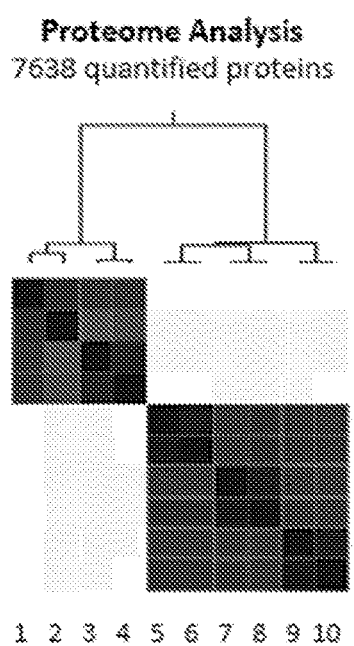
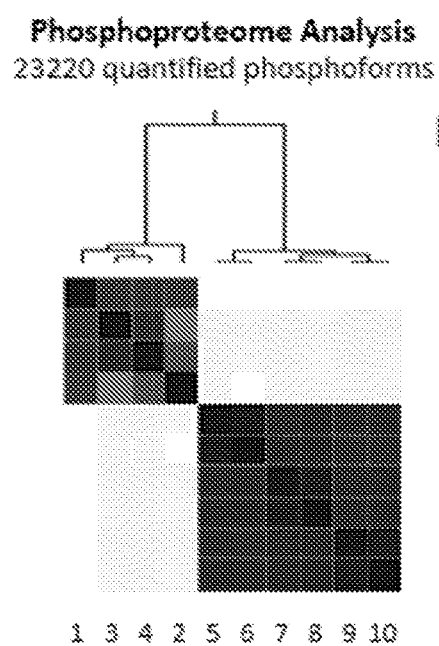
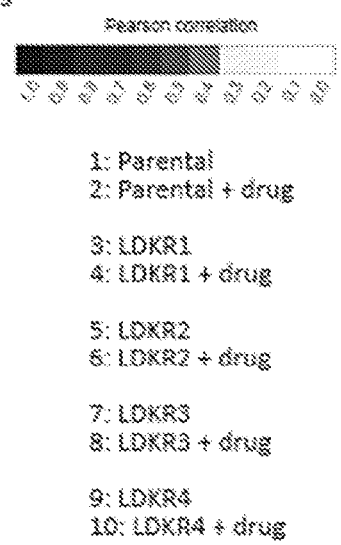

FIG. 7A
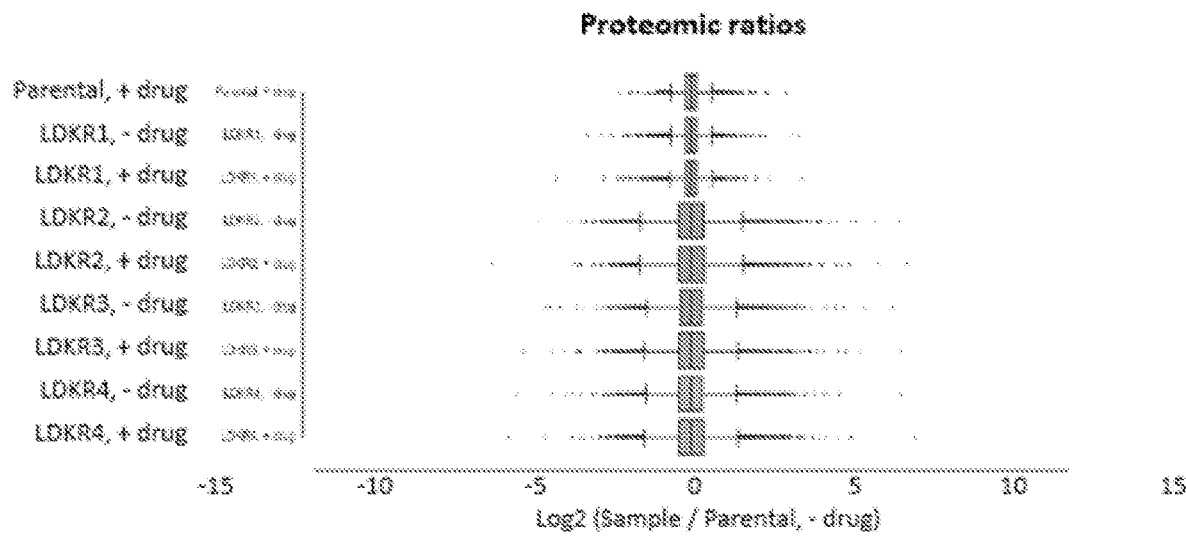
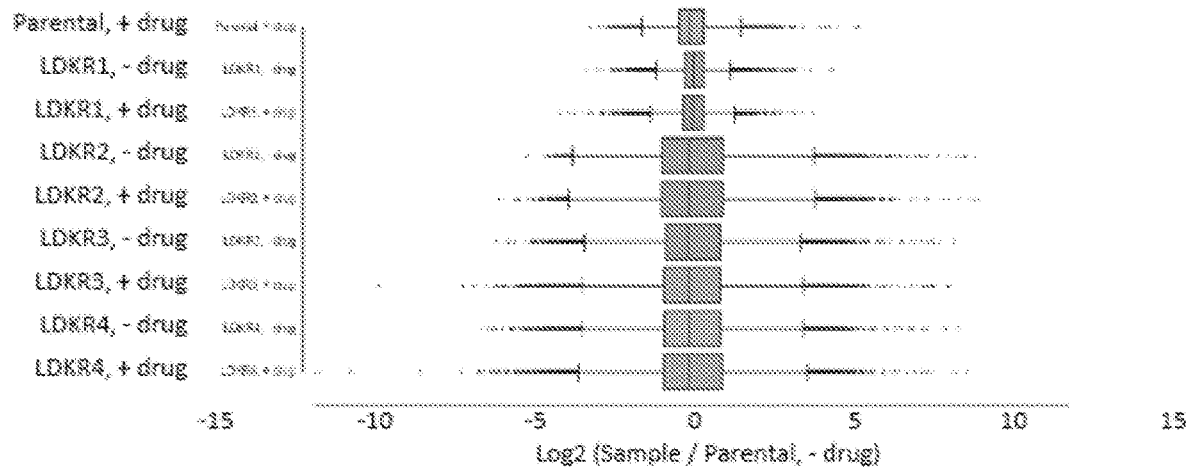
FIG. 7B

Protein profiles
RNA profiles

14336_Protein    14336_RNA

MULTIPLEXED PROTEOMICS AND PREDICTIVE DRUG CANDIDATE ASSESSMENT

CROSS-REFERENCE TO RELATED APPLICATIONS

This application is a § 371 National Stage Application of PCT/US2018/047765, filed Aug. 23, 2018, which claims priority to U.S. Provisional Patent Application No. 62/549,417, filed on Aug. 23, 2017, the entire contents of which are incorporated herein by reference.

TECHNICAL FIELD

This disclosure relates to methods and systems for proteomic and phosphoproteomic analysis of biological samples, and predictive assessment of drug candidates.

BACKGROUND

The interactions of a protein reveal its functional network in a cell. The interactome—a comprehensive mapping of all protein-protein interactions in a cell and the dynamics thereof—has the potential to offer unique insights into biological systems and their reactions to perturbations. Research efforts are underway to generate global protein-protein interaction maps by using the yeast-two hybrid (Y2H) assay or protein affinity-purification/mass spectrometry (AP-MS). However, generating a static interaction catalogue of a comprehensive protein-protein interaction network represents a significant challenge. Moreover, robust methods for studying protein-protein co-regulation dynamics after perturbation have not been well developed.

SUMMARY

Studies performed using conventional high-throughput analysis techniques such as mass spectrometry have provided valuable new information concerning the wide variety of phosphorylated proteins and phosphosites in eukaryotic cells. However, while these studies comprise some of the most extensive datasets to date, they still only represent a small fraction of the estimated phosphoproteome.

This methods and systems disclosed herein provide improved mass spectrometry-based quantitative detection of phosphopeptides. The methods feature dual fragmentation schemes to identify phosphopeptides, which are then fragmented further for quantification. By using dual fragmentation schemes, a larger number of phosphopeptides can be identified than would otherwise be possible using only a single scheme, which allows for quantitative measurement of a larger number of phosphorylated species. Information about phosphorylated proteins and phosphosites can then be used to evaluate a variety of cellular responses including, for example, responses to agents such as kinase inhibitors, as discussed further below.

The disclosure features methods of identifying protein-protein deregulation, the methods including: generating a basal protein-protein interaction network for a plurality of biological samples, the network featuring a set of proteins expressed in the biological samples and concentrations of each member of the set of expressed proteins in each of the biological samples; identifying two associated expressed proteins in the network; for the two associated expressed proteins, comparing correlated relative concentration values of the two proteins in each of the biological samples to identify outliers among a distribution of the relative concentration values; and identifying members of the plurality of biological samples in which deregulation of the two associated expressed proteins occurs based on the outliers.

The methods can include any one or more of the following features.

Generating the basal protein-protein interaction network can include identifying the proteins expressed in the biological samples and measuring the concentrations of each member of the set of expressed proteins by performing mass spectral analysis of each of the biological samples. The methods can include identifying the two associated expressed proteins in the network by calculating a Spearman's correlation coefficient for concentration distributions of each of the two expressed proteins in the plurality of biological samples, and determining whether the two expressed proteins are associated based on a value of the calculated Spearman's correlation coefficient. The methods can include identifying the two expressed proteins as associated if the value of the Spearman's correlation coefficient exceeds a threshold value.

Comparing correlated relative concentration values of the two proteins in each of the biological samples to identify outliers among a distribution of the correlated relative concentration values can include identifying as outliers correlated relative concentration values that are positioned at greater than a threshold distance from a set of correlated relative concentration values that defines the distribution. Comparing correlated relative concentration values of the two proteins in each of the biological samples to identify outliers among a distribution of the correlated relative concentration values can include: determining a line of best fit representing the distribution of the correlated relative concentration values; and for each member of the distribution of the correlated relative concentration values, calculating a shortest distance from the member to the line of best fit, and designating the member as an outlier if the shortest distance associated with the member exceeds a threshold distance value. Identifying members of the plurality of biological samples in which deregulation of the two associated expressed proteins occurs based on the outliers can include, for each member of the distribution of the correlated relative concentration values designated as an outlier, determining a sample from among the plurality of biological samples that is associated with the outlier.

The plurality of biological samples can include a plurality of cancer cell lines.

Performing mass spectral analysis of each of the biological samples can include ionizing peptides derived from the biological samples to generate peptide ions, fragmenting a first portion of the peptide ions by collision-induced dissociation to generate a first population of peptide ion fragments, fragmenting a second portion of the peptide ions by high-energy collision dissociation to generate a second population of peptide ion fragments, analyzing the first population of peptide ion fragments by trapping the first population of peptide ion fragments in a linear ion trap to identify a first population of peptides corresponding to the first population of peptide ion fragments, analyzing the second population of peptide ion fragments in an orbital trap to identify a second population of peptides corresponding to the second population of peptide ion fragments, and identifying a set of proteins expressed in the biological sample based on the first and second populations of peptides.

Embodiments of the methods can also include any of the other features disclosed herein, including features disclosed in connection with different embodiments, in any combination unless expressly stated otherwise.

In another aspect, the disclosure features methods of measuring phosphorylated peptides in a biological sample, the methods including ionizing phosphorylated peptides derived from a biological sample to generate peptide ions, fragmenting a first portion of the peptide ions by collision-induced dissociation to generate a first population of peptide ion fragments, fragmenting a second portion of the peptide ions by high-energy collision dissociation to generate a second population of peptide ion fragments, analyzing the first population of peptide ion fragments by trapping the first population of peptide ion fragments in a linear ion trap to identify a first population of peptides corresponding to the first population of peptide ion fragments, analyzing the second population of peptide ion fragments in an orbital trap to identify a second population of peptides corresponding to the second population of peptide ion fragments, and identifying a set of phosphorylated peptides in the biological sample based on the first and second populations of peptides.

Embodiments of the methods can include any one or more of the following features.

The first and second portions of the peptide ions can be fragmented in parallel within a mass spectrometry system. The methods can include further fragmenting a portion of the first population of peptide ion fragments by high-energy collision dissociation to generate a third population of peptide ion fragments, and analyzing the third population of peptide ion fragments in the orbital trap to determine quantities of at least some members of the set of peptides in the biological sample.

The methods can include extracting the phosphorylated peptides from the biological sample, functionalizing the extracted phosphorylated peptides with at least one tandem mass tag, where the at least one tandem mass tag features a chemical moiety that dissociates from the phosphorylated peptide during high-energy collision dissociation, detecting ion signals corresponding to at least one chemical moiety dissociated from the phosphorylated peptides, and determining the quantities of the at least some members of the set of peptides based on the ion signals. The methods can include selecting a subset of the first population of peptide ion fragments for further fragmentation to generate the third population of peptide ion fragments.

The methods can include grouping the members of the set of phosphorylated peptides into a plurality of groups based on the activity of the phosphorylated peptides in the sample, and, for each one of the groups: identifying peptides that exhibit phosphorylation on a kinase; identifying locations of phosphorylation events corresponding to the identified peptides; and determining whether the locations of the phosphorylation events are within an activation loop for the kinase. The methods can include identifying the kinase as a member of a kinome activity profile for the group.

The methods can include, for each one of the groups: identifying a set of phosphosites corresponding to the group, where the set of phosphosites includes locations of all phosphorylation events on members of the group; evaluating a metric relating to localization of phosphorylation at each of the locations; and identifying a subset of the set of phosphosites for which the metric exceeds a threshold value. The methods can include, for each member of the subset of phosphosites, determining a most likely phosphorylating kinase associated with the member. The methods can include identifying the most likely phosphorylating kinase as a member of the kinome activity profile for the group.

Analyzing the first population of peptide ion fragments to identify a first population of peptides can include measuring mass spectral information corresponding to the first population of peptide ion fragments, the mass spectral information featuring information about mass-to-charge ratios of the first population of peptide ion fragments, and comparing the information about mass-to-charge ratios of the first population of peptide ion fragments to reference information for peptide fragments to identify parent peptides corresponding to the first population of peptide ion fragments.

Embodiments of the methods can also include any of the other features disclosed herein, including features disclosed in connection with different embodiments, in any combination unless expressly stated otherwise.

In a further aspect, the disclosure features methods of identifying specific drug candidates for disease treatment, the methods including: generating a protein-protein interaction network for a plurality of biological samples, the network featuring a set of proteins expressed in the biological samples and concentrations of each member of the set of expressed proteins in each of the biological samples; for pairs of associated expressed proteins in the network, comparing relative concentration values of the associated proteins in each of the biological samples to identify outliers among a distribution of the relative concentration values; identifying a set of dysregulated proteins in the network based on the outliers; and predicting an efficacy of one or more drug candidates from among a set of drug candidates for treating a disease based on the identified set of dysregulated proteins and information about proteins targeted by members of the set of drug candidates.

Embodiments of the methods can include any one or more of the following features.

Predicting the efficacy of the one or more drug candidates can include determining, for each drug candidate among the set of drug candidates, whether the drug candidate targets at least one of the identified dysregulated proteins.

The plurality of biological samples can include a set of cancer cell lines. The plurality of biological samples can include a set of breast cancer cell lines.

Identifying the set of dysregulated proteins can include determining, for each dysregulated protein, whether the protein is dysregulated in all of the biological samples. The biological samples can include basal and luminal cell lines, and the set of dysregulated proteins can include proteins that are dysregulated in only one of the basal and luminal cell lines.

Generating the protein-protein interaction network can include identifying the proteins expressed in the biological samples and measuring the concentrations of each member of the set of expressed proteins by performing mass spectral analysis of each of the biological samples.

The methods can include determining whether pairs of expressed proteins in the network are associated by: calculating a Spearman's correlation coefficient for concentration distributions of each of the expressed proteins in the plurality of biological samples; and determining whether pairs of expressed proteins are associated based on a value of the calculated Spearman's correlation coefficient. The methods can include identifying a pair of expressed proteins as associated if the value of the Spearman's correlation coefficient exceeds a threshold value.

Comparing relative concentration values of the associated proteins in each of the biological samples to identify outliers among the distribution of the relative concentration values can include identifying as outliers correlated relative concentration values that are positioned at greater than a threshold distance from a set of correlated relative concentration values that defines the distribution.

Comparing correlated relative concentration values of the associated proteins in each of the biological samples to identify outliers among the distribution of the relative concentration values can include determining a line of best fit representing the distribution of the relative concentration values, and for each member of the distribution of the relative concentration values, calculating a shortest distance from the member to the line of best fit and designating the member as an outlier if the shortest distance associated with the member exceeds a threshold distance value. Identifying the set of dysregulated proteins in the network based on the outliers can include, for each member of the distribution of the relative concentration values designated as an outlier, determining a sample from among the plurality of biological samples that is associated with the outlier.

Performing mass spectral analysis of each of the biological samples can include: ionizing peptides derived from the biological samples to generate peptide ions; fragmenting a first portion of the peptide ions by collision-induced dissociation to generate a first population of peptide ion fragments; fragmenting a second portion of the peptide ions by high-energy collision dissociation in an orbital trap to generate a second population of peptide ion fragments; analyzing the first population of peptide ion fragments by trapping the first population of peptide ion fragments in a linear ion trap to identify a first population of peptides corresponding to the first population of peptide ion fragments; analyzing the second population of peptide ion fragments in an orbital trap to identify a second population of peptides corresponding to the second population of peptide ion fragments; and identifying a set of proteins expressed in the biological sample based on the first and second populations of peptides.

Embodiments of the methods can also include any of the other features disclosed herein, including features disclosed in connection with different embodiments, in any combination unless expressly stated otherwise.

In another aspect, the disclosure features methods of identifying specific drug candidates for disease treatment that include, for pairs of associated expressed proteins in a protein-protein interaction network for a plurality of biological samples, comparing relative concentration values of the associated proteins in each of the biological samples to identify outliers among a distribution of the relative concentration values, identifying a set of proteins involved in dysregulated protein-protein interactions in the network based on the outliers, and predicting an efficacy of one or more drug candidates from among a set of drug candidates for treating a disease based on the identified set of proteins and information about one or more of proteins, protein complexes, biological pathways, and functional modules targeted by the set of drug candidates.

Embodiments of the methods can include any one or more of the following features.

The methods can include generating the protein-protein interaction network from the plurality of biological samples, where the network includes a set of proteins expressed in the biological samples and concentrations of each member of the set of expressed proteins in each of the biological samples.

Predicting the efficacy of the one or more drug candidates can include determining, for each drug candidate among the set of drug candidates, whether the drug candidate targets at least one of the proteins involved in dysregulated protein-protein interactions. Predicting the efficacy of the one or more drug candidates can include determining, for each drug candidate among the set of drug candidates, whether the drug candidate targets at least one protein complex in which at least one of the proteins involved in dysregulated protein-protein interactions is embedded. Predicting the efficacy of the one or more drug candidates can include determining, for each drug candidate among the set of drug candidates, whether the drug candidate targets at least one biological pathway involving at least one of the proteins involved in dysregulated protein-protein interactions. Predicting the efficacy of the one or more drug candidates can include determining, for each drug candidate among the set of drug candidates, whether the drug candidate targets at least one functional module involving at least one of the proteins involved in dysregulated protein-protein interactions.

The plurality of biological samples can include a set of cancer cell lines (e.g., a set of breast cancer cell lines).

Identifying the set of proteins involved in dysregulated protein-protein interactions can include determining, for each protein, whether the protein is involved in dysregulated protein-protein interactions in all of the biological samples. The biological samples can include basal and luminal cell lines, and the set of proteins involved in dysregulated protein-protein interactions can include proteins that are involved in dysregulated protein-protein interactions in only one of the basal and luminal cell lines.

Generating the protein-protein interaction network can include identifying the proteins expressed in the biological samples and measuring the concentrations of each member of the set of expressed proteins by performing mass spectral analysis of each of the biological samples.

The methods can include determining whether pairs of expressed proteins in the network are associated by calculating a Spearman's correlation coefficient for concentration distributions of each of the expressed proteins in the plurality of biological samples, and determining whether pairs of expressed proteins are associated based on a value of the calculated Spearman's correlation coefficient. The methods can include identifying a pair of expressed proteins as associated if the value of the Spearman's correlation coefficient exceeds a threshold value.

The methods can include determining whether pairs of expressed proteins in the network are associated by calculating a Pearson correlation coefficient for concentration distributions of each of the expressed proteins in the plurality of biological samples, and determining whether pairs of expressed proteins are associated based on a value of the calculated Pearson correlation coefficient.

Comparing relative concentration values of the associated proteins in each of the biological samples to identify outliers among the distribution of the relative concentration values can include identifying as outliers correlated relative concentration values that are positioned at greater than a threshold distance from a set of correlated relative concentration values that defines the distribution. The distribution can include a reference relative concentration value that represents the distribution, and the methods can include, for each member of the distribution of the relative concentration values, determining a Mahalanobis distance between the correlated relative concentration value associated with the member and the reference relative concentration value, and designating the member as an outlier if the distance exceeds a threshold distance value.

Comparing correlated relative concentration values of the associated proteins in each of the biological samples to identify outliers among the distribution of the relative concentration values can include determining a line of best fit representing the distribution of the relative concentration values, and for each member of the distribution of the relative concentration values, calculating a shortest distance from the member to the line of best fit, and designating the member as an outlier if the shortest distance associated with the member exceeds a threshold distance value.

Identifying the set of proteins involved in dysregulated protein-protein interactions in the network based on the outliers can include, for each member of the distribution of the relative concentration values designated as an outlier, determining a sample from among the plurality of biological samples that is associated with the outlier.

Performing mass spectral analysis of each of the biological samples can include ionizing peptides derived from the biological samples to generate peptide ions, fragmenting a first portion of the peptide ions by collision-induced dissociation to generate a first population of peptide ion fragments, fragmenting a second portion of the peptide ions by high-energy collision dissociation in an orbital trap to generate a second population of peptide ion fragments, analyzing the first population of peptide ion fragments by trapping the first population of peptide ion fragments in a linear ion trap to identify a first population of peptides corresponding to the first population of peptide ion fragments, analyzing the second population of peptide ion fragments in an orbital trap to identify a second population of peptides corresponding to the second population of peptide ion fragments, and identifying a set of proteins expressed in the biological sample based on the first and second populations of peptides.

Embodiments of the methods can also include any of the other features disclosed herein, including any combination of features disclosed in connection with different embodiments, except as expressly stated otherwise.

In a further aspect, the disclosure features a computer program product tangibly embodying a set of instructions that, when executed by a processor, causes the processor to identify specific drug candidates for disease treatment by, for pairs of associated expressed proteins in a protein-protein interaction network for a plurality of biological samples, comparing relative concentration values of the associated proteins in each of the biological samples to identify outliers among a distribution of the relative concentration values, identifying a set of proteins involved in dysregulated protein-protein interactions in the network based on the outliers, and predicting an efficacy of one or more drug candidates from among a set of drug candidates for treating a disease based on the identified set of proteins and information about one or more of proteins, protein complexes, biological pathways, and functional modules targeted by the set of drug candidates.

Embodiments of the computer program product can include any of the features disclosed herein, including any combination of features disclosed in connection with different embodiments, except as expressly stated otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIGS. 6A and 6B are schematic diagrams showing quantified proteins and phosphoforms following proteome analysis and phosphoproteome analysis, respectively, of five cell lines.

FIGS. 7A and 7B are schematic diagrams showing proteomic and phosphoproteomic ratios, respectively, for the five cell lines of FIGS. 6A and 6B.

Like reference symbols in the various drawings indicate like elements.

DETAILED DESCRIPTION

Multiplexed Proteomics

The vast number of predicted phosphorylated species in the eukaryotic proteome has encouraged the development of high-throughput techniques for identification and examination of phosphosites. Among these techniques, mass spectrometry (MS) has emerged as a useful tool for phosphoproteomic studies. MS-based phosphoproteomics can be roughly divided into two classes: "shotgun" methods for unbiased discovery of phosphospecies, and more biased selected reaction monitoring (SRM) for analysis of known, chosen phosphopeptides. In almost all cases, the relative sparsity of phosphopeptides (approximately 1% of the peptides in a cell) requires enrichment prior to analysis. Enrichment and fractionation strategies include metal affinity beads, strong cation exchange or hydrophilic interaction chromatography, phosphoantibodies, and chemical derivitization and targeted capture. These approaches have markedly improved detection of phosphopeptides derived from the cellular phosphoproteome.

Large-scale MS-based phosphoproteomic studies have been performed on eukaryotic yeast, mouse, and human cells. Starting from 10-25 mg of peptide, these studies have identified anywhere from 10,000-36,000 phosphosites, with the largest number coming from the analysis of mouse tissues.

However, existing MS-based techniques have been able to identify only a small fraction of the estimated phosphoproteome. To further progress in the understanding of this critical cellular system, improvements in MS-based phosphopeptide identification techniques are needed.

Conventional phosphoproteomic methodologies vary according to the peptides that are studied. For example, methodologies can involve highly targeted approaches with spiked synthetic peptides for quantification, or bottom-up shotgun phosphoproteomics.

Figure 1A:
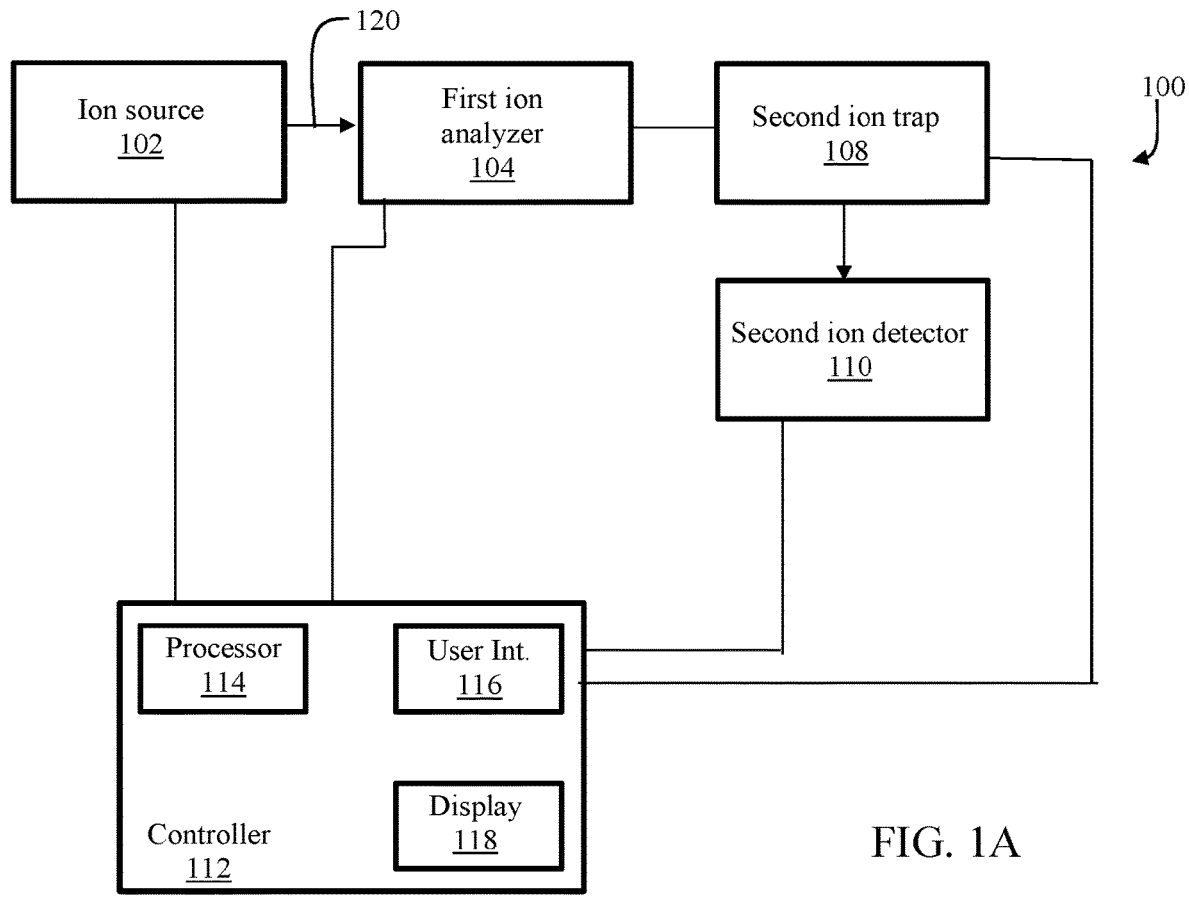
FIG. 1A is a schematic diagram of a mass spectrometry system.

FIG. 1A is a schematic diagram of an example of a mass spectrometry system 100. The system includes an ion source 102, a first ion analyzer 104, a second ion trap 108, and a second ion detector 110. Each of these components is connected to a controller 112 via electronic communication lines. Controller 112 includes an electronic processor 114, a user interface 116, and a display unit 118.

In general, the ion source, ion analyzer, ion trap, and ion detector can be implemented using a variety of different technologies and techniques. For example, suitable ion sources that can be used as ion source 102 include electrospray ionization (ESI) sources and matrix-assisted laser desorption/ionization (MALDI) sources.

First ion analyzer 104 is typically implemented as an orbital trap-based analyzer and detector. An orbital trap (i.e., "orbitrap") system generally includes a linear C-trap into which ions or ion fragments are introduced for analysis. Fragmentation of the ions (or further fragmentation of the ion fragments) occurs within the C-trap. The ion fragments are then introduced into the orbitrap, which features an outer electrode having a barrel-like shape, and an inner coaxial, spindle-shaped electrode. The ion fragments circulate in an orbital motion around the inner electrode of the orbitrap, generating an image current. The image current is detected, and converted to mass spectral information by performing a frequency analysis of the current.

Figure 1B:
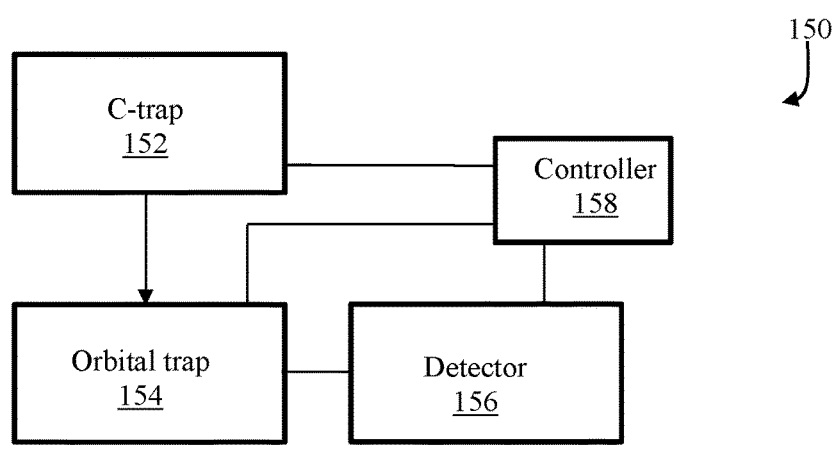
FIG. 1B is a schematic diagram of an orbital trap-based ion analyzer.

FIG. 1B is a schematic diagram of an Orbitrap-based ion analyzer 150 which includes a C-trap 152, an orbital trap 154, a detector 156, and a controller 158 connected to the other components of the analyzer. Detector 156 measures currents due to the ion fragments in orbital trap 154. Controller 158, which can correspond to controller 112 in FIG. 1A or can be a separate controller, is configured to apply electrical potentials to the electrodes of C-trap 152 and orbital trap 154, and to receive measurement information from detector 156.

It should be noted that, while not shown directly in FIG. 1B, in some embodiments C-trap 152 can be connected to both orbital trap 154 and to second ion trap 108. Ions or ion fragments introduced into C-trap 152 can be fragmented therein, and then directed to either or both of orbital trap 154 and second ion trap 108. Accordingly, it should be understood that the fragmentation steps disclosed herein can be performed in C-trap 152, with the resulting ion fragments directed to suitable analyzers and ion traps according to the implemented analytical methods.

Orbitrap systems and methods for detecting ions using such systems are disclosed, for example, in Hu et al., "The Orbitrap: a new mass spectrometer," *J. Mass Spectrom.* 40(4): 430-443 (2005), and Perry et al., "Orbitrap mass spectrometry: instrumentation, ion motion and applications," *Mass Spectrom. Rev.* 27(6): 661-699 (2008), the entire contents of each of which are incorporated herein by reference. As an example, first ion analyzer 104 can correspond to the Orbitrap Fusion™ or Orbitrap Lumos™ mass spectrometry systems (available from ThermoFisher Scientific, Waltham, MA).

Suitable ion traps for implementation as second ion trap 108 include, but are not limited to, linear quadrupole and/or higher multipole-based traps. Suitable detectors for implementation as second ion detector 110 include hemispherical analyzers based on magnetic and/or electric fields, Faraday cup-based detectors, electron multipliers, current and/or voltage detectors, and combinations of these and other well-known detectors.

Returning to FIG. 1A, during operation of system 100, a sample to be analyzed is introduced into ion source 102. Ion source 102 ionizes particles of the sample, generating ions 120. Ions 120 can then be analyzed by first ion analyzer 104, and/or trapped and analyzed by second ion trap 108 and detector 110. As will be explained in greater detail below, in some embodiments, ions 120 can undergo (further) fragmentation in first ion analyzer 104 and/or second ion trap 108.

An example of a conventional method for MS-based analysis of phosphopeptides is as follows. First, digested peptides are isobarically-labeled, and then introduced into an ion source, where the labeled peptides are ionized. The ions are trapped within an ion analyzer, and a preliminary detection of the trapped ions is performed (a "MS1" scan) to detect peptide ions.

The peptides are then further fragmented in a process such as collision-induced dissociation (CID) or electron transfer dissociation (ETD), and peptide identification occurs by trapping the peptide fragments (typically in a linear ion trap), performing a second scan (a "MS2" scan), and analyzing the charge-to-mass ratios of the fragments to identify fragment patterns characteristic of specific peptides. Next, the identified peptides are quantitatively measured, by first fragmenting the peptides (typically using a technique such as high-energy collision dissociation (HCD), trapping the fragments (typically in an orbitrap-based analyzer), and then performing a third scan (a "MS3" scan) to compare ratios of labeled and unlabeled peptide fragments to determine peptide concentration levels.

In the present disclosure, phosphopeptide identification during the second scan (i.e., at the MS2 level of analysis) is modified to improve the detection of phosphopeptides, and to improve the accuracy of their quantification. In particular, precursor ions are fragmented in parallel using different ionization methodologies to increase the number of peptides that are identified. Isobaric chemical tags are used to multiplex the phosphopeptide analysis, increasing throughput while maintaining high accuracy during identification.

Figure 2:
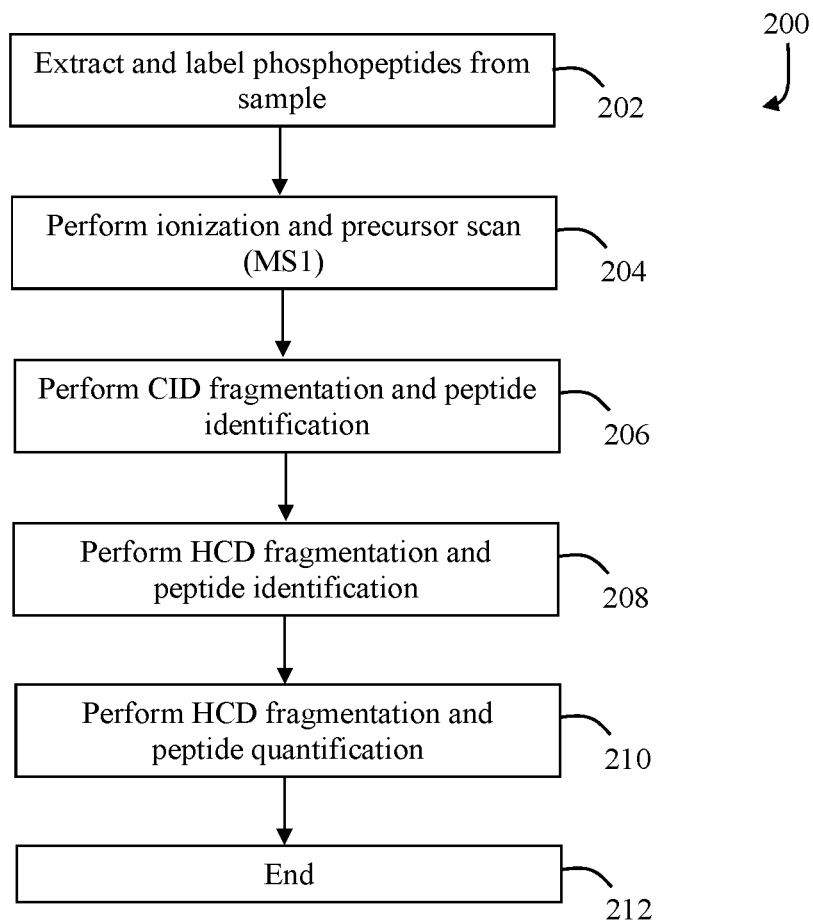
FIG. 2 is a flow chart showing a series of steps for identifying and quantifying phosphorylated proteins derived from a sample.

FIG. 2 is a flow chart 200 showing a series of steps for identifying and quantifying phosphorylated proteins derived from a sample. In the first step 202, phosphorylated peptides are isolated and labeled for analysis. Proteins are extracted from a sample and digested yielding peptides, some of which are phosphorylated. The phosphorylated peptides are typically enriched using titanium oxide beads and a phosphotyrosine antibody. The enriched peptides are then labeled with 10-plex tandem mass tag (TMT) reagents. Methods for labeling peptides using TMT reagents are disclosed, for example, in Thompson et al., "Tandem mass tags: a novel quantification strategy for comparative analysis of complex protein mixtures by MS/MS," *Analytical Chemistry* 75: 1895-1904 (2003), the entire contents of which are incorporated by reference herein.

After labeling, in step 204, the phosphopeptides are introduced into a mass spectrometry system (e.g., system 100) and ionized to generate precursor ions. The precursor ions typically correspond to molecular ion species of the parent peptides and peptide fragment ions that do not fragment extensively.

Following injection of the labeled phosphopeptides, the peptides are ionized by one or more of a variety of methodologies (e.g., electrospray ionization, MALDI) implemented by ion source 102, and the resulting precursor ions are trapped within first ion analyzer 104, an orbitrap-based analyzer. As discussed above, mass spectral information for the trapped precursor ions (i.e., mass-to-charge ratios, m/z) is obtained by detecting image currents generated by the ions within the orbitrap and performing a Fourier transform analysis of the signals. All ions are typically measured in parallel, and the first set of mass spectral information thus obtained includes m/z information for the precursor ions.

The first set of information is used to configure first and second ion detectors 106 and 110, and to adjust parameters of first analyzer 104 and second ion trap 108, to prepare system 100 for peptide identification. Then, steps 206 and 208 are performed in parallel to identify labeled phosphopeptides. In step 206, a portion of the precursor ions generated in step 204 are further fragmented using a collision-induced dissociation (CID) methodology to generate a population of peptide fragment ions, which are trapped in second ion trap 108. As an example, the precursor ions can be accelerated to a relatively high kinetic energy and then exposed to neutral molecules of an inert gas such as helium, nitrogen, or argon. Collisions between the precursor ions and neutral molecules lead to the conversion of kinetic energy into internal energy within the precursor ions, causing complex patterns of fragmentation.

The CID methodology is performed within second ion trap 108, which is generally implemented as a linear ion trap with a quadrupole or higher multipole electrode geometry. The peptide fragment ions trapped within second ion trap 108 are then detected by second ion detector 110, which measures m/z ratios of the fragments, yielding a second set of information that is communicated to controller 112.

In step 208, a portion of the precursor ions generated in step 204 are fragmented using a high-energy collision dissociation (HCD) methodology, generating another population of peptide fragment ions. HCD methodologies are specific to orbitrap ion traps. Precursor ions are introduced into a multipole HCD cell (i.e., C-trap 152 in FIG. 1B) where acceleration and fragmentation occurs due to induced collisions. Within the HCD cell, precursor ions are typically accelerated to energies of less than about 100 eV to cause fragmentation via dissociation. After a population of ionized fragments is generated within the HCD cell, the fragments are injected into orbital trap 154 for analysis. Orbital trap 154 and detector 156 measure image current information for the fragments, which is then converted to a third set of m/z information for the fragments (e.g., by controller 112).

In general, HCD-based fragmentation can be performed at higher energy than CID-based fragmentation. Further, in HCD-based methodologies, multiple collisions between fragments are possible so that further fragmentation can occur. In contrast, in CID-based fragmentation, only one fragmentation is typically possible before ion fragments fall out of the excitation window.

The second and third sets of mass spectral information acquired in steps 206 and 208 can be used by controller 112 to identify phosphopeptides derived from the sample. For example, in some embodiments, the information about m/z ratios can be compared against mass spectral information contained in spectral libraries for known peptides to identify the peptides. Typically, this process involves matching measured signals at multiple m/z values, corresponding to fragmentation patterns for specific peptides, to known fragmentation patterns. In general, a wide variety of different methods can be used to analyze the acquired mass spectral information for purposes of peptide identification. Suitable methods are disclosed, for example, in the following references, the entire contents of each of which are incorporated herein by reference: Sadygov et al., "Large-scale database searching using tandem mass spectra: looking up the answer in the back of the book," *Nat. Methods* 1(3): 195-202 (2004); and Riley et al., "Phosphoproteomics in the Age of Rapid and Deep Proteome Profiling," *Analytical Chemistry* 88(1): 74-94 (2016).

In the next step 210, specific peptides identified following steps 206 and 208 are quantitatively analyzed to determine the amounts of these peptides in the sample. In general, fragment ions produced from step 206 (i.e., fragment ions generated using a CID methodology) are further fragmented according to a HCD methodology as discussed above, injected into orbital trap 154, and detected. After Fourier transform analysis, the resulting set of mass spectral information features m/z values measured for the fragments, which can then be used (i.e., by controller 112) to identify specific TMT-tagged peptide species.

In general, TMT tags feature reactive groups that target terminal peptide amino groups, peptide cysteine amino acid side groups, or glycopeptides. During fragmentation, the tags generate specific reporter ion signatures. When particular peptides are being analyzed, quantitation can be performed by comparing intensities of the reporter ions in the mass spectral information.

Suitable methods for quantification of TMT-labeled peptides are disclosed, for example, in Thompson et al., "Tandem mass tags: a novel quantification strategy for comparative analysis of complex protein mixtures by MS/MS," *Analytical Chemistry* 75: 1895-1904 (2003), and in McAlister et al., "Increasing the multiplexing capacity of TMTs using reporter ion isotopologues with isobaric masses," *Analytical Chemistry* 84: 7469-7478 (2012), the entire contents of each of which are incorporated by reference herein.

After identification and quantification of the desired phosphopeptides is completed in step 210, the process shown in flow chart 200 terminates at step 212.

To evaluate the effectiveness of the foregoing multiplexed phosphopeptide analysis methods, a phosphopeptide library of phosphoserine-containing peptides was labeled with TMT0, one of the isobaric chemical tags, and the methods were evaluated based on the number of correct identifications of members of the library that were made. Specifically, a phosphopeptide library with the peptide sequence GAPXPXAXFEpS(K/R), where X was an equimolar mixture of 10 amino acid monomers (ADEFGLSTVY), was obtained from Cell Signaling Technology (Danvers, MA). After labeling with TMT0, the sample was desalted over Sep-Pak C18 solid-phase extraction (SPE) cartridges, and lyophilized. 1.5 µg of the peptide library was analyzed in each experiment.

The phosphopeptide library was analyzed using both CID and HCD fragmentation methodologies separately, at a series of activation energies. HCD fragmentation typically led to a larger number of peptide identifications than CID, with the highest number of peptide identifications coming with a normalized activation energy of 35-40%.

Figure 3:
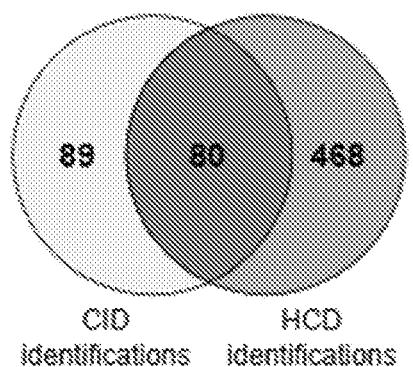
FIG. 3 is a schematic diagram showing quantities of peptides identified by CID-based fragmentation and by HCD-based fragmentation.

Then, to determine whether HCD fragmentation identified a superset of the phosphopeptides identified by CID fragmentation, or if the two methodologies identified different populations of peptides, phosphopeptides identified by duplicate runs of analysis with either CID fragmentation (activation energy=30%) or HCD fragmentation (activation energy=40%) were compared. Surprisingly, the HCD fragmentation methodology did not yield a superset of peptide identifications relative to the CID fragmentation methodology. While there was a 22% overlap population of peptides identified using both methodologies, separate populations of peptides were identified exclusively by the CID methodology, and exclusively by the HCD methodology. FIG. 3 is a graph showing the populations of peptides that were identified by the CID methodology alone (89 peptides), by the HCD methodology alone (468 peptides), and by both methodologies (80 peptides).

To understand the existence of peptide populations identified by only one of the fragmentation methodologies, the populations of peptide ion fragments formed by only one of the two fragmentation methodologies (i.e., the CID-based population and the HCD-based population) were then further fragmented, and the fragment properties examined.

In single activation CID, fragmentation of a peptide occurs only once at the weakest bond. On a phosphopeptide, the weakest bond is typically the bond between the phosphate group and the phosphorylated residue, resulting in the neutral loss of the phosphate group. The remaining species has less information for peptide identification. Accordingly, it was speculated that peptides with a very prevalent neutral loss species after CID fragmentation would be poorly identified by CID. In contrast, HCD fragmentation permits breakage of the peptide into several smaller species. After testing, it was found that peptides were successfully identified after CID fragmentation generally only when they had very low intensity neutral loss species, while peptides with much higher intensity neutral loss species were generally only successfully identified by employing HCD fragmentation. It was also observed that peptide identification after HCD fragmentation typically was successful with a relatively higher level of incoming peptides—as measured by precursor intensity—than identification after CID fragmentation, which was accomplished with a relatively lower level of incoming peptides.

After identifying TMT0-labeled phosphopeptides following single fragmentation methodologies based on CID and HCD, respectively, as discussed above, a second experiment was performed in which labeled phosphopeptides derived from the library were analyzed using the methods shown in FIG. 2. Specifically, labeled precursor phosphopeptides were fragmented using both CID and HCD methodologies. Subsequently, the ten highest intensity peptide ions fragmented using the CID methodology were selected for further (i.e., "MS3") analysis, where the peptide ions were fragmented again using the HCD methodology for purposes of peptide identification. Phosphopeptide identification performed according to the methods of FIG. 2 consistently outperformed phosphopeptide identification after a single CID- or HCD-based fragmentation step, identifying approximately 25% more peptides than methods involving a single HCD fragmentation, and approximately 50% more peptides than methods involving a single CID fragmentation. The results demonstrated that, surprisingly, a dual fragmentation methodology can yield a more comprehensive phosphopeptide dataset in spite of the reduced number of scans performed.

To further evaluate the multi-fragmentation analysis procedure on biological samples, proteins were isolated from mouse brain tissue and digested. The mouse brain tissue was suspended in mammalian lysis buffer (75 mM NaCl, 50 mM Hepes [pH 8.5], 10 mM sodium pyrophosphate, 10 mM sodium fluoride, 10 mM β-glycerophosphate, 10 mM sodium orthovanadate, 10 mM PMSF, EDTA-free protease inhibitor tablet, and 3% SDS). Suspensions were mixed with an equal volume of zirconium oxide beads and lysed on a mini bead beater (Biospec, Bartlesville, OK) four times for 45 seconds. Lysates was separated from the beads by centrifugation, and insoluble debris was discarded. The supernatant was then prepared for mass spectrometry analysis.

Phosphoenrichment using titanium dioxide beads was performed, and the phosphopeptide sample was fractionated into 12 fractions which were then labeled with ten TMT reagents. After phosphotyrosine antibody enrichment, the fractions were analyzed to perform phosphopeptide identification using a single CID-based fragmentation methodology, and also using the dual fragmentation methodology of FIG. 2.

The single fragmentation CID-based method was used to analyze 6 of the 12 fractions across 3-hour gradients. A total of 3380 unique phosphoforms were identified via this method, of which 56% were quantified. The dual fragmentation methodology of FIG. 2, applied to the other fractions, identified 12,315 unique phosphoforms, of which 47% were quantified.

Figures 4A, 4B:
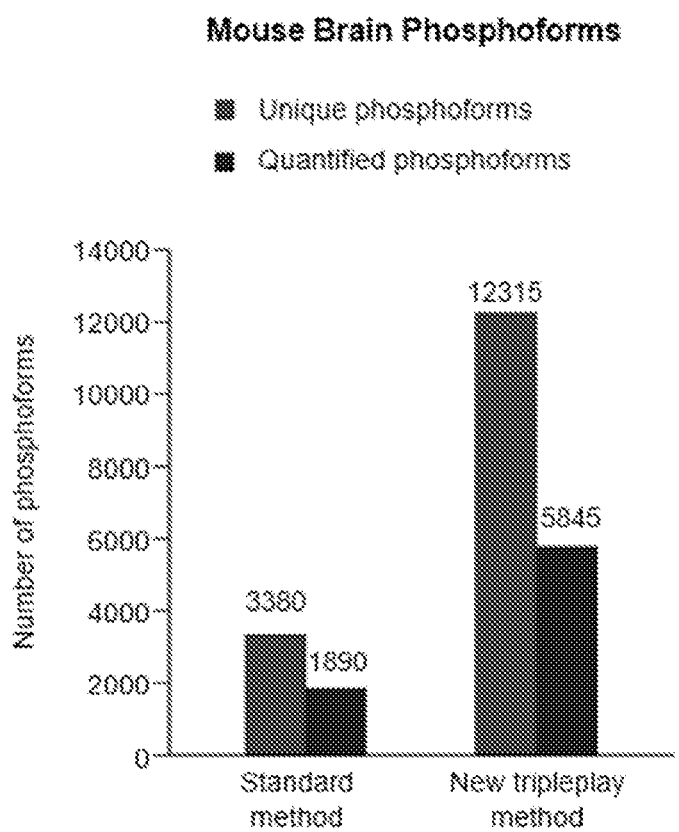
FIGS. 4A and 4B are graphs showing unique and quantified phosphoforms identified by CID-based fragmentation and by HCD-based fragmentation, respectively.

FIG. 4 is a graph showing the analysis results from the single fragmentation CID-based method ("A") and the dual fragmentation methodology ("B"). As shown in the graph, using the dual fragmentation methodology results in an approximately threefold increase in the number of unique, quantifiable phosphoforms in a multiplexed phosphoproteomics analysis.

Phosphoproteomic Profiling of Cell Lines—Application to Kinase Inhibitor Resistance Anaplastic lymphoma kinase (ALK) is a receptor tyrosine kinase (RTK) generally not expressed in the lung tissue. Chromosomal rearrangements involving the ALK gene were initially discovered in anaplastic large cell lymphoma. In non-small cell lung cancer (NSCLC), the ALK fusion gene (4-5% of NSCLC) produces a chimeric protein that is constitutively active and displays transforming capabilities. Therefore, ALK rearrangements represent a powerful oncogene that promotes proliferation, differentiation, and cell survival. ALK-positive patients are treated with tyrosine kinase inhibitors (e.g. Crizotinib, Ceritinib, Alectinib, Lorlatinib) but ultimately develop resistance to the therapy.

The resistance mechanisms to ALK inhibition include acquisition of secondary mutations in the ALK tyrosine kinase domain mutations or ALK gene amplification in about a third of the cases. The resistance can be mediated by the activation of bypass signaling such as KIT, EGFR, or IGF1R in some tumors. In about one third of resistant tumors, resistance mechanisms have yet to be identified. It is therefore essential to improve the understanding of tumor adaptation to treatment to provide therapeutic alternatives to overcome the development of resistance.

The analytical methods disclosed herein are well suited for applications involving phosphoproteomic profiling of cells that display resistance to various inhibitors. In particular, the methods are applicable to the study of cellular resistance to a variety of receptor tyrosine kinase inhibitors, and have the potential to increase understanding of the mechanisms underlying the resistance.

In the particular study reported here, resistance to the small molecule ALK inhibitor Ceritinib was studied. The patient-derived cell line H3122 is a NSCLC line with an EML4-ALK fusion, and it is sensitive to Ceritinib. To simulate the clinical development of therapeutic resistance following initial treatment, this cell line was cultured over a period of 6 months with low but increasing doses of Ceritinib. Over time, four single resistant clones were isolated, with IC50s at least twenty times higher than the parental sensitive cell line. These clones were expanded and comprise the cell lines LDKR1-4. Each of these cell lines was determined to have no mutations in the ALK sequence, suggesting that a secondary mechanism of resistance was at play.

Figure 5:
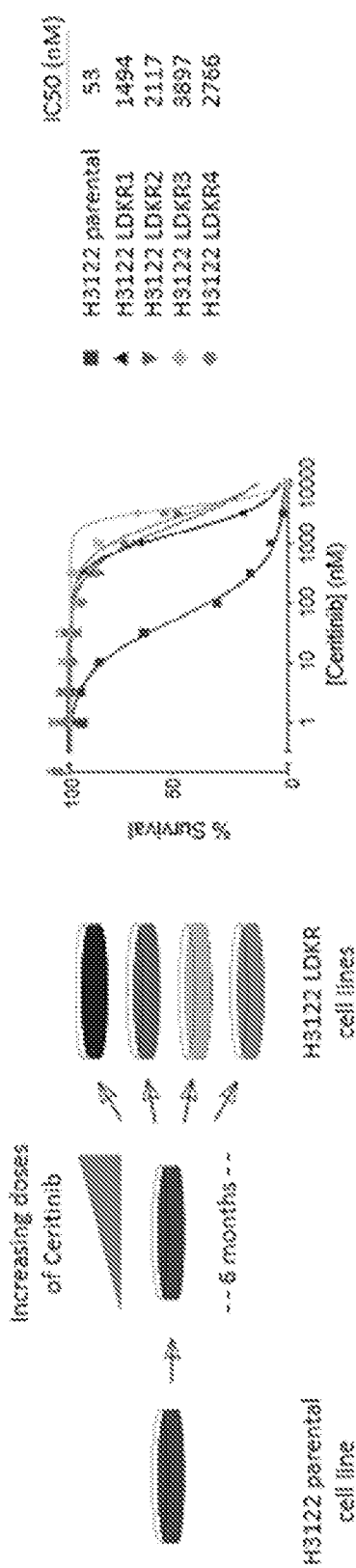
FIG. 5 is a schematic diagram showing development of cell lines from a parent H3122 cell line.

FIG. 5 is a schematic diagram showing the development of the cell lines. The ALK-positive H3122 cell line, which is sensitive to the ALK inhibitor Ceritinib (IC50=53 nM), was treated with escalating doses of Ceritinib over a period 6 months. Resistant clones LDKR1-4 were obtained with IC50 values in a range from 1494 nM to 3897 nM.

The H3122 parental and LDKR1-4 cell lines were each grown in culture with or without the addition of Ceritinib for 24 hours, and harvested cells were subsequently processed for both proteomic and phosphoproteomic analyses. Specifically, each of the cell lines was cultured in RPMI-1640 media supplemented with 10% FBS, 100 units/mL penicillin, and 100 µg/mL streptomycin. Cells were treated for 24 hours with 300 nM Ceritinib (also known as LDK378). Cells were collected, and the cell pellets were resuspended in mammalian lysis buffer and lysed by passage through a 21 gauge needle. The lysate was centrifuged at 15,000×g for 5 minutes at 4° C., and insoluble debris was discarded.

The lysates were then prepared for mass spectrometry analysis. Samples were reduced with DTT, alkylated with iodoacetamide, and precipitated with methanol/chloroform. Protein was digested overnight at room temperature with endoproteinase Lys-C (obtained from Wako Chemicals, Richmond, VA) followed by digestion with sequencing-grade trypsin (obtained from Promega Corp., Madison, WI) for 6 hours at 37° C. Samples were quenched with 1% TFA and desalted using Sep-Pak $C_{18}$ (SPE) cartridges (obtained from Waters Corp., Milford, MA). The peptide concentration of each sample was determined using a BCA assay.

For proteomic profiling, 50 µg of digested peptides were labeled with TMT10-plex reagents following phosphopeptide enrichment (as discussed below). After labeling, the peptide samples were acidified, pooled, desalted over Sep-Pak $C_{18}$ SPE cartridges, and lyophilized. The pooled samples were then analyzed using a standard LC/MS3 methodology.

For phosphoproteomic analysis, 2.0 mg of digested peptides were enriched for phosphopeptides using titanium dioxide beads, labeled with TMT10-plex reagents, and further enriched with a phosphotyrosine antibody. Specifically, 8 mg of titanium dioxide beads were incubated with the peptide in binding buffer (2 M lactic acid in 50% ACN/50% $H_2O$) for 1 hour with gentle shaking. Beads were collected by centrifugation at 1,000×g for 1.5 minutes, followed by washing 3× with binding buffer and 3× with 50% ACN/0.1% TFA. Enriched phosphopeptides were eluted 2× with 0.2 mL of 50 mM $KH_2PO_4$, pH 10. Samples were acidified and desalted over Sep-Pak $C_{18}$ SPE cartridges. Following TMT labeling, phosphopeptides were further enriched for phosphotyrosine (pY)-containing peptides using pY antibody-conjugated beads (obtained from Cell Signaling Technology, Danvers, MA). All unbound peptides (pS and pT peptides) were collected, acidified, and desalted. pY peptides were eluted from the beads, acidified, and desalted using Stage Tips.

pS/pT peptide mixtures were resuspended in 5% ACN, 5% formic acid and fractionated by high pH reverse-phase high pressure liquid chromatography. Samples were separated over a 4.6 mm×250 mm ZORBAX Extend $C_{18}$ column (5 µm, 80 Å, obtained from Agilent Technologies, Santa Clara, CA) using a two buffer system (Buffer A: 5% ACN, 10 mM ammonium bicarbonate; Buffer B: 90% ACN, 10 mM ammonium bicarbonate) using a 5-28% Buffer B gradient at a flow rate of 500 µL/minute over 70 minutes. Collected fractions were then dried and resuspended in 5% ACN, 5% formic acid. Phosphoserine-, phosphothreonine-, and phosphotyrosine-containing phosphopeptides were then analyzed using the dual fragmentation methodology of FIG. 2.

In the present experiment and in others discussed herein, liquid chromatography was performed on samples before the samples were introduced into the mass spectrometry system. 100 µm inner diameter microcapillary columns were packed with 0.5 cm of Magic C4 resin (5 µm, 100 Å, obtained from Bruker, Billerica, MA), followed by 0.5 cm of Maccel $C_{18}$ resin (3 µm, 200 Å, obtained from Nest Group, Southborough, MA), followed by 29 cm of GP-$C_{18}$ resin (1.8 µm, 120 Å, obtained from Sepax Technologies, Newark, DE). Peptides were eluted over a gradient of 6-25% or 8-28% ACN in 0.125% formic acid at a flow rate of 300 nL/minute. Gradients lasted either 70 minutes or 165 minutes.

In the present experiment and in others discussed herein, mass spectrometry methods were performed as follows. An initial precursor ion scan ("MS1") was performed in the orbitrap (resolution=60,000; AGC target=$2\times10^5$; maximum injection time=100 ms; m/z range=500-1500 Th), and ions for fragmentation analysis were selected using TopN mode (10 ions). For single fragmentation analyses, fragmentation ("MS2") was performed according to CID or HCD methodologies, with activation energies ranging from 20-45%, and with a maximum injection time of 70 ms. Detection of ion fragments derived from the HCD methodology was performed in the orbitrap (resolution=15,000), with an AGC target of $1\times10^4$ and an isolation specificity of 0.5 Th.

In the dual fragmentation methods ("MS2"), CID fragmentation (activation energy=30%) with ion trap detection was performed in parallel with HCD fragmentation (activation energy=40%) with orbitrap detection (resolution=15,000) on the same precursor ion from the MS1 analysis. The top 3 intensity fragment ions from the CID-based MS2 spectrum were synchronously selected for further fragmentation analysis.

The further fragmentation analysis ("MS3") was performed according to a HCD methodology with orbitrap detection (activation energy=55%, resolution=60,000, AGC target=$1\times10^5$, maximum injection time=150 ms, isolation specificity=0.5 Th).

Across the 10 samples that were profiled, proteomic analysis quantified 7,638 proteins, and phosphoproteomic analysis quantified 23,220 unique phosphopeptides (or "phosphoforms"). Of the quantified phosphoforms, about 80% (18,603) had precise localization of the phosphorylation event or events (p<0.05), confirming good fragmentation of the phosphopeptides.

In the present experiment and others discussed herein, the identification of specific peptides following the dual fragmentation methodology was performed as follows. Mass spectral information was searched against a protein sequence database containing all protein sequences in the human UniPort database, as well as that of known contaminants like porcine trypsin. Spectra were matched to peptide sequences using a target-decoy database strategy (described, for example, in Elias et al., "Target-decoy search strategy for increased confidence in large-scale protein identifications by mass spectrometry," *Nat. Methods* 4: 207-214 (2007)), consistent with trypsin specificity with up to two missed cleavage sites and a precursor ion m/z tolerance of 50 ppm. Static modifications were defined as (i) TMT tags on the N-terminus and on lysine residues (229.162932 Da) and (ii) carbamidomethylation on cysteine residues (57.021464 Da), and variable modifications were defined as oxidation on methionine residues (15.994915 Da). Peptide and protein assignments were filtered to a protein FDR of less than 1%. Peptides which could match to more than one protein sequence were assigned to the protein with the most matching peptides. TMT report ion intensities were calculated and normalized.

Hierarchical clustering of both the proteomic and phosphoproteomic datasets resulted in near-identical groupings of the 10 samples. FIGS. 6A and 6B are plots showing clustering of the cell lines in both the proteomic (FIG. 6A) and phosphoproteomic (FIG. 6B) analyses. In all but one case, the untreated cell line most closely clustered with its drug-treated partner, reinforcing the fact that four of the five cell lines are highly resistant to Ceritinib and likely are weakly affected by the addition of the drug. At the cell line level, two clusters clearly emerged, one with the parental and LDKR1 cell lines, and a second with the LDKR2, LDKR3, and LDKR4 cell lines. This reveals that LDKR1 (the least resistant of the four resistant clones) remained more similar to the parental cell line, while LDKR2, LDKR3, and LDKR4 evolved away from the parental cell line but in related ways. This suggests that the cell line, and not the presence or absence of the drug, drives the clustering.

FIGS. 7A and 7B are plots showing the ranges of changes in measurements for each protein (FIG. 7A) or phosphoform (FIG. 7B) compared to the measurements of proteins and phosphoforms, respectively, present in the H3122 parental cell line with no drug added. For both plots, the median centered at a 1:1 ratio. While the middle 50% of the proteins stayed within a 2-fold increase or decrease as compared to their parental cell line (i.e., no drug) values, the phosphoproteomic ratios were substantially more variable, with ratios extending out to 25-fold changes and higher, as shown in FIG. 7B. These data indicate that a small number of RNA or protein-level changes may have resulted in large changes in downstream signaling pathways, as measured by the phosphoproteome profiling.

Figure 8:
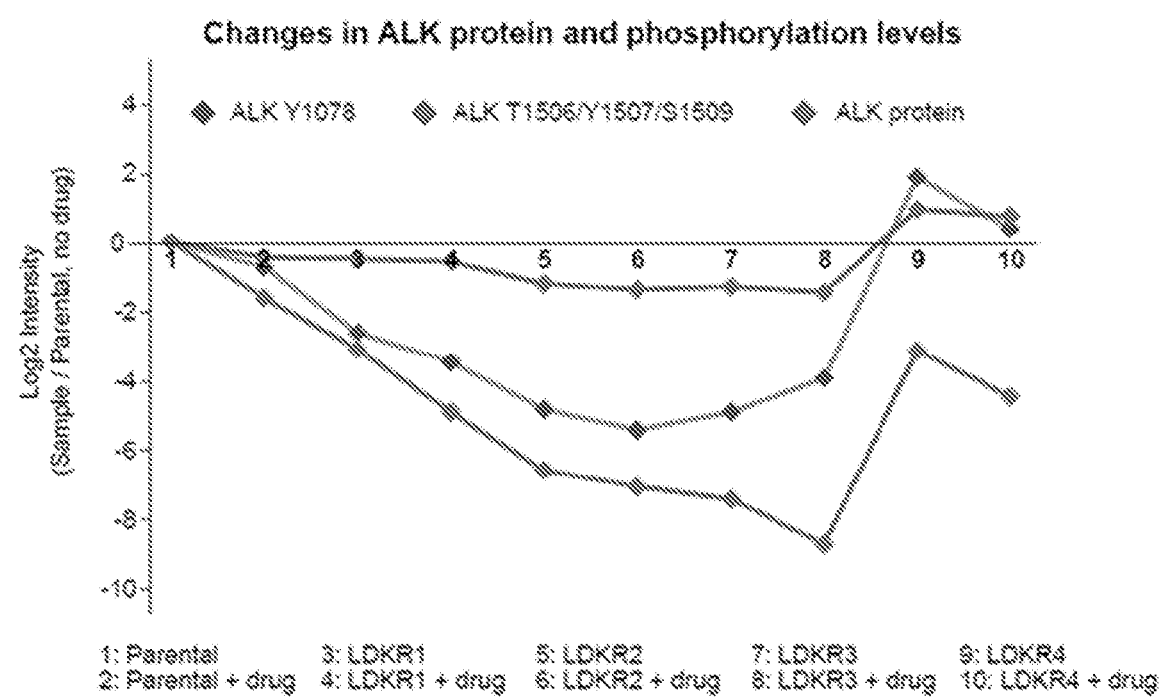
FIG. 8 is a plot showing changes in ALK protein and phosphorylation levels for the five cell lines of FIGS. 6A and 6B.

Changes in the protein and phosphoform levels of ALK, the direct target of the drug treatment, were also examined. FIG. 8 is a plot showing changes in ALK protein and phosphorylation levels, expressed as the ratio of the measured level to the level in the parental cell line with no drug added, for ALK protein, and for two ALK phosphoforms: ALK phosphorylation on Tyr 1078 ("ALK Y1078"), and on Thr 1506, Tyr 1507, or Ser 1509 ("ALK T1506/Y1507/S1509"). ALK protein levels decreased slightly in LDKR1, LDKR2, and LDKR3 (up to a threefold decrease) but increased twofold in LDKR4. Changes in two phosphorylation sites on ALK showed a more dynamic phenotype. Tyr 1078 phosphorylation decreased upon drug treatment in the parental cell line and further decreased in LDKR1, LDKR2 and LDKR3. Coincident with the ALK protein increase in LDKR4, Tyr 1078 phosphorylation also increased. Phosphorylation on the second phosphoform was less well localized (Thr 1506/Tyr 1507/Ser 1509), and the phosphorylation was even more dramatically effected, decreasing fourfold upon drug treatment in the parental cell line and further dropping over 50-fold in LDKR1, LDKR2, and LDKR4. This phosphorylation also rebounded in LDKR4 to near baseline levels.

Notably, phosphorylation on Tyr 1507 is required for binding of the Shc adaptor protein and downstream signaling events. These data indicated that Ceritinib treatment continued to be effective at inhibiting ALK activity in at least three of the four resistant cell lines. Moreover, by using the dual fragmentation methodology disclosed herein, phosphoproteomic analysis based on the peptide identification and quantification results was capable of detecting the modulation behavior associated with ALK activity following Ceritinib treatment.

Analysis of differences between the parent and resistant cell lines might provide important information about the mechanisms underlying resistance to treatment by Ceritinib. Moreover, similar analytical methods can be used to study resistance to inhibitors of receptor kinases. The methods focus on the role of kinases for two reasons. First, in this particular study, the initial drug target ALK is a receptor tyrosine kinase with a critical function in several upstream signaling pathways, and other kinases affecting these signaling pathways would be a logical mechanism for bypassing the dependence on ALK. Additionally, kinases are the targets for a large sector of currently available clinically-approved drugs, and would thus allow for a more streamlined application of the results for clinical use.

Figure 9:
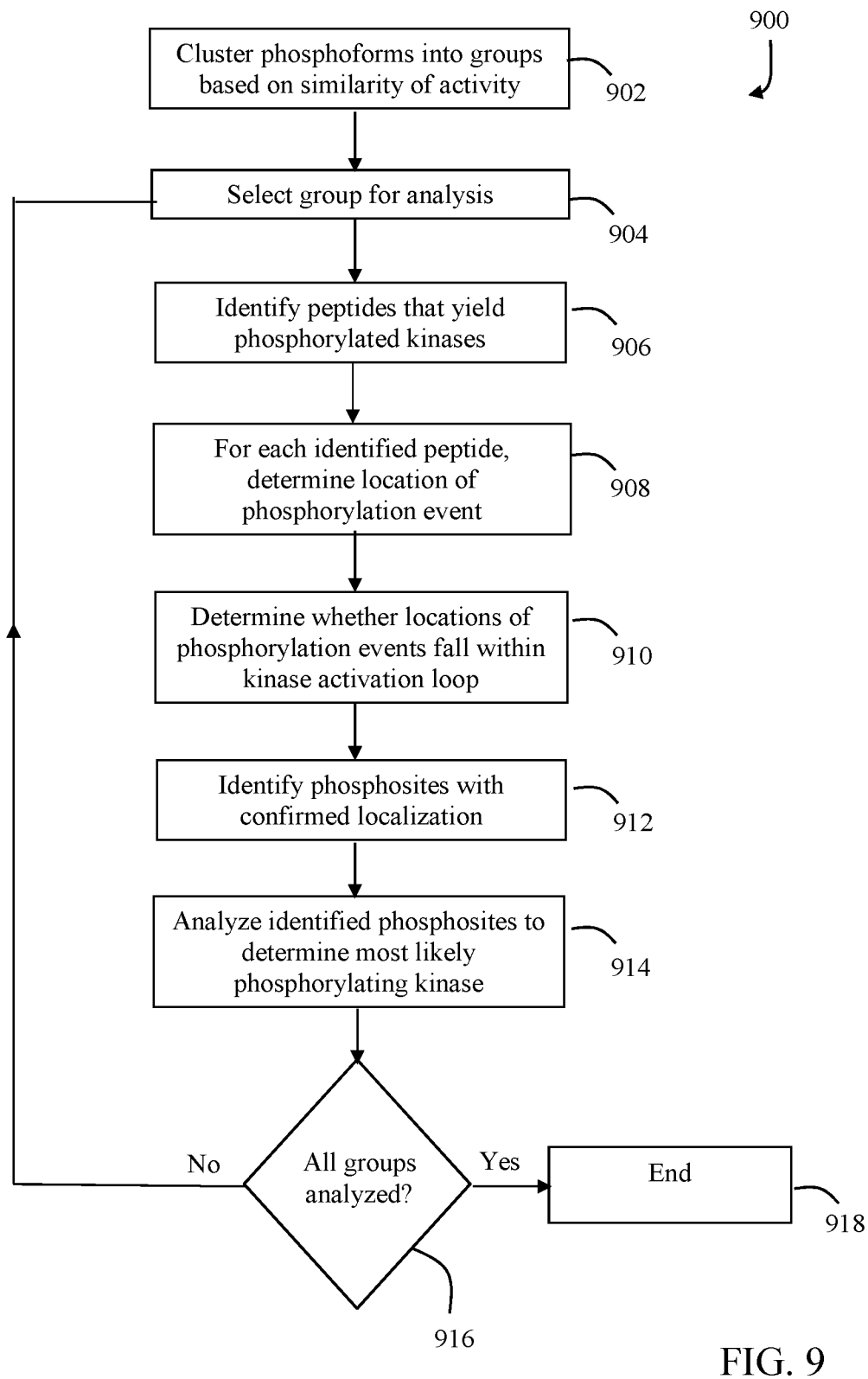
FIG. 9 is a flow chart showing a series of steps for identifying relevant kinases corresponding to identified phosphosites.

To analyze the phosphoproteome dataset in an unbiased manner, a technique was developed to identify particular kinases of interest. FIG. 9 is a flow chart 900 showing a series of steps that can be performed to identify relevant kinases. In a first step 902, the quantitative information for all phosphoforms is clustered into groups based on the similarity of activity of the phosphoforms across all samples. A variety of different techniques can be used to perform clustering. For example, in some embodiments, K-means clustering is used to identify appropriate groups.

Next, in step 904, one of the groups determined in step 902 is selected for analysis. In step 906, peptides which exhibit phosphorylation on a kinase itself are identified, and in particular, peptides which show increased levels of phosphorylation. For each of these peptides, the location of the phosphorylation event is determined in step 908. Then, in step 910, the locations of the phosphorylation events for the peptides are compared to the known activation loop of the kinase to determine whether the peptide falls within the kinase's activation loop. It is expected that hyperphosphorylation of a kinase, particularly within its activation loop, is suggestive of hyperactivity.

Next, in step 912, all phosphosites in the cluster with confirmed localization ($p \leq 0.05$) are identified. The identified phosphosites are then analyzed in step 914 to determine the most likely phosphorylating kinase for each. Suitable methods for performing the analysis in step 914 include applying the NetworKIN algorithm, disclosed for example in Horn et al., "KinomeXplorer: an integrated platform for kinome biology studies," *Nature Methods* 11: 603-604 (2014), the entire contents of which are incorporated by reference herein. The determination of the most likely phosphorylating kinase is typically based, for example, on kinase consensus sites and functional proximity.

As an example, in some embodiments, the most likely kinase for each phosphorylation event can be determined as the kinase with the best score for each phosphorylation event, irrespective of absolute score. Enrichment of hyperphosphorylated substrates can be determined using a hypergeometric test, and the Benjamini-Hochberg procedure (described, for example, in Benjamini et al., "Controlling the false discovery rate: a practical and powerful approach to multiple testing," *J. R. Statist. Soc.* 57: 289-300 (1995), the entire contents of which are incorporated by reference) can be used to control the false discovery rate to 5%.

In step 916, the procedure determines whether all groups formed in step 902 have been analyzed. If so, the procedure terminates at step 918, having determined the set of kinases for each of the groups that represent the kinome activity profile for each group. If all groups have not yet been analyzed, control returns to step 904 where a new group is selected for analysis. It is expected that kinases identified through the procedure shown in FIG. 9 (i.e., based on the locations of observed phosphorylation events in step 910 and/or based on identified phosphosites in step 914) for each group represent putative drivers of the phenotype of interest for that group.

Figure 10:
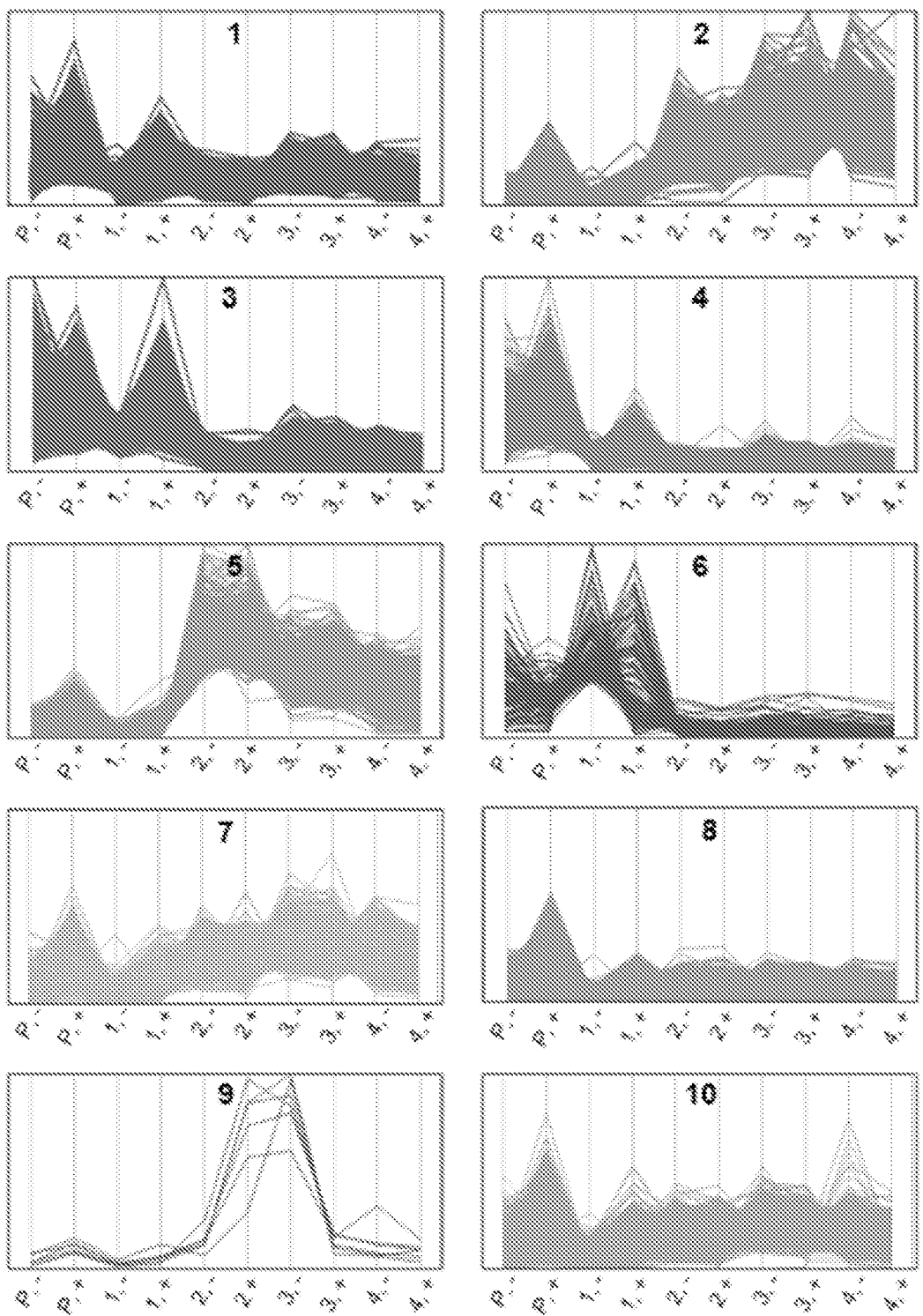
FIG. 10 is a set of plots of different groups of phosphoforms with similar activity.

The procedure shown in FIG. 9 was then applied to the H3122-derived phosphorylation data. The data was first clustered into ten activity groups. FIG. 10 is a set of plots that show each of the ten groups. Groups of phosphoforms with high activity in certain resistant cell lines were of particular interest. For example, groups 3 and 6 represented phosphoforms which changed dramatically in LDKR1, group 5 consisted of phosphoforms demonstrating particularly large changes in LDKR2, and groups 2 and 7 represented high levels of phosphorylation across LDKR2, LDKR3, and LDKR4 relatively equally. These three groups represented three potentially distinct mechanisms of resistance to Ceritinib in the H3122 cell line panel.

Figure 11A:
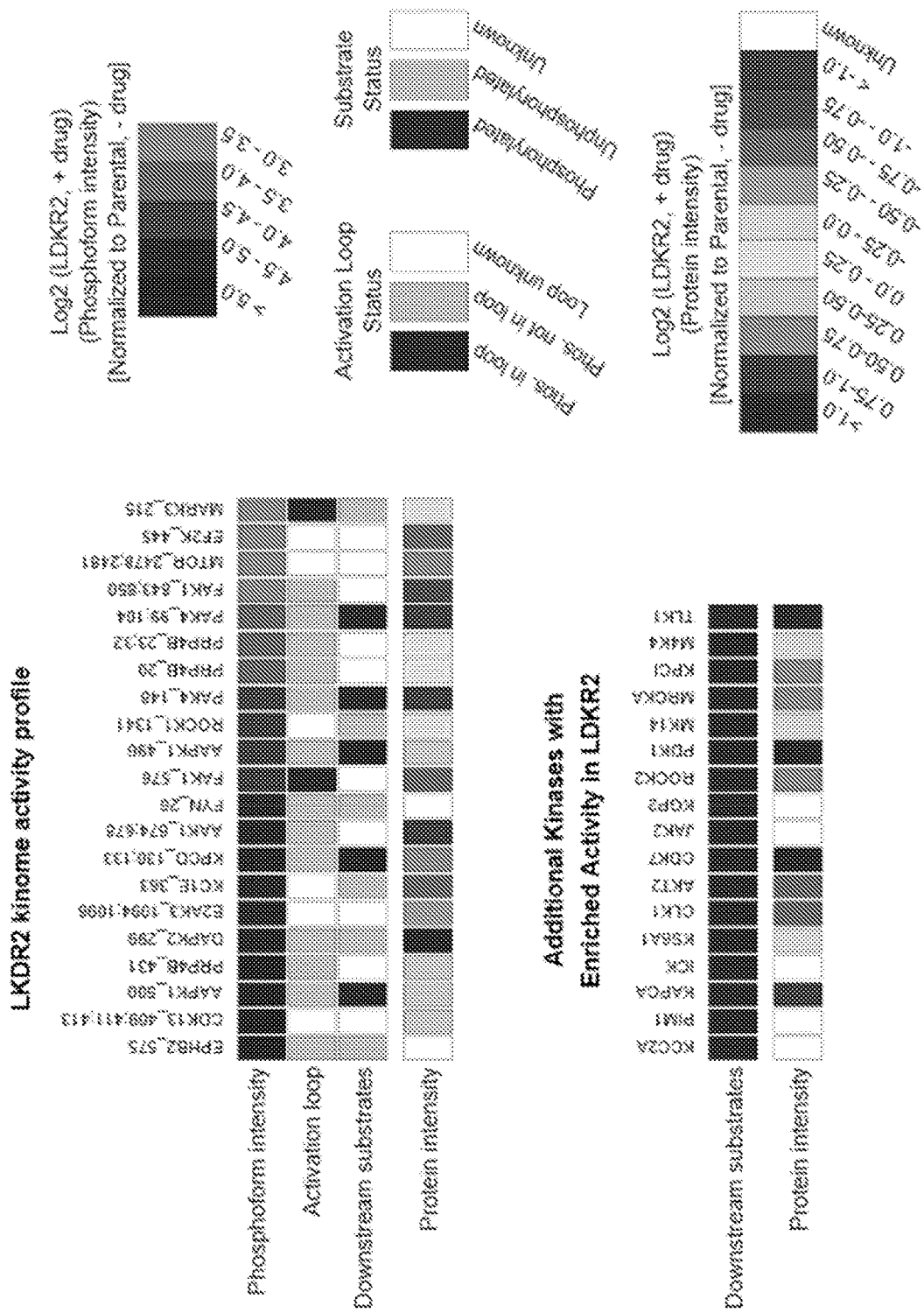
FIGS. 11A-11C are schematic diagrams of activity profiles for three different groups of phosphoforms (with activity in cell line LDKR2, activity in cell line LDKR1, and activity in cell lines LDKR2, LDKR3, and LDKR4, respectively).
Figure 11B:
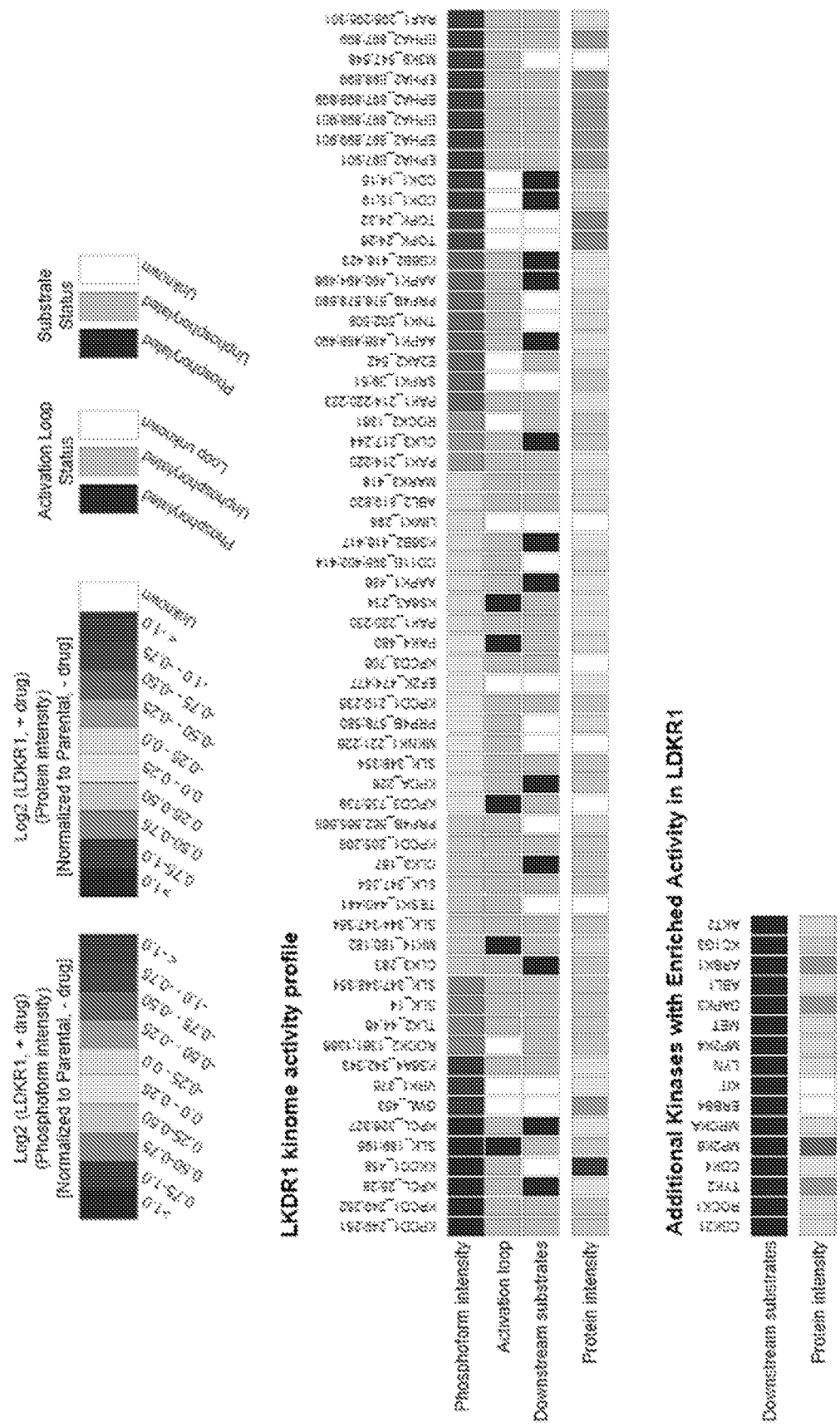
Figure 11C:
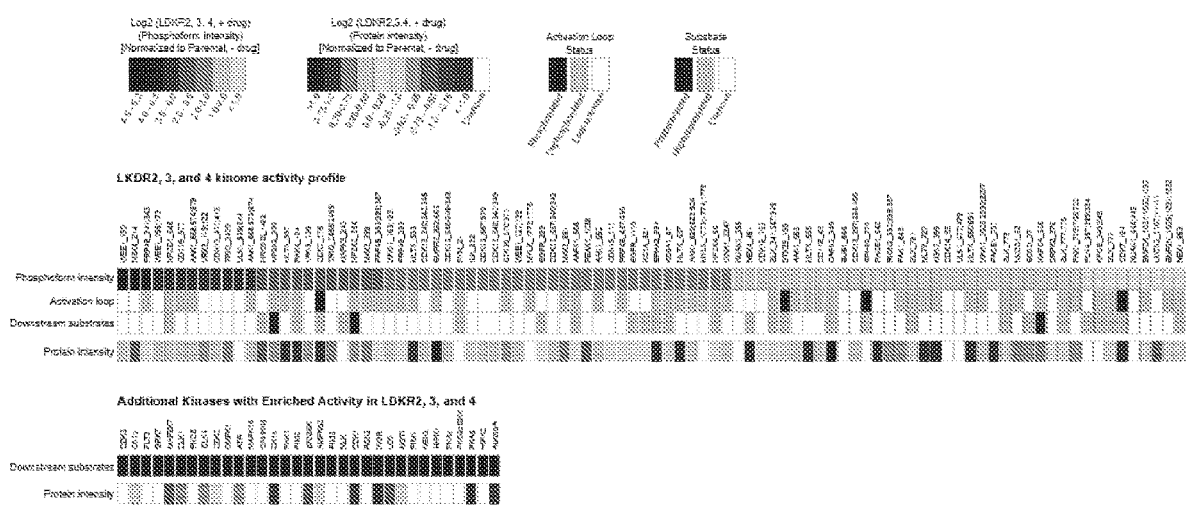

Having identified groups of phosphoforms with high activity in LDKR1, in LDKR2, or in LDKR2, LDKR3, and LDKR4 together, kinase activity was examined. Kinome activity profiles were generated for each of these groups. FIG. 11A is an example plot showing the kinome activity profile generated for LKDR2, while FIGS. 11B and 11C are plots showing the kinase activity profiles for LKDR1 (FIG. 11B), and for LKDR2, LKDR3, and LKDR 4 (FIG. 11C) together. The activity profiles in FIGS. 11A-11C include both kinases which were hyperphosphorylated themselves in the group (the upper left plot in each figure) as well as those kinases which were only identified based on the activity of their substrates (the bottom left plot in each figure). For example, referring to FIG. 11A, phosphorylation events on kinases themselves are shown in the upper left plot, from most to least upregulated. Two of the phosphorylation events in the upper left plot fell within the activation loop of the kinase.

In addition, several kinases had no observed phosphorylation on the kinase itself, but had hyperphosphorylated substrates, as shown in the lower left plot of FIG. 11A. In comparison, the protein intensity of each kinase was frequently not upregulated, suggesting that many of the observed effects were due to activity changes or upstream signaling events.

The range of changes shown in the activity profiles for each of the three groups was quite different. Phosphoforms with changes most substantially in LDKR1 were primarily within a two-fold difference of the H3122 parental cell line, while phosphoforms upregulated in LDKR2, LDKR3, and LDKR4 reached up to 25-fold increases as compared to the parental cell line. The data in the activity profiles agrees with the hierarchical clustering shown in FIG. 6B, which showed LDKR1 to be the most similar to the parental cell line.

In each of the identified groups, there were kinases which were hyperphosphorylated on multiple residues. For example, phosphoforms changing substantially in LDKR1 included SLK phosphorylation at residues 14, 189, 195, 344, 347, 348, 354, while FAK1 was highly phosphorylated at residues 576, 843, and 850 in LDKR2. Such information might add further confirmation to the hyperactive state of the kinase.

One explanation for the high levels of a kinase's activity could be merely that the kinase itself could be present at high concentration. To examine this possibility, for each of the kinases in the kinome activity profiles, the relative protein level as compared to the parental cell line with no drug treatment was calculated. While a handful of the kinases identified in each group were upregulated two-fold or more, the majority were only weakly changed, and many were actually downregulated in the resistant cell lines. This demonstrated that the proteomic and phosphoproteomic datasets provided complementary information, both of which could be useful in identifying critical proteins for a biological phenotype.

Several kinases were also identified as hyperactive across multiple parameters. In the LDKR1 group, five kinase phosphorylations were located within the kinase's activation loop, including phosphorylations on SLK and S6 kinase α, and 6 identified kinases had hyperphosphorylated substrates, including PKCη and S6 kinase β. In the LDKR2 group, two kinase phosphorylations were within the kinase's activation loop (FAK1 and MARK3), and three identified kinases had hyperphosphorylated substrates (AMPKα, PKCδ, and PAK4). Finally, in the LDKR2, LDKR3, and LDKR4 group, three kinase phosphorylations were within the kinase's activation loop (CDK7, STK25, and EPHB2), and 2 identified kinases had hyperphosphorylated substrates (MAPKK2 and PKA). These kinases in particular represented the highest priority hits as putative drivers in the resistance of these cell lines.

To determine how well the kinase analysis of phosphorylation data could predict kinases critical for the resistance to Ceritinib, the identified highest priority kinases were compared to data obtained from an orthogonal shRNA screen. A pooled shRNA screening library against roughly 400 kinases was used to infect the four resistant cell lines, followed by treatment with Ceritinib. Cell viability was then evaluated 7 days post-treatment, and effective shRNA clones were identified. shRNA clones targeting the same gene were evaluated as a group based on their respective ranks in the final list, giving a redundant siRNA activity (RSA) score for each gene. This technique had the advantage of both integrating information from multiple clones targeting the same gene as well as discounting off-target effects for any individual clone.

Figure 12A:
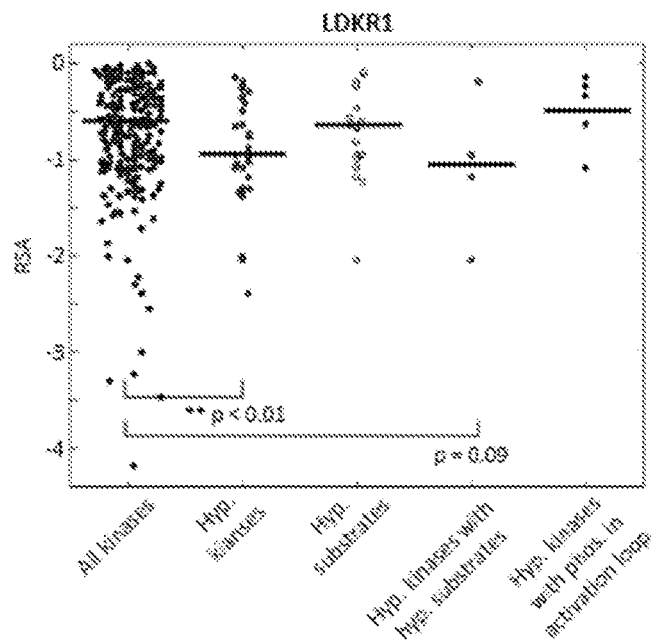
FIGS. 12A-12C are plots showing RSA scores for the three groups of phosphoforms of FIGS. 11A-11C.
Figure 12B:
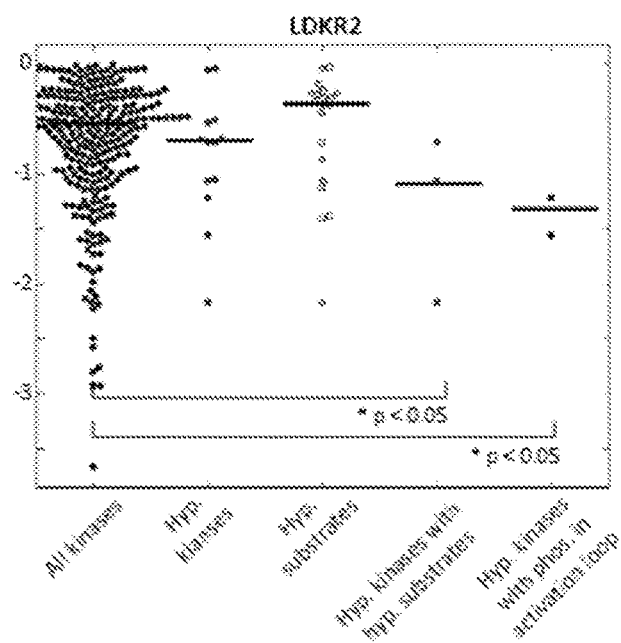
Figure 12C:
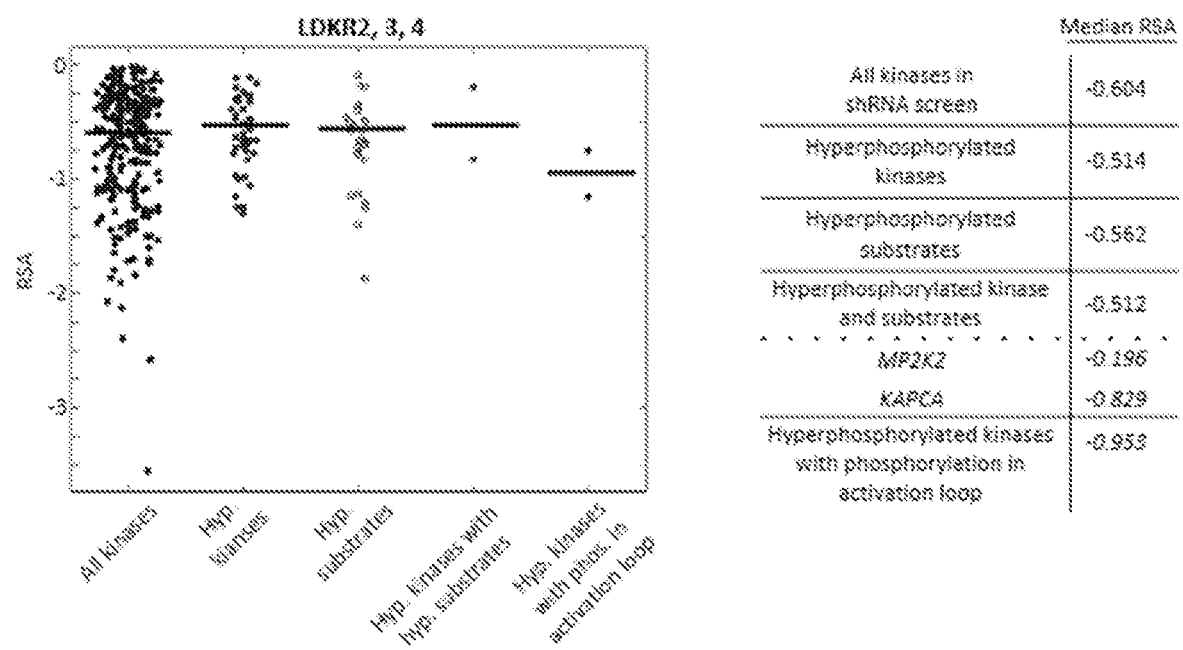

After performing this analysis, the shRNA dataset was filtered to select those kinases that were identified in the analysis performed according to FIG. 9. RSA scores across all of these kinases ranged from 0 (no effect) to −6, with a median score of −0.62. The shRNA data were then partitioned according to each of the three previously identified groups: LDKR1, LDKR2, and LDKR2, LDKR3, and LDKR4 together. FIGS. 12A-12C are plots showing RSA scores for each of the foregoing groups, respectively, distributed among the following categories: (i) all overlapping kinases; (ii) hyperphosphorylated kinases; (iii) kinases with hyperphosphorylated substrates; (iv) hyperphosphorylated kinases with hyperphosphorylated substrates; and (v) hyperphosphorylated kinases with phosphorylation in the activation loop. Median RSA scores for each category are also shown in FIGS. 12A-12C.

To evaluate the predictions made by the kinome activity profiles, the relative distributions of scores for predicted driver kinases were examined in the following classes: (i) hyperphosphorylated kinases; (ii) kinases with hyperphosphorylated substrates; (iii) hyperphosphorylated kinases with hyperphosphorylated substrates; (iv) hyperphosphorylated kinases with phosphorylation in the activation loop. For LDKR1, consideration of all of the hyperphosphorylated kinases gave a statistically significant improvement in the RSA scores ($p<0.01$). Additionally, looking at the overlap of hyperphosphorylated kinases that also had hyperphosphorylated substrates also showed an improvement, albeit just above statistical significance due to the small sample size. For LDKR2, looking at the overlap of hyperphosphorylated kinases with hyperphosphorylated substrates or at the overlap of hyperphosphorylated kinases with phosphorylation in the activation loop both resulted in improved RSA scores ($p<0.05$). Finally, for the LDKR2, LDKR3, and LDKR4 group, none of the kinase categories were enriched for lower RSA scores.

Based on these data, the hyperphosphorylated kinases with hyperphosphorylated substrates were examined further, as this category showed the most consistent improvement across the cell lines. There were only a few of these kinases in each group, but the predictions demonstrated a marked improvement in the shRNA screens for the LDKR1 and LDKR2 groups, with mean RSA scores of −1.072 and −1.067, respectively. The relevance of these kinases in cell resistance to Ceritinib was further confirmed by single siRNA knockdown in the relevant cell lines. The foregoing data confirm that the depth of information obtained through phosphoproteomic analysis can be leveraged through our kinome activity profiling to predict key players in resistance to therapeutic intervention.

In LDKR1, four kinases were identified and subsequently confirmed as potential drivers of Ceritinib resistance: AAPK1, KS6B2, KPCA, and KPCL. AAPK1 is part of the catalytic subunit of AMPK, a regulator of energy homeostasis that generally inhibits costly processes like protein translation. This protein has been shown to have both tumor promoting and tumor suppressing capacity, depending on the tumor stage and environmental conditions as well as the particular subunits in the AMPK complex. KS6B2, or ribosomal S6 kinase 2 (S6K2), along with its partner protein ribosomal S6K1, are downstream effects of the AKT/mTOR signaling arm, and phosphorylation of the ribosome by S6K results in increased translation and cell growth. Finally, KPCA and KPCL are components of the protein kinase C (PKC) family, a master switch of cellular signaling that responds to calcium and diacylglycerol signals to regulate such diverse processes as survival, migration, and apoptosis. Recent work has shown that PKC activation is sufficient to drive resistance to the MET/ALK inhibitor Crizotinib, and combined inhibition of ALK and PKC was capable of overcoming this resistance. PKC has also been shown to phosphorylate S6K2 and cause retention of its active form in the cytoplasm, providing a link between these two drivers.

AAPK1 and KPCD (another member of the PKC family) were also identified as potential drivers of resistance in LDKR2, along with PAK4. PAK4 is part of the p21-activated kinase family, downstream effectors of the Rho GTPases. While this family is not commonly mutated in cancer, all of the PAKs are frequently overexpressed in several cancer types. Constitutively active PAK4 can induce anchorage-independent cell growth as well as inhibition of apoptosis, two hallmarks of oncogenic transformation. Together, all of these kinases represent powerful regulators of cellular signaling nodes, and combined inhibition of ALK and these targets could be therapeutically beneficial in cases of resistance.

Characterization of Functional Proteomic Networks

The enhanced throughput and improvement in the number of peptides identified that results from employing a dual fragmentation methodology as discussed above can also be realized when such methodologies are applied to other analyses. This section discusses the characterization of functional proteomic networks and proteome-wide measurement of protein abundances. While the specific data presented were obtained using a single fragmentation methodology, the methods can also be implemented with the dual fragmentation methodologies of FIG. 2.

The proteome forms a link between genotype and phenotype, and its exploration provides a wealth of information about the molecular mechanism regulating cellular events. However, due to historical technical limitations of mass spectrometry-based proteomics, mainly affecting the technology's throughput capacity, the global measurement of messenger RNA levels is yet the main source of data to estimate the protein concentration levels on a global scale. Growing evidence of a significant divergence between mRNA and protein levels, as well as recent developments in increasing the throughput capacity of mass spectrometry-based proteomics through multiplexing technology, have shown the importance and the potential for acquiring direct proteome-wide measurement of protein abundances.

Disclosed herein are methods that use multiplexed quantitative proteomics to profile the proteomes of multiple cell lines (e.g., a panel of breast cancer cell lines), and to compare the proteomics data to mRNA levels to evaluate potential new insights in intra-cellular regulation provided by the proteomics data. As will be discussed in more detail below, the analysis can reveal functional protein-protein interactions, an understanding of which is essential for understanding a cell as an integrative system.

Multiplexed quantitative mass spectrometry-based proteomics was used for peptide measurements, applying isobaric labeling technology with 10-plex TMT reagents to generate quantitative proteome profiles of 41 breast cancer cell lines. The analyzed panel of cell lines captured the gamut of clinically relevant breast cancers comprised of models of the luminal, basal, claudin-low, and ErbB2 amplified subtypes and included four nonmalignant breast cell lines. A total of 82 proteome samples from two biological replicates were analyzed in 11 experiments, of which each enabled the simultaneous quantification of 10 samples.

The 41 cell lines were cultured as biological duplicates, cells were lysed, protein harvested, and digested with LysC and trypsin. The generated peptide mixtures were individually and in random order labeled with one out of eight TMT-10plex reagents. Labeled peptide mixtures were sorted into groups of eight, each containing only one peptide mixture labeled with each of the eight TMT-reagents. Standard peptide mixtures pooled from several cell line proteome digests were employed as standards to compare quantitative results from the individual TMT10-plex measurements. This was achieved through labeling the pooled standard digests with the remaining two TMT-reagents (brown and light blue) and adding them to each of the series of labeled peptide mixtures. Samples within each group were pooled and subjected to basic pH reversed phase liquid chromatography (bRPLC) followed by ion fragmentation for identification (MS2) and quantification (MS3) of the peptides.

Figure 13:
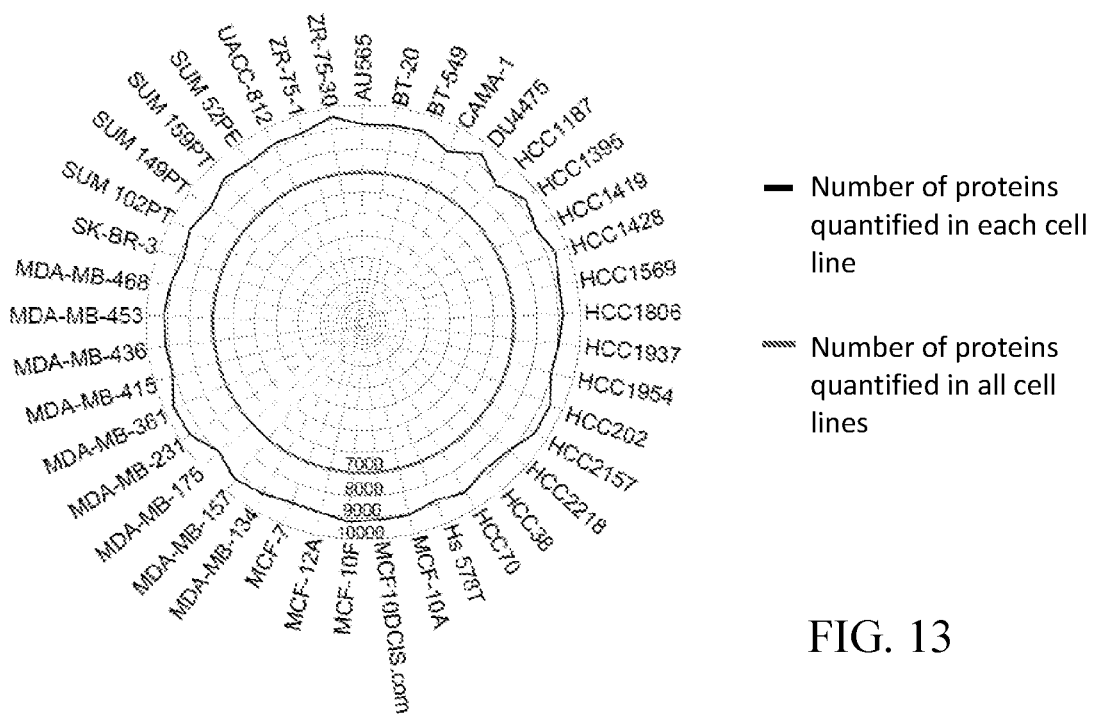
FIG. 13 is a radar plot showing protein quantification across multiple cell lines.

Data were acquired on an Orbitrap Fusion™ mass spectrometer (obtained from Thermo Fisher), using the Multi-Notch MS3 method to eliminate ratio distortions known to negatively affect the accuracy and reproducibility of quantitative proteomics data acquired using multiplexed isobaric labeling technology. A total of 10,535 proteins were quantified across all 11 experiments, and on average 9,115 proteins were quantified across the two replicate analyses of each cell line, while requiring under 10 hours of data acquisition time per cell line. The number of proteins quantified in all cell lines was 6,911, and subsequent analyses were performed on this subset. FIG. 13 is a radar chart showing the proteins that were quantified using the above procedure.

Figure 14:
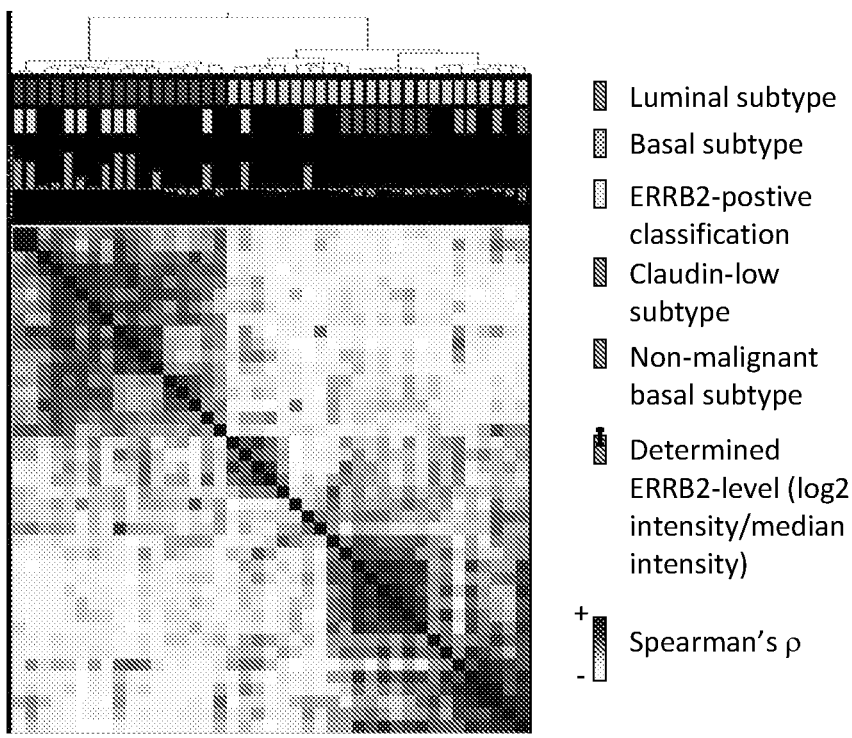
FIG. 14 is a plot of Spearman's rank correlation coefficient across 41 different cell lines.

When clustered based on the Spearman's rank correlation coefficient among the proteome profiles, the cell lines were clearly separated into groups of luminal, basal, claudin-low, and nonmalignant subtypes. FIG. 14 is a plot of the Spearman's rank correlation coefficient showing the clustering of the cell lines. Clusters of cancer cell line of luminal and basal subtypes were well separated. Clustering within the basal subtype cell lines revealed the known subgroups of claudin-low and non-malignant cell lines (MCF10A, MCF10F, MCF12A, and MCF10DCIS). A prior classification of ERBB2 overexpression was confirmed by the proteomics measurement. Similar clustering was observed when breast cancer cell lines were analyzed based on their messenger RNA expression.

The correlation of mRNA and protein levels in the studied cell lines was investigated further by using mRNA expression profiles generated by RNA sequencing for 36 of the studied cell lines. The median Spearman's rank correlation coefficient between proteome profiles from biological replicates of the same cell line was 0.82, confirming a high reproducibility of the multiplexed proteome quantification technology. The median correlation coefficient was 0.58 when comparing protein and mRNA profiles. This was slightly higher than the range of 0.2-0.3 reported in other studies. The correlation coefficients among all mRNA and protein level profiles from 36 cell lines were compared, and one association was defined for each profile with the best correlated profile.

Figure 15A:
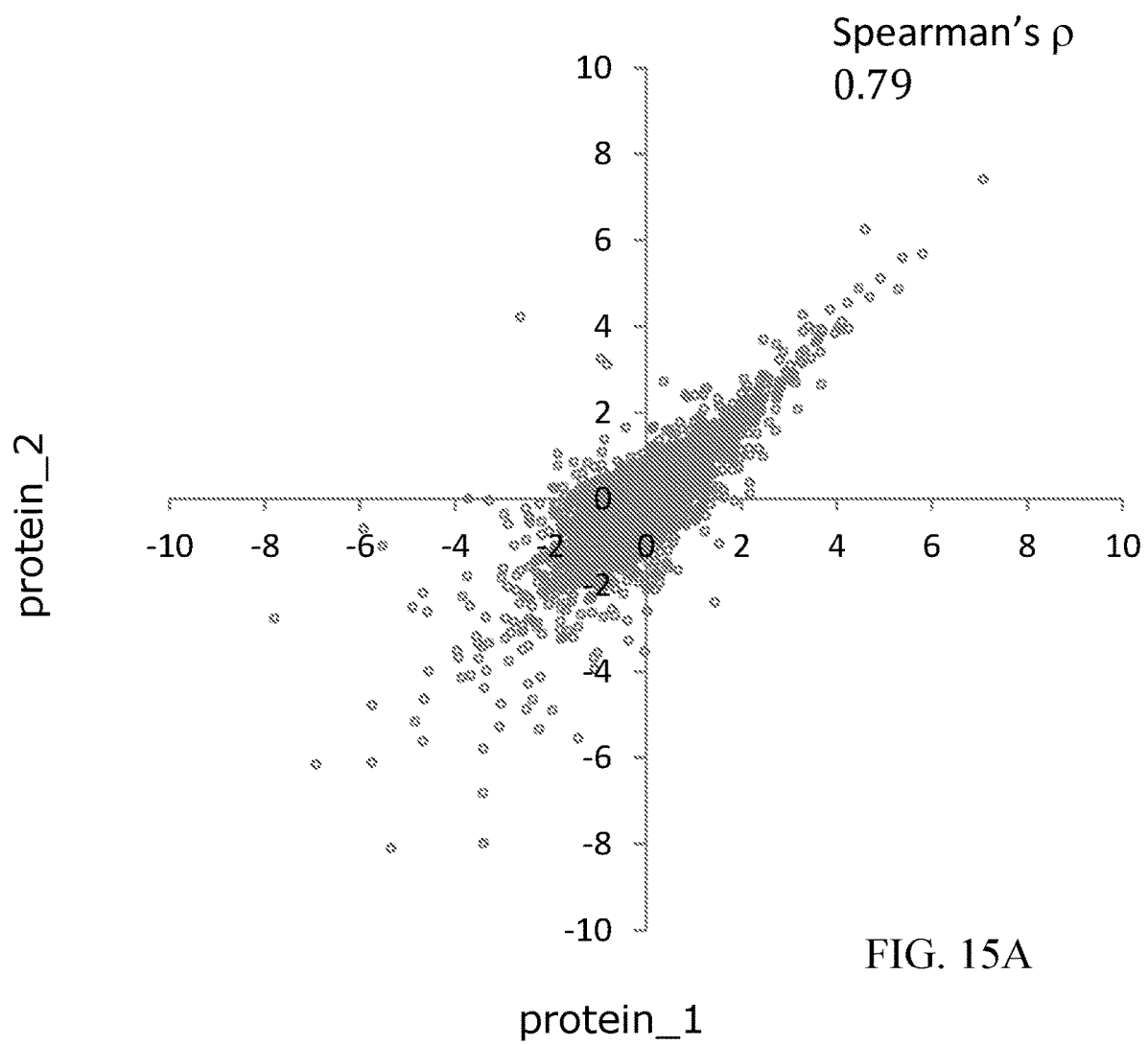
FIG. 15A is a scatter plot showing proteins levels measured in two biological replicates of HCC1937 proteomes.
Figure 15B:
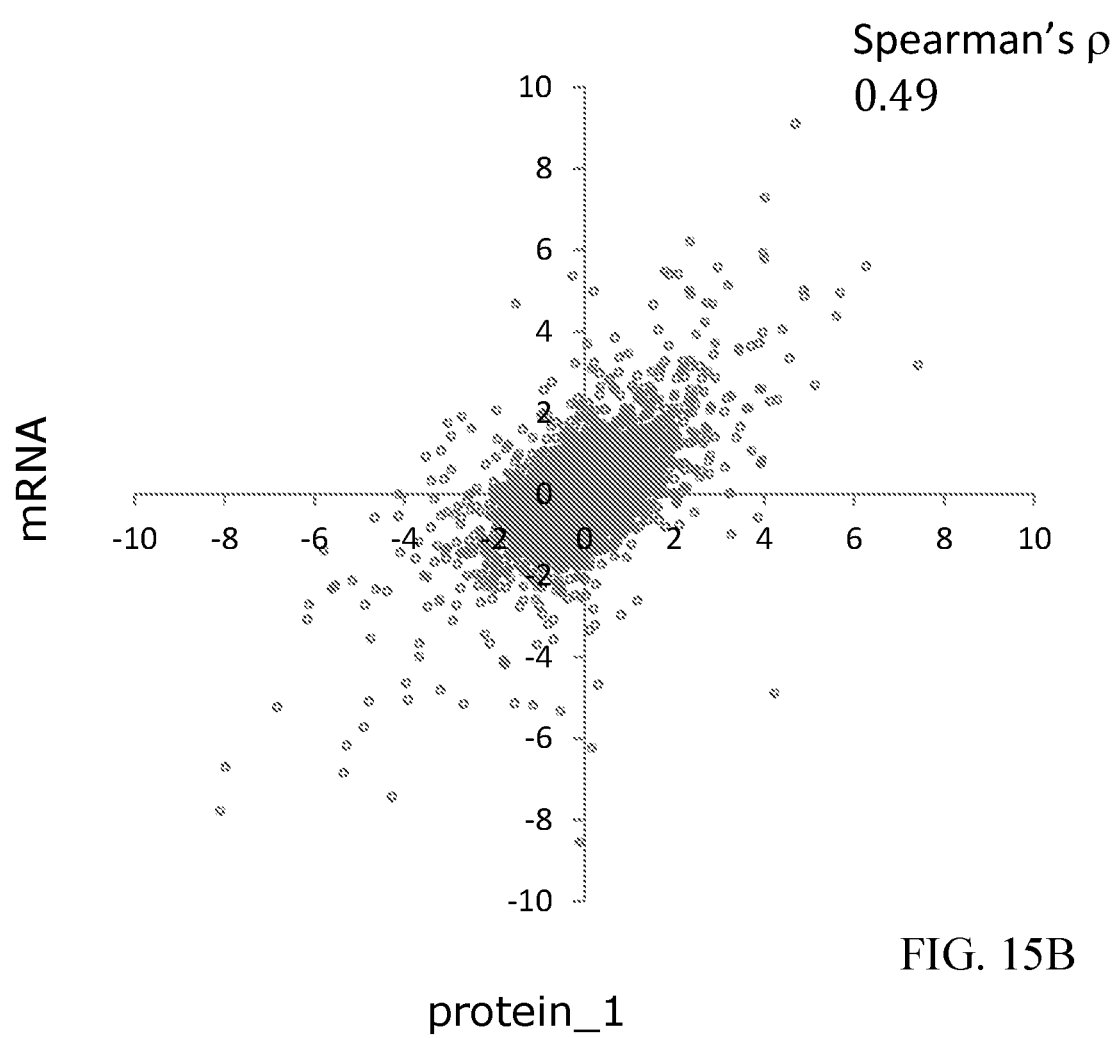
FIG. 15B is a scatter plot showing protein levels measured in one biological duplicate of the HCC1937 proteome against mRNA level measured by sequencing analysis.
Figure 15C:
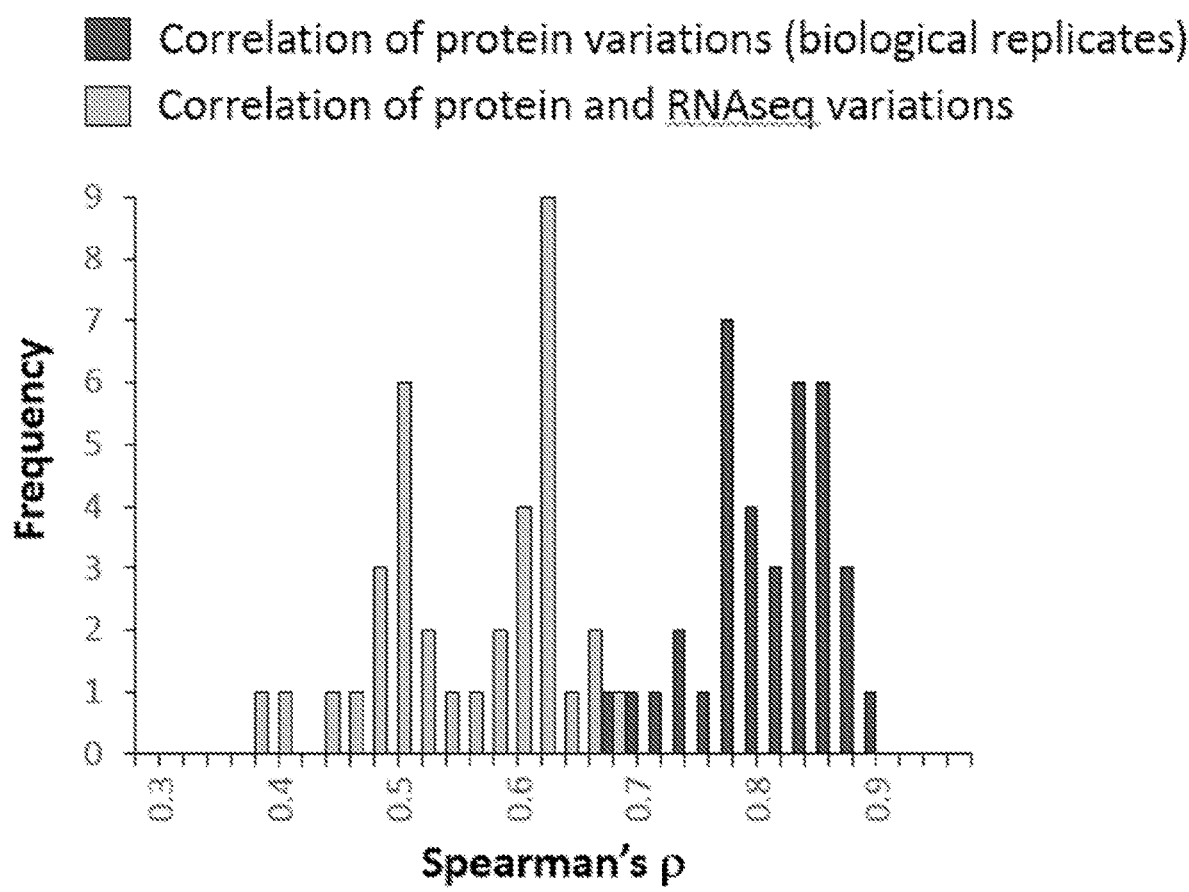
FIG. 15C is a chart showing the Spearman correlation coefficient distribution for duplicate proteomics measurements and for mRNA and protein level correlations.

FIG. 15A is a scatter plot showing protein levels measured in two biological replicates of HCC1937 proteomes. Protein levels were calculated as the log 2 ratio of the protein level determined in each duplicates over the median protein level in all proteome measurements (duplicates of 36 cell lines). FIG. 15B is a scatter plot showing protein levels measured in one biological duplicate versus mRNA level measured by RNA sequencing analysis. Both levels are given as log 2 HCC1937 intensity/median intensity. FIG. 15C is a bar chart showing the Spearman correlation coefficient distribution for duplicate proteomics measurements, and for mRNA and protein level comparisons.

Figure 15D:
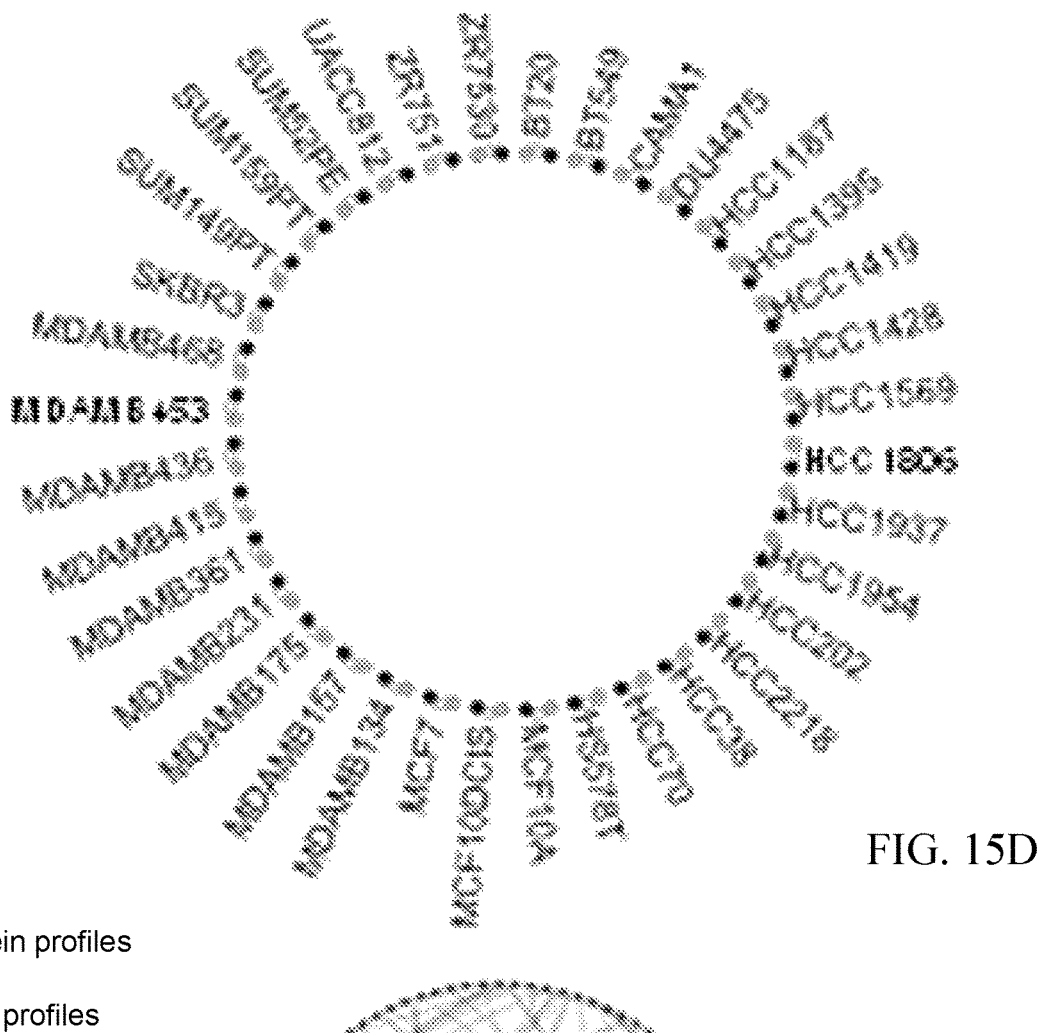
FIG. 15D is a radar chart showing top correlations between mRNA and proteome profiles for 36 cell lines.

Associations were found exclusively for mRNA and protein profiles from the same cell line. FIG. 15D is a radar chart showing top correlations (edges) between mRNA and proteome profiles across 36 cell lines.

Figure 15E:
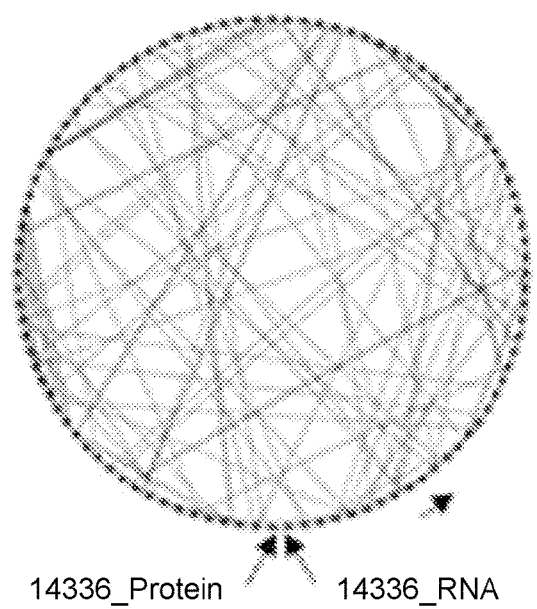
FIG. 15E is a chart showing top correlations between mRNA and proteins based on co-regulation profiles of the 100 most abundant gene products over 36 cell lines.

Associations between the relative concentration profiles of individual mRNA molecules and proteins were then analyzed across the 36 cell lines, which revealed an entirely different correlation pattern. Analyzing the profiles for the 100 most abundant gene products across the 36 cell lines— as determined by the average mRNA sequencing read counts from 36 cell lines—showed that only 78 of the 200 (39%) profile pairs with the highest Spearman correlation coefficient calculated interactions were a match of mRNA and protein encoded from the same gene. FIG. 15E is a chart showing top correlations (edges) between mRNA and proteins based on co-regulation profiles of the 100 most abundant gene products across the cell lines.

Figure 15F:
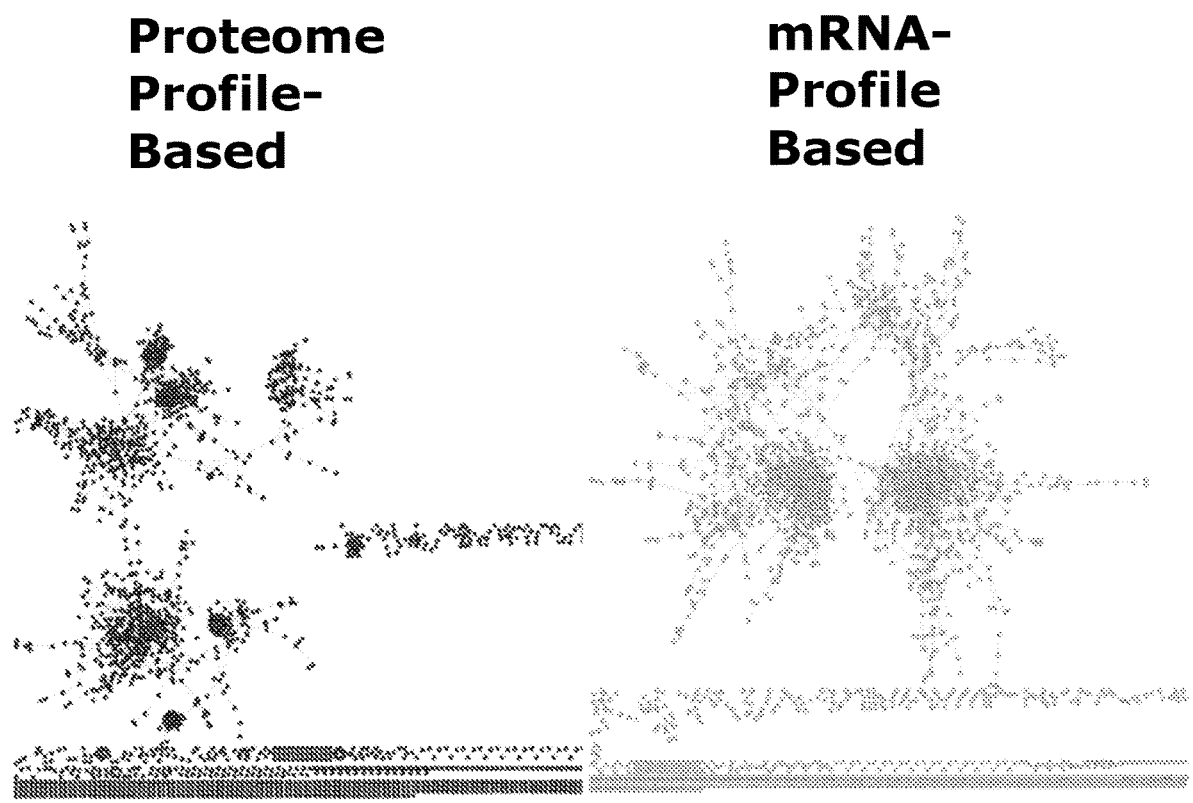
FIG. 15F is a set of plots showing identified associations among gene products based on proteome-based and mRNA-based analysis of multiple cell lines.

To further explore the differences of mRNA and protein co-regulation across the 36 cell lines the mRNA and protein datasets were analyzed to construct networks of significant interactions between gene products through calculating the Spearman's correlation coefficient for the profile of each pair of individual protein profiles as well as each pair of individual mRNA profiles across all cell lines for 6674 gene products for which we had data points in both datasets. A very strict filter of Benjamini-Hochberg (BH) corrected P value $\leq 5\times 10^{-4}$, and considering only positive correlations, revealed 5748 significant associations among 2494 mRNA molecules and 7086 associations among 2122 proteins. Surprisingly, only 431 significant associations between gene products encoded by the same gene were found in the overlap of both datasets (<8%), as shown in FIG. 15F.

The mRNA and protein derived association networks were analyzed for interactions that were also assigned as high-confidence interactions, with a score $\geq 0.700$ in the STRING database, a compendium of experimentally determined as well as predicted functional protein interactions. As a result, 2953 (42%) of the proteome-based associations were confirmed by known interactions in the STRING database, but only 250 (4%) of the associations derived from the mRNA dataset.

Figure 15G:
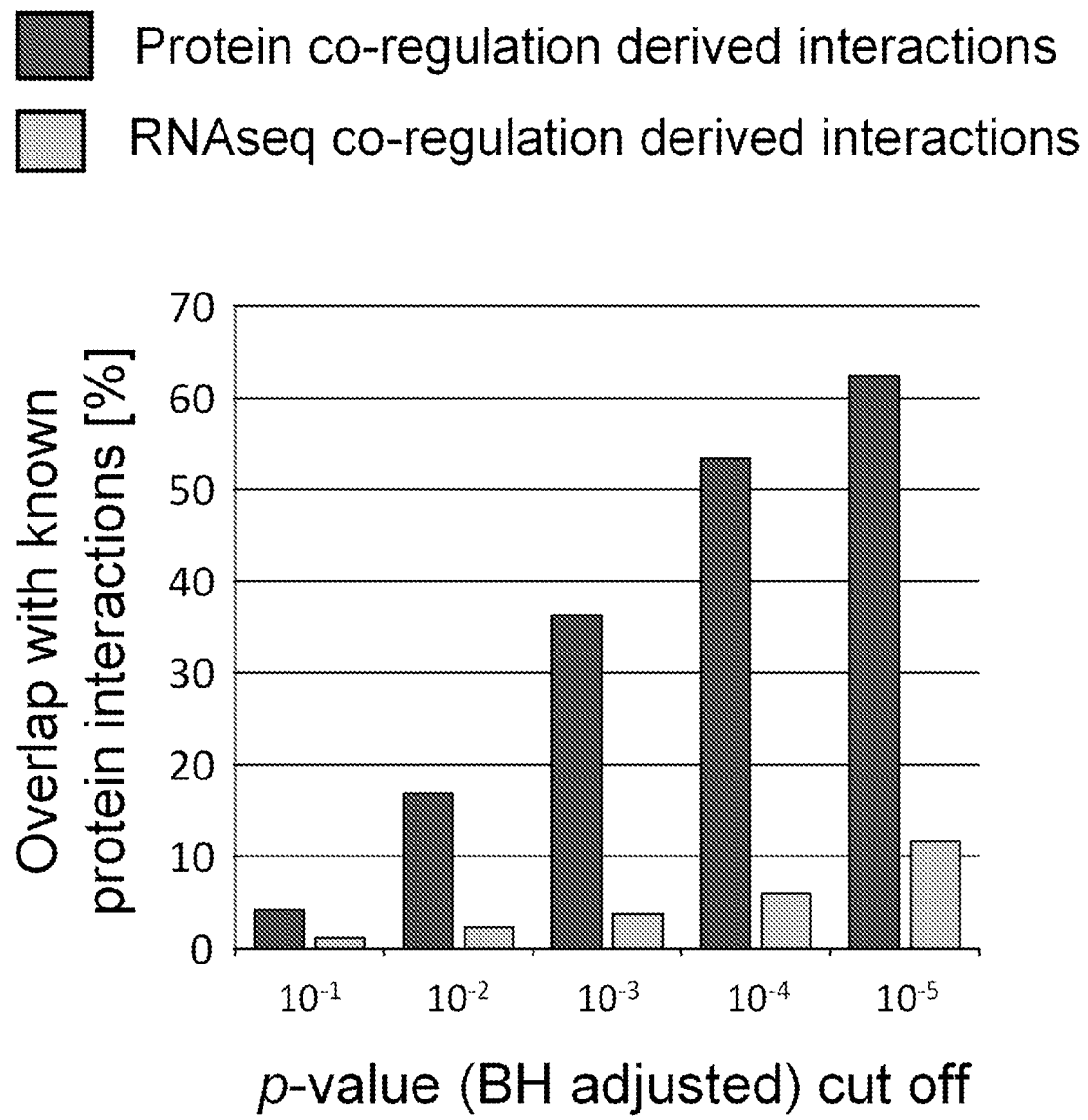
FIG. 15G is a chart showing overlap with known protein interactions for protein associations identified by proteome-based and mRNA-based analysis of multiple cell lines.

An increased relative number of known associations in the proteome derived dataset was confirmed for several precision thresholds. FIG. 15G is a bar chart showing overlap with known protein interactions for peptides in the STRING database. As shown in FIG. 15G, with the mRNA profile derived gene-association network, the protein profile-derived network identifies a substantially higher number of known functional high-confidence protein-protein interactions from the STRING database. The data shown in FIGS. 15A-15G indicate that co-regulation analysis applied on proteome profiles has a substantially higher predictive power to identify known functional protein-protein interactions than co-regulation analysis on transcriptome profiles.

Next, the proteome derived network of protein-protein interactions was characterized. Co-regulation analysis on the profiles from all 41 cell lines (the 36 lines considered above and an additional 5 for which mRNA data was not available) revealed 14909 associations among 3024 proteins (BH corrected $P \leq 5\times 10^{-4}$). The numbers of interaction for each protein (median=3) followed a power-law distribution, which is typically observed for social or biological networks. Inspection of the identified associations revealed a remarkable ability of co-regulation at the protein level to reveal well characterized multi-protein complexes such as the ribosome, proteasome, the nuclear pore complex, and the anaphase-promoting complex.

Figure 16:
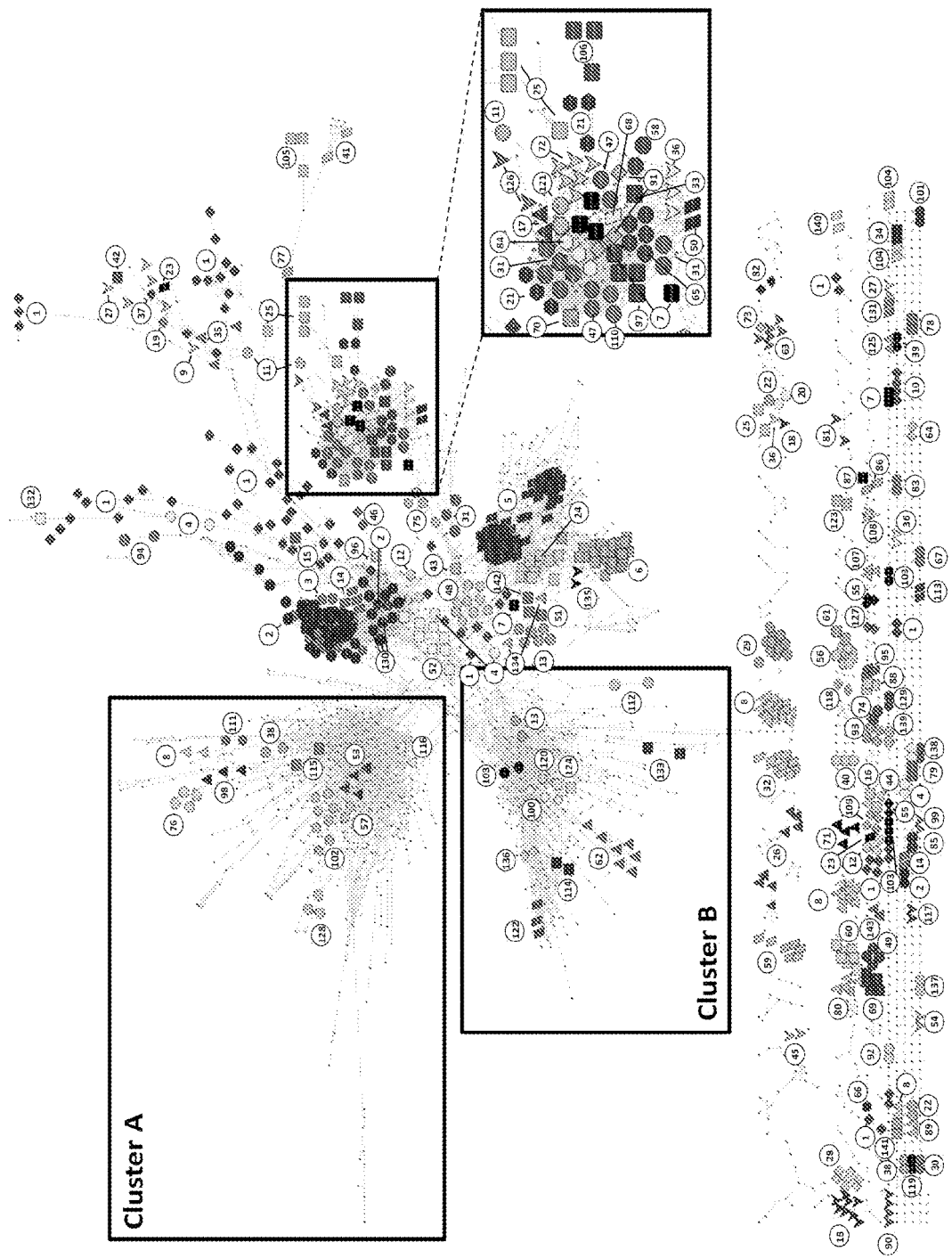
FIG. 16 is a schematic diagram showing a protein-protein association network derived from proteome-based analysis of multiple cell lines.

The correlation dataset for known physical protein-protein interactions was annotated, assigning 143 unique complexes from the Comprehensive Resource of Mammalian protein complexes (CORUM) database of high-confidence protein complexes. FIG. 16 is a plot of a protein-protein association network for the cell lines. The current version of the CORUM database comprises 1622 human multi-protein complexes (not including homomultimeric complexes). For 1222 of these, quantification of at least two components in all 41 cell lines was achieved, and for 506 (31% of the total number) of the partially redundant list of complexes, at least one association was identified between two complex components in the stringently filtered data set. The list was reduced to the above described 143 unique complexes when removing any redundancies by assigning each protein-protein association to only one complex. The median coverage of CORUM defined components in the complexes with associations observed in the data set was 67%. For 112 of the complexes, associations were identified between at least 90% of the components. This data shows that protein co-regulation analysis is an extremely powerful tool for detection of interactions of proteins in multi-protein complexes.

The entire protein-protein association network shown in FIG. 16 includes 14909 associations across 3024 proteins. Co-regulation was defined using the Spearman's correlation coefficient and a stringent filter of a Benjamini-Hochberg (BH) corrected P value $\leq 5\times 10^{-4}$ was applied to obtain the network. Only positive correlations are shown in the figure. The 143 complexes discussed above are labeled with an index number in FIG. 16. Two distinct clusters (A and B) in the network that are significantly enriched in membrane associated proteins comprise most of the novel interactions revealed by the analysis.

Of the 14909 protein-protein associations, 4179 (28%) were attributed to protein complexes defined in the CORUM database. The number of observed associations previously defined as high-confidence interactions in the STRING database was 5149 (35%) of which 3032 were overlapping with interactions defined by CORUM. The identification of 2117 STRING confirmed associations not defined in the CORUM database suggests that interactions detected through co-regulation are not restricted to stable interactions in multi-protein complexes.

To further examine if protein co-regulation analysis allows identification of functional protein-protein interactions outside of multi-protein complexes, 37 associations that were detected for cyclin dependent kinase 1 (CDK1) were examined further. From these associations 24 (62%) were high-confidence interactions in the STRING database. Of the remaining 13 associated proteins with no described direct CDK1 association in the STRING database, five had a STRING connection with one of the 24 STRING confirmed interactors. Only four of the 37 associated proteins—CCNB1, CCNB2, DPOE1, and DPOLA—are listed in the CORUM database as interacting with CDK1 in multiprotein complexes.

Another less stringent protein-protein interaction database, the BIOGRID database, was queried for proteins physically interacting with CDK1 as observed through yeast-two hybrid (Y2H) or protein affinity-purification followed by mass spectrometry (AP-MS) approaches. Three additional proteins from the CDK1 interacting set were identified: CEP55, CKS1, and EZH2. Thus while STRING confirmed most of the identified interactions, only 7 (19%) of the 34 proteins were previously shown to physically interact with CDK1. These results suggest that protein co-regulation is suitable to identify both stable physical interactions between proteins as well more distant but nevertheless functionally relevant interactions, potentially including transient physical associations.

Protein-protein association data obtained using the methods disclosed herein was compared to data derived from large-scale interactome screens using immunoaffinty-purification of proteins and identifying associated proteins by mass spectrometry (AP-MS). Both known and novel associations were confirmed by performing this comparison. Approximately 20% of the known and 6% of the novel associations identified were confirmed in the AP-MS based dataset when only considering associations where both proteins were identified in both studies. Comparing another large-scale AP-MS dataset in the same manner showed a similar overlap: 22% for known and 4% for novel associations.

In sum, high-confidence protein-protein associations from the CORUM and the STRING databases confirm 6296 (4%) of the 14909 interactions and 8613 (58%) associations in this stringently filtered dataset have yet not been reported. Supporting the validity of these novel interactions, 3636 of them were found to link proteins with STRING confirmed interactions to other proteins detected to be associated with one of the two proteins. Most (3835) of the remaining 5563 novel associations not falling in either category were located in two distinct clusters of the protein association network, which are labeled as clusters A and B in FIG. 16.

Clusters A and B were found to be highly enriched for membrane bound proteins based on Gene Ontology (GO) category analysis on the 599 proteins in cluster A and 398 proteins in cluster B through the use of DAVID (as described, for example, in Huang et al., "Bioinformatics enrichment tools: paths toward the comprehensive functional analysis of large gene lists," *Nucleic Acids Res.* 37: 1-13 (2009)). Cluster A was also enriched for protein from the golgi apparatus and vesicles while proteins in cluster B were enriched for plasma membrane associated proteins as well as the cytoskeleton. Thus most novel and entirely unmapped interactions identified correspond to interactions that are known to be poorly captured by the two most widely used technologies applied to interactome studies: Y2H32 and AP-MS33.

Figures 17A, 17B, 17C:
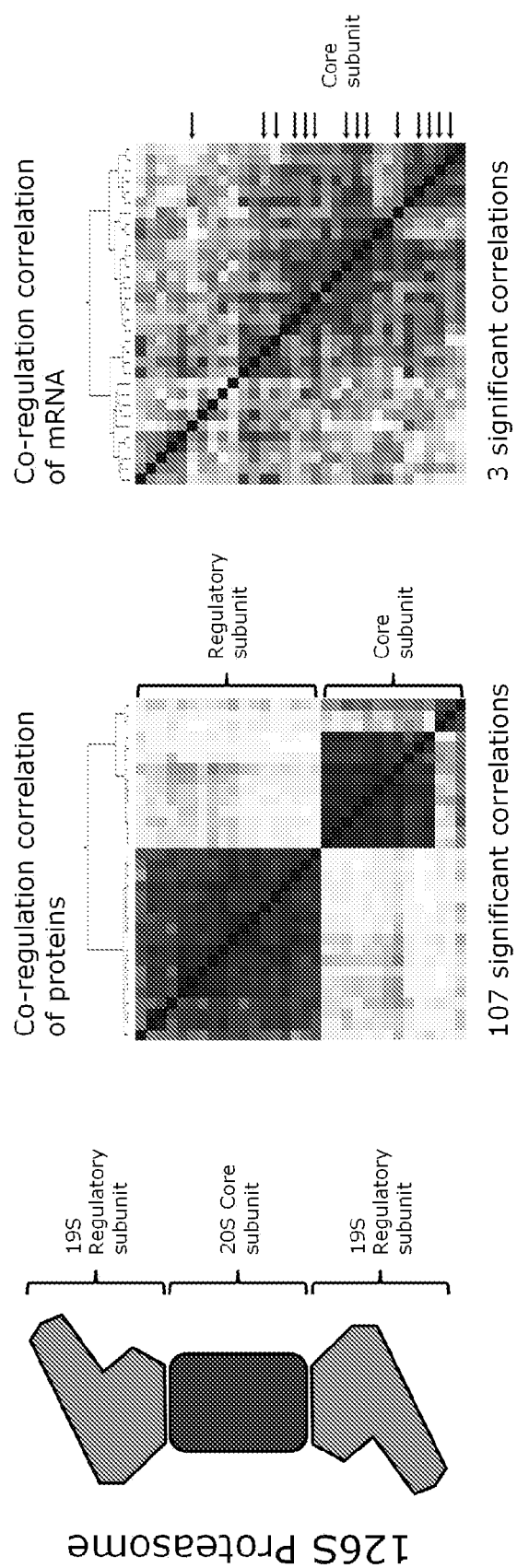
FIG. 17A is a schematic diagram of the 26S proteasome multi-protein complex.
FIG. 17B is a plot showing protein-protein associations among members of the 26S proteasome multi-protein complex, derived from proteome-based analysis.
FIG. 17C is a plot showing protein-protein associations among members of the 26S proteasome multi-protein complex, derived from mRNA-based analysis.

It was observed that gene product association networks derived from mRNA and protein co-regulation analysis differ substantially, as shown in FIG. 15E. A striking example of this divergence is given by the Spearman correlation matrices of protein and mRNA profiles of 32 members of the well-studied 26S proteasome multi-protein complex shown schematically in FIG. 17A. While the association network derived from the proteome profiles contained 107 high-confidence associations between members of the complex and revealed two distinct clusters for the 20S core and 19S regulatory subunits, as shown in the plot of FIG. 17B, the mRNA levels derived network contained only three associations between proteasome members and did not reveal the complex's substructure, as shown in the plot of FIG. 17C.

Figures 17D, 17E:
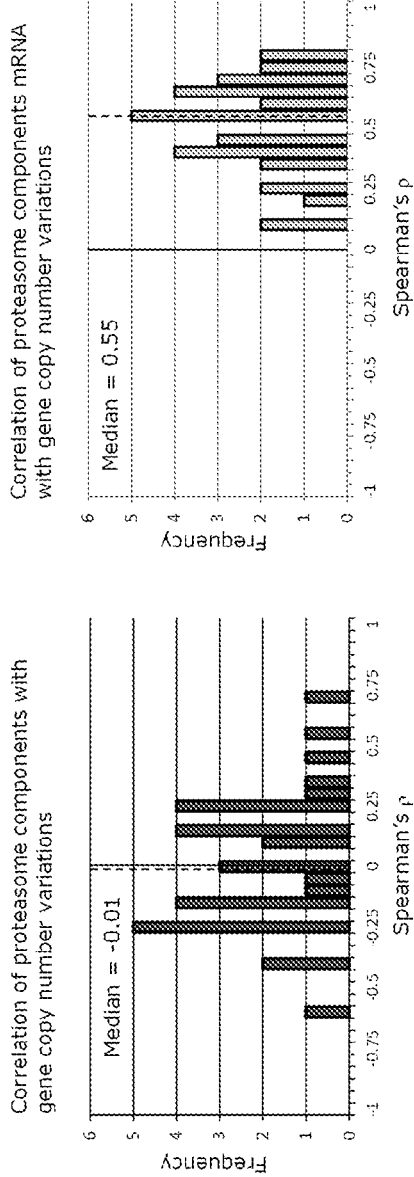
FIG. 17D is a plot showing a distribution of correlations between proteasome profiles with gene copy number variations for the 26S proteasome multi-protein complex.
FIG. 17E is a plot showing a distribution of correlations between mRNA profiles with gene copy number variations for the 26S proteasome multi-protein complex.

It was recently shown that mRNA profiles and gene copy number variations (CNV) are highly correlated while protein profiles and CNVs are not. To assess if a similar effect may underlie the differences between mRNA and proteome in our data, the Spearman's rank correlation coefficient was determined between mRNA profiles and CNVs as well as protein profiles and CNV for 19 cell lines, which CNVs were accessible through the canSAR knowledge-base (available at http://www.cansar.icr.ac.uk). FIGS. 17D and 17E are histograms showing values of the Spearman's rank correlation coefficient between protein profiles and CNV (FIG. 17D) and between mRNA profiles and CNV (FIG. 17E). A high correlation was observed between mRNA profiles and CNV (median $\rho=0.55$), with no correlation between protein levels and CNVs (median $\rho=-0.01$).

Figures 17F, 17G:
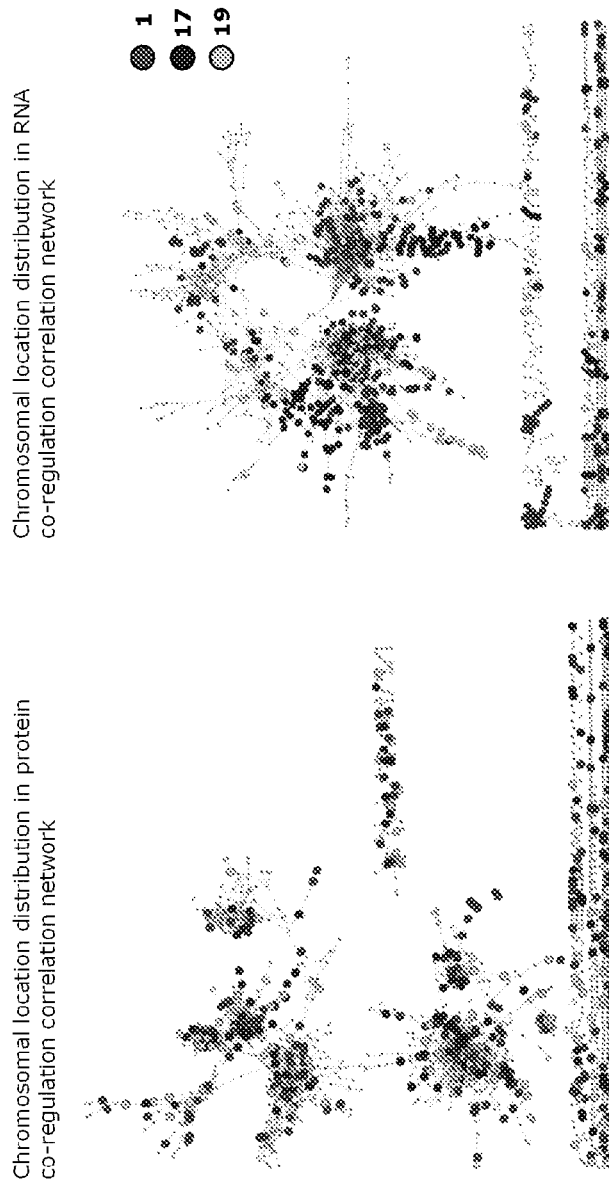
FIG. 17F is a schematic diagram showing chromosomal location distribution within a protein co-regulation correlation network.
FIG. 17G is a schematic diagram showing chromosomal location distribution within a mRNA co-regulation correlation network.

Further evidence for the network of mRNA co-regulation derived network to be influenced by CNVs or possibly by other co-regulation mechanism of neighboring genomic loci at a high degree was found through monitoring chromosomal locations of associated gene products. For the mRNA derived network, 33% of the associations were between genes encoded from the same chromosome, while this proportion was 9% for the proteome derived network. FIGS. 17F and 17G are plots showing the chromosomal location distributions of gene products for the protein- and mRNA-derived networks, respectively. In the figures, only the three chromosomes encoding for most of the gene products in the datasets are shown for clarity.

These results indicate that gene copy number variations strongly affect mRNA levels, which may contribute to the limited applicability of mRNA co-regulation analysis to determine functional relations between expressed genes. The data suggests that under the pressure of these functional relations, protein levels are adjusted post-transcriptionally.

It should be noted that while correlations among pairs of proteins were identified based on values of the Spearman's rank correlation coefficient as described above, correlations among protein pairs can also be identified using other methods. In some embodiments, for example, correlations can be identified by calculating values of the Pearson correlation coefficient, and applying a suitable filtering and/or thresholding condition to separate correlated pairs of proteins from protein pairs that are not correlated.

More generally, any technique which permits correlations among candidate pairs of proteins to be reliably identified and distinguished from pairs of proteins that are not correlated can be used in connection with the methods described herein. The methods described above and subsequently are suitably general such that they can accommodate a wide variety of different techniques for distinguishing correlated proteins from uncorrelated proteins.

The foregoing results demonstrate that protein co-regulation analysis on breast cancer cell line proteome data allows the characterization of physical and functional protein-protein interactions and that this information is not accessible through mRNA profiles from the same cell lines. It is believed that these findings have two important implications. First, the results suggest a regulatory mechanism that adjusts protein levels extremely accurately according to their functional interactions. Studies on the effects of aneuploidy in yeast and human cell lines have shown that proteins which concentration is unaffected by duplication of the encoding chromosome are those of multi-protein complexes and that the attenuation of their concentration is regulated through protein degradation. This implicates that accurately regulated protein degradation is adjusting protein concentration in accordance to the functional network, which corroborates with hypotheses that members of multi-protein complexes are degraded at a higher rate if not imbedded into their cognate complex. The second implication is that quantitative proteomics is a powerful tool to characterize functional protein-protein interactions. Analysis of the dynamics of interactions at a proteome-wide level can be performed at an extremely high-throughput, by identifying protein-protein associations through protein co-regulation analysis of profiles from two different sets of samples to reveal differences of the interaction networks between these sets. Furthermore, when a network has been established from analyzing a set of profiles, deviations within this network can be characterized by monitoring the relative protein concentration changes of associated proteins.

Protein-Protein Interaction Deregulation

Proteome maps obtained across multiple samples (i.e., multiple cell lines) provide a rich data set for further investigation of interaction deregulation among associated proteins. As discussed above, the methods disclosed herein permit relatively rapid mapping of protein expression and concentration levels across individual cell lines. At present, a comprehensive proteome map can be obtained for a single cell line in approximately 4.5 hours, with an average of 9,115 proteins quantified.

Figure 18A:
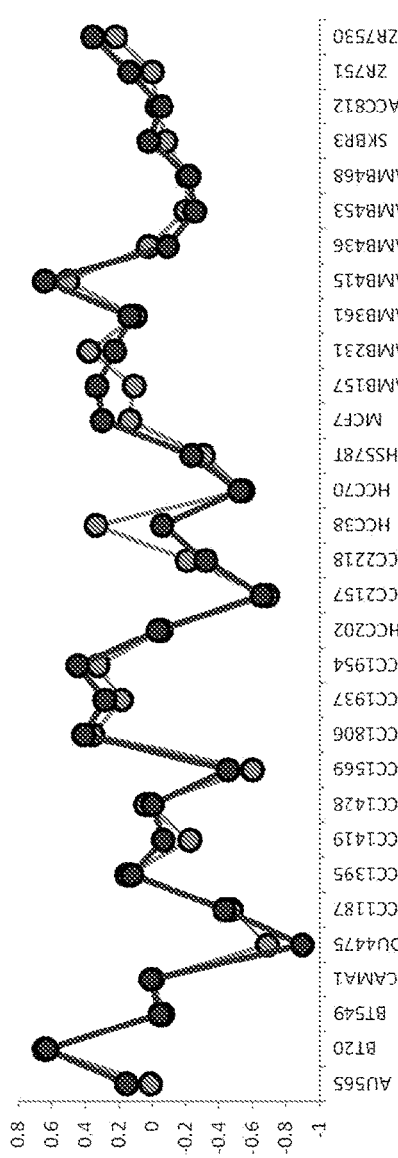
FIG. 18A is a plot showing relative concentration levels of proteins PSA1 and PSA3 in 31 cell lines.

Potential interactions can be identified by examining gene products across multiple cell lines in a protein network. FIG. 18A is a plot showing relative concentration levels of proteins PSA1 and PSA3 across 31 cell lines, shown on the horizontal axis. The relative concentration levels of these proteins are well matched, with a Spearman's correlation coefficient $\rho=1$. This high correlation suggests potential co-regulation between these proteins.

Figure 18B:
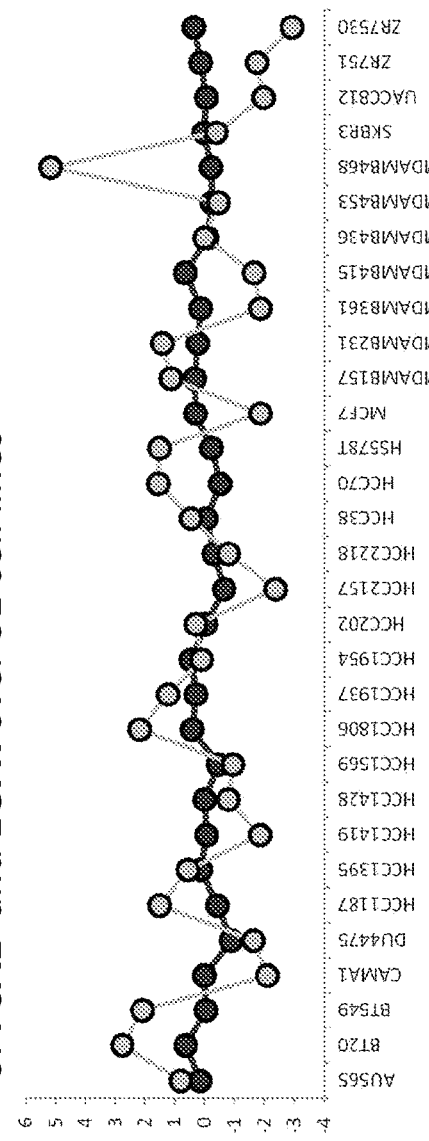
FIG. 18B is a plot showing relative concentration levels of proteins PSA1 and EGFR in 31 cell lines.

In contrast, FIG. 18B is a plot showing relative concentration levels of proteins PSA1 and EGFR across the same 31 cell lines. The relative concentration levels of these proteins diverge significantly in many lines. The relatively low Spearman's correlation coefficient $\rho=0.05$ for these protein concentrations suggests that functional interaction between them is unlikely.

Figure 19:
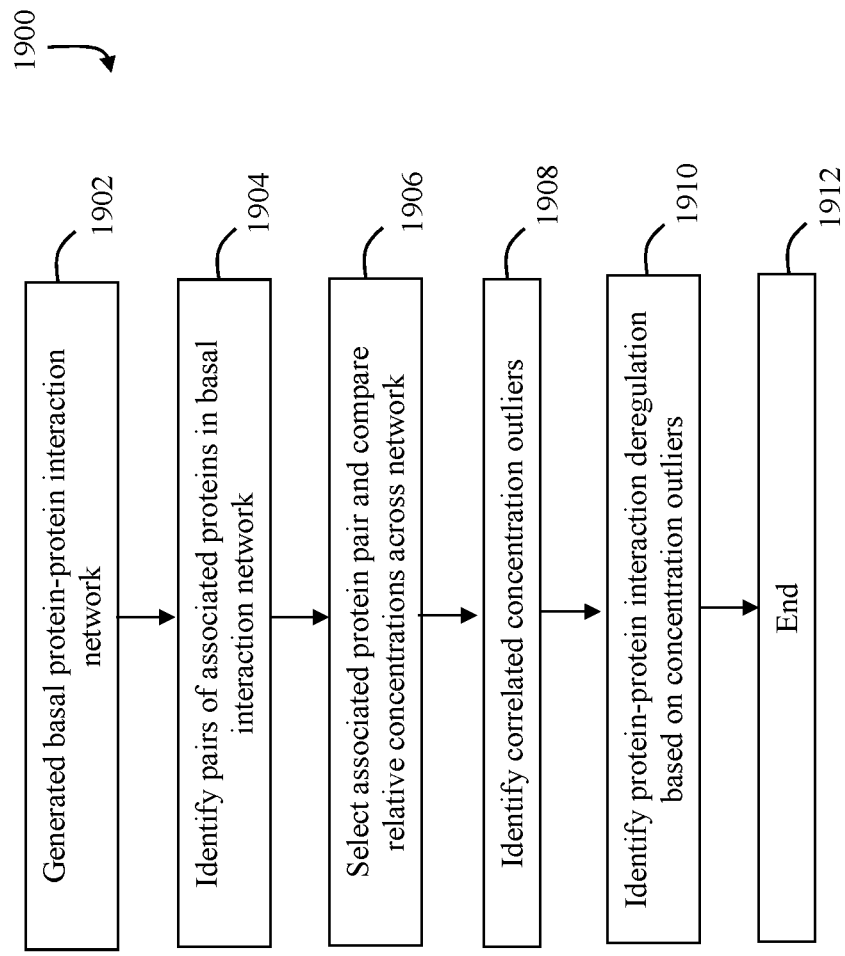
FIG. 19 is a flow chart showing a series of steps for identifying protein-protein interaction deregulation within a protein-protein interaction network.

FIG. 19 is a flow chart 1900 that includes a series of steps for identifying interactome (i.e., protein-protein) deregulation in a protein-protein interaction network. In a first step 1902, a basal protein-protein interaction network is generated. Generation of the network involves identifying and quantifying proteins expressed across one or more samples (i.e., cell lines) using the methods disclosed above involving mass spectral analysis. Dual fragmentation methods can be used to increase the number of proteins detected and quantified during the analysis.

After the basal network has been acquired, pairs of associated, interacting (i.e., co-regulating) proteins can be identified in step 1904. A variety of criteria can be used to identify associated proteins. For example, referring to FIGS. 18A and 18B, in some embodiments, relative concentration levels of two pairs of proteins across all samples in the basal network can be compared and a correlation metric, such as the Spearman's correlation coefficient, can be calculated. If the correlation metric exceeds a threshold value, the pair of proteins are deemed to be associated. If the correlation metric does not exceed the threshold value, any association between the pair of proteins is regarded as too weak to be of significance.

Figure 20:
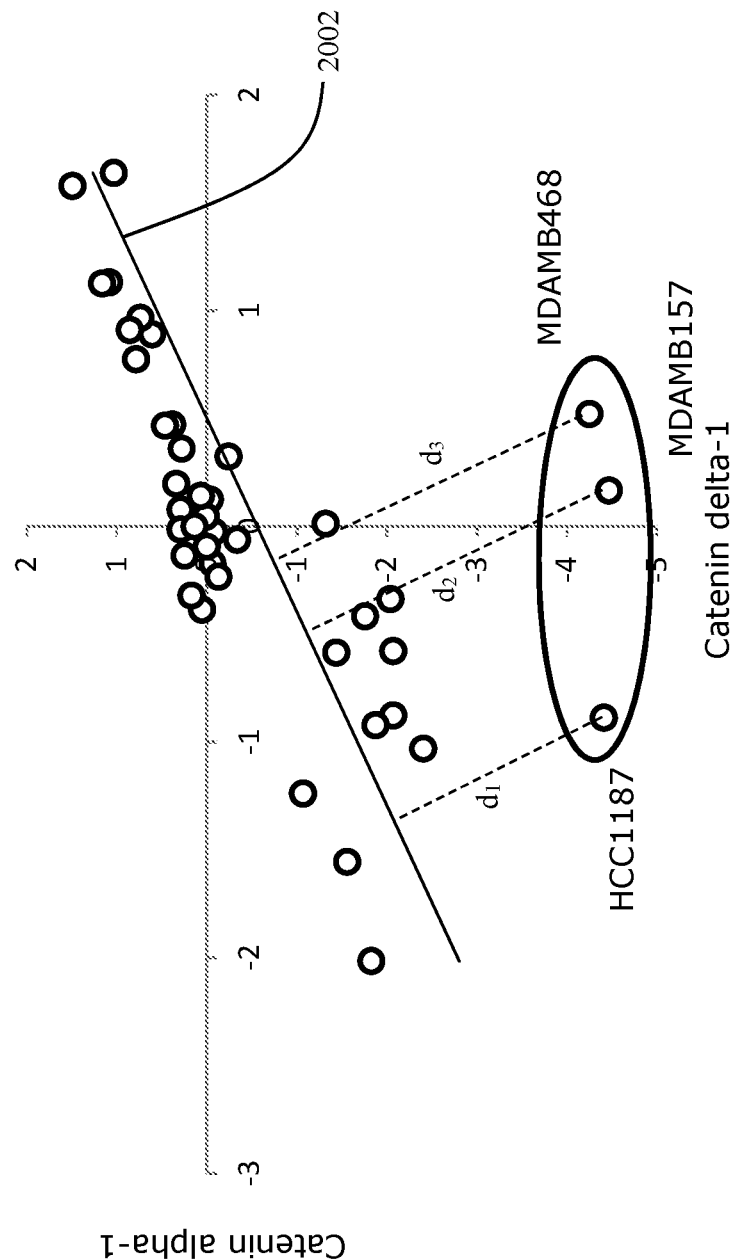
FIG. 20 is a plot of correlated relative concentration levels of proteins catenin delta-1 and catenin alpha-1 across 41 cell lines.

Next, in step 1906, an associated protein pair is selected, and the correlation between relative concentrations of each of the proteins across the basal network is compared. FIG. 20 is a plot showing an example of such a comparison. In the plot, relative concentrations of catenin delta-1 and catenin alpha-1 are compared for all 41 cell lines in the basal network of FIG. 16. Each point in the plot of FIG. 20 represents a different one of the cell lines, and the location of the point reflects the relative concentrations of catenin delta-1 and catenin alpha-1 in that cell line.

As part of the comparison between the relative concentrations, correlated concentration outliers are identified in step 1908. In FIG. 20, there are three outliers, corresponding to cell lines HCC1187, MDAMB468, and MDAMB157. A variety of different methods can be used to identify correlated concentration outliers. For example, in some embodiments, a line of best fit, shown in FIG. 20 as line 2002, can be computed for the correlated concentration values. A particular correlated concentration data point can be deemed an outlier if the closest distance from the point to the line of best fit exceeds a threshold value. In FIG. 20, for a threshold value $d_t$, the points representing cell lines HCC1187, MDAMB157, and MDAMB468 are outliers as their closest distances to line 2002 ($d_1$, $d_2$, and $d_3$, respectively) each exceed $d_t$.

In certain embodiments, correlated concentration outliers can be detected on the basis of the Mahalanobis distance. For example, to determine whether a particular correlated concentration data point represents an outlier, a mean value, centroid value, or other quantity representing a "center" or, more generally, a reference point for the distribution of correlated concentration data points for the distribution of correlated concentration data points can be computed. Then, for each correlated concentration data point, the bivariate outlier analysis involves determining the point's Mahalanobis distance from the center/reference point for the distribution. Next, the Grubbs test (e.g., $P \leq 1$) can be used to identify individual outliers among the individual correlated concentration data points based on each point's Mahalanobis distance.

It should be appreciated that other methods can also be used to identify correlated concentration outliers. For example, methods involving clustering analysis, nonlinear regression, principal components, and a variety of other techniques can also be used.

With correlated concentration outliers identified, protein-protein interaction deregulations can be identified in step 1910. Typically, such deregulations are due to specific mutations in the cell lines or samples to which the outliers correspond. For example, interaction deregulation between catenin delta-1 and catenin alpha-1 occurs due to a CTNA1 mutation in the HCC1187 cell line, and due to CTND2 and CTNNBL1 mutations in the MDAMB157 cell line. Other interaction deregulations can also readily be identified between other proteins once the basal protein-protein interaction network has been characterized. An entire global mapping of such deregulations can be achieved across an individual cell line in a few hours, after which the process in FIG. 19 terminates at step 1912.

Figure 21:
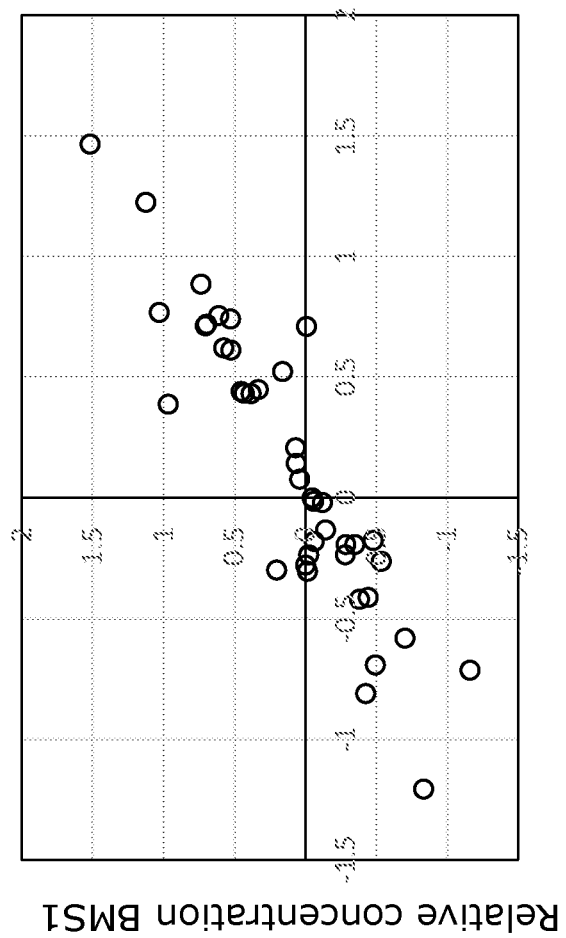
FIG. 21 is a plot of correlated relative concentration levels of proteins MPP10 and BMS1 across 41 cell lines.

Using the general methods shown in FIG. 19, a wide variety of different interaction deregulation events can be uncovered through analysis of protein-protein interaction networks. Moreover, the absence of correlation outliers between pairs of proteins is indicative of co-regulation across an entire basal network. FIG. 21 shows a plot of correlations between relative concentrations of proteins MPP10 and BMS1 across the 41 cell lines of the basal network shown in FIG. 16. Proteins MPP10 and BMS1 exhibit co-regulation across the network, with a Pearson's correlation coefficient of 0.91. These proteins are known to be involved in the assembly of ribosomal subunits in the nucleolus. No correlated concentration outliers are evident in FIG. 21, suggesting that these proteins remain co-regulated.

To explore how differences in protein network across cell lines can inform the biology of breast cancer models, cell line specific protein network dysregulation was investigated. Deviations from co-regulation across the 14909 significant correlated protein pairs identified using the 41-cell line dataset were examined. Bivariate outlier testing was performed on each protein pair based on first the Mahalanobis distance followed by the Grubbs test to determine outliers ($p \leq 0.1$) corresponding to cell lines with a putative deregulated protein pair.

Figure 22A:
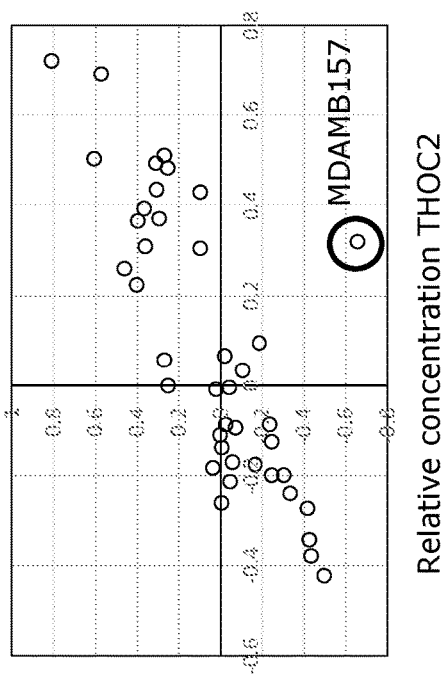
FIG. 22A is a plot of correlated relative concentration levels of proteins THOC2 and THOC1, derived from proteome-based analysis of 41 cell lines.

FIG. 22A is a plot showing correlated relative concentrations of proteins THOC2 and THOC1 across the 41 cell lines of the basal interaction network of FIG. 16. The Pearson's correlation coefficient for these two proteins is 0.78, suggesting co-regulation, but an outlier is present, corresponding to the MDAMB157 cell line. The presence of this correlated concentration outlier corresponds to interaction deregulation between THOC1 and THOC2 in the MDAMB157 cell line.

Figure 22B:
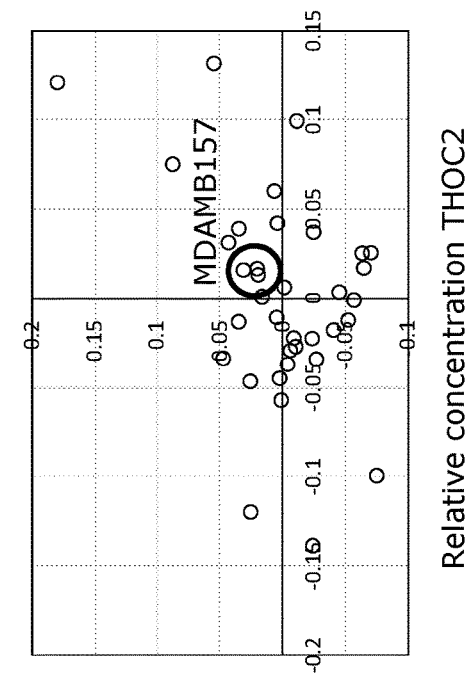
FIG. 22B is a plot of correlated relative concentration levels of proteins THOC2 and THOC1, derived from mRNA-based analysis of the same 41 cell lines.

FIG. 22B is a plot showing correlated relative concentrations of proteins THOC2 and THOC1 derived from mRNA expression analysis. The data point corresponding to the MDAMB157 cell line is shown in FIG. 22B and is not an outlier, demonstrating that deregulation of the association between THOC1 and THOC2 in the MDAMB157 cell line is not revealed by mRNA analysis.

THOC1 and THOC2 are components of the TREX complex involved in the regulation of transcription, mRNA processing, and export. THOC2 carries a mutation (R1307 W) in this cell line, which could underlie this effect by inhibiting the binding between THOC1 and THOC2 leading to degradation of THOC1. Consistent with protein level regulation rather than a change in mRNA levels, mRNA co-regulation analysis did not identify MDAMB157 as an outlier.

Figure 23:
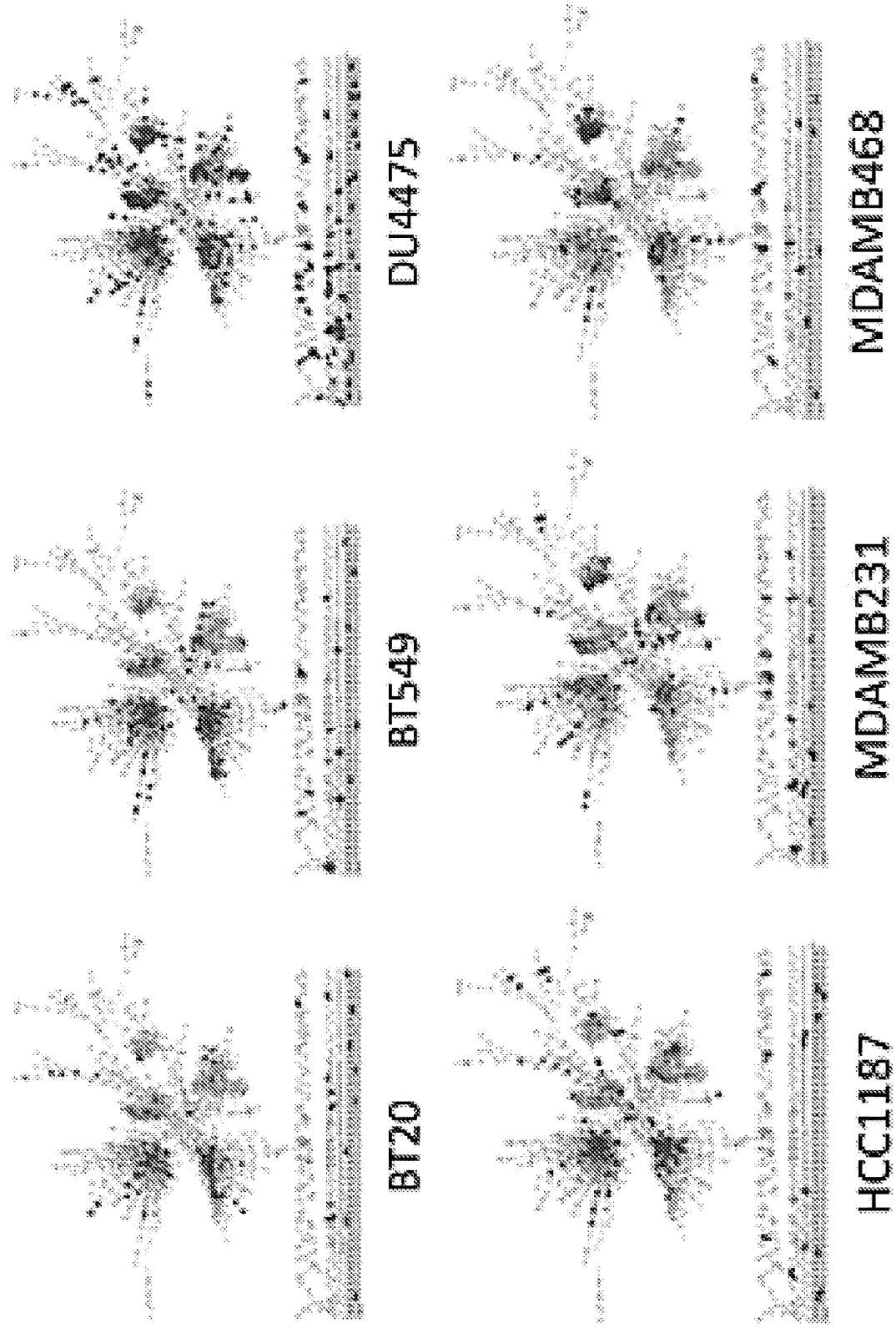
FIGS. 23 and 24 are plots showing dysregulated protein-protein association networks in basal and luminal subtype breast cancer cell lines, respectively.
Figure 23:
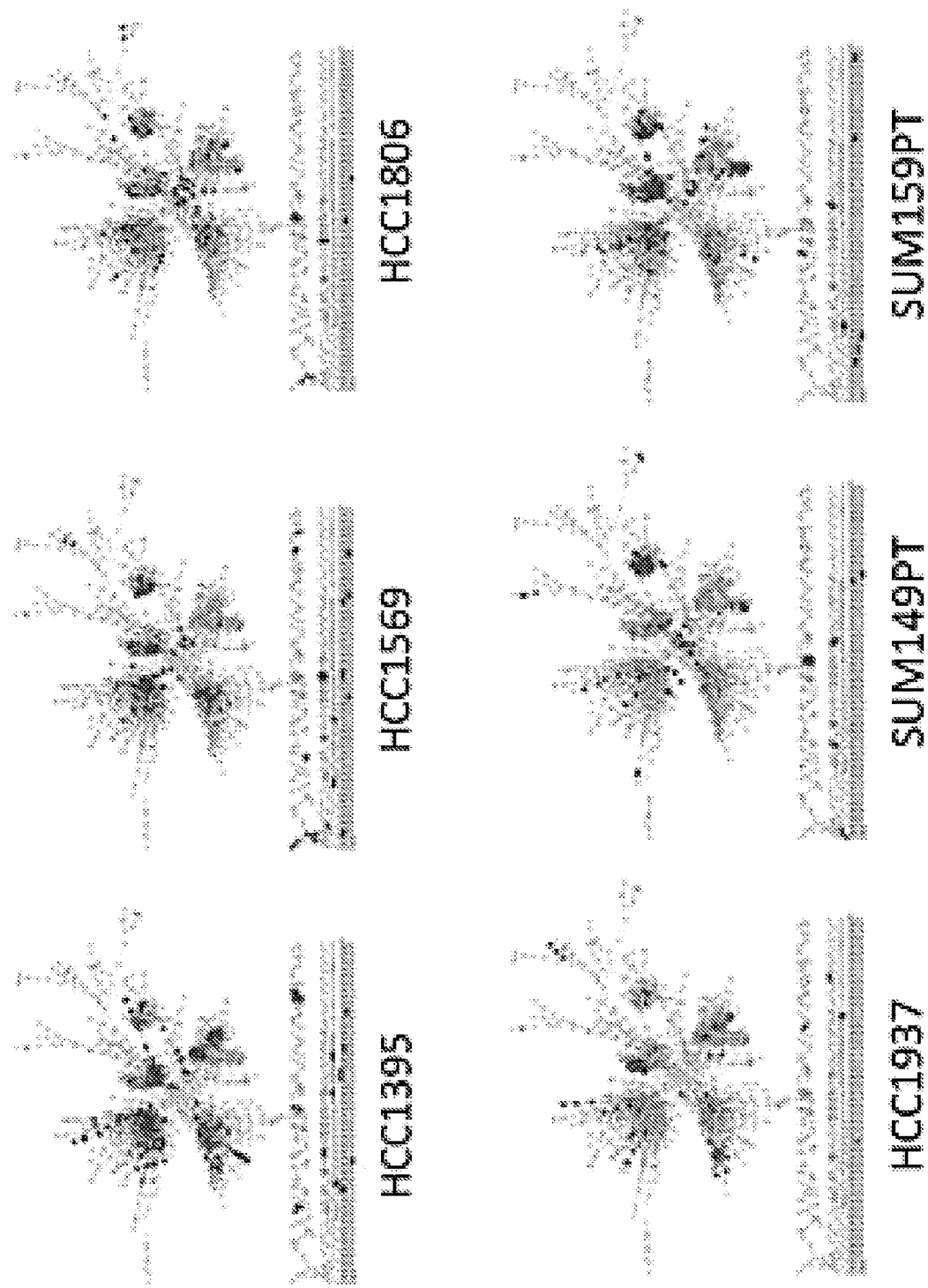
Figure 23:
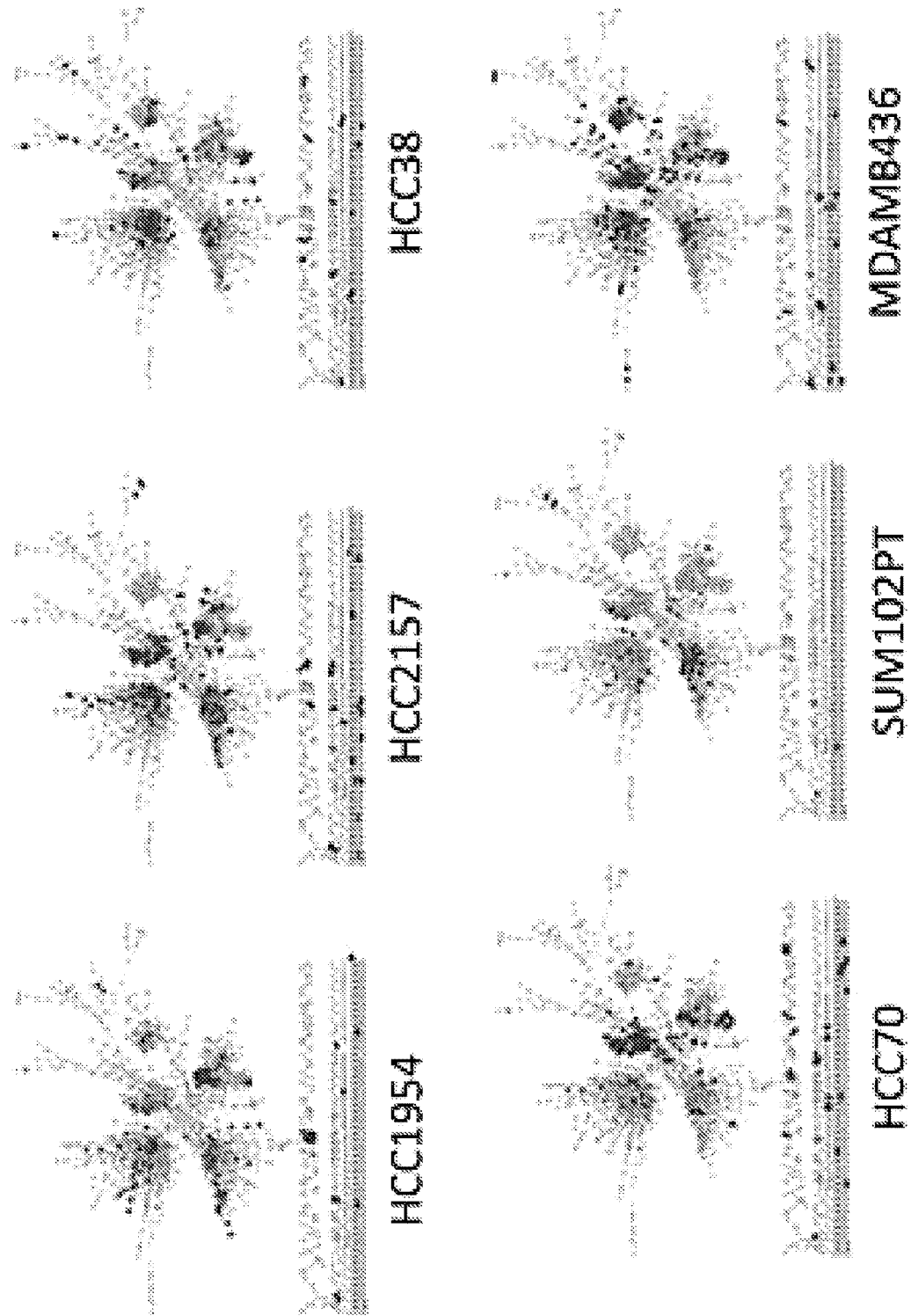
Figure 23:
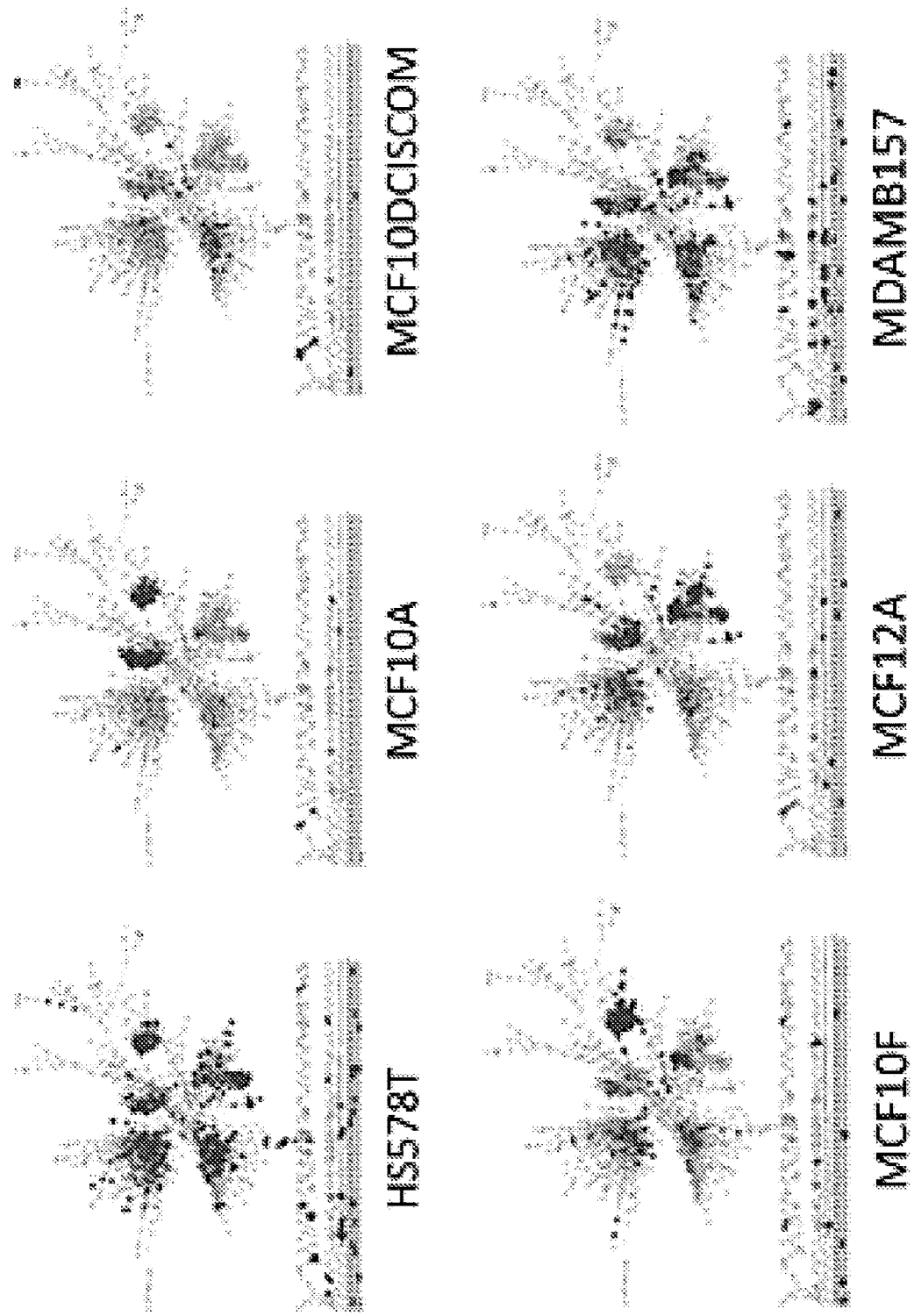
Figure 24:
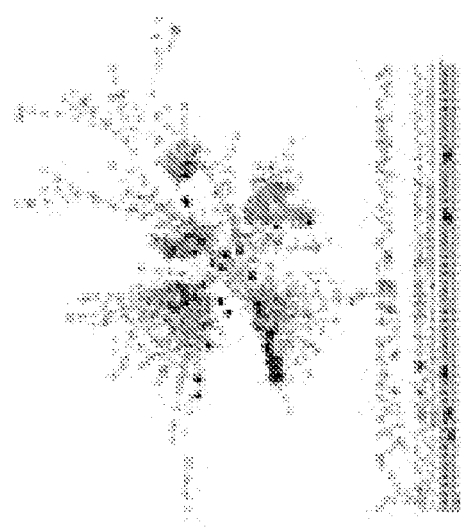
Figure 24:
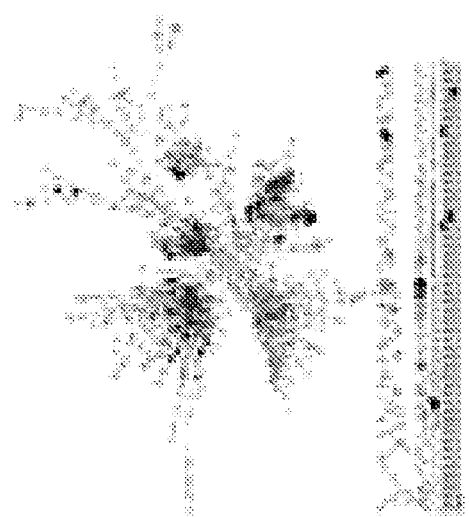
Figure 24:
Figure 24:
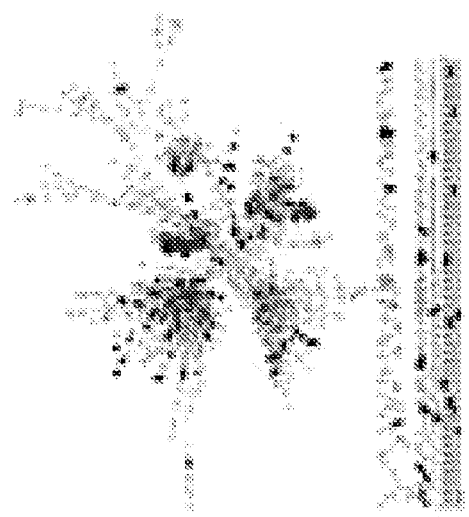
Figure 24:
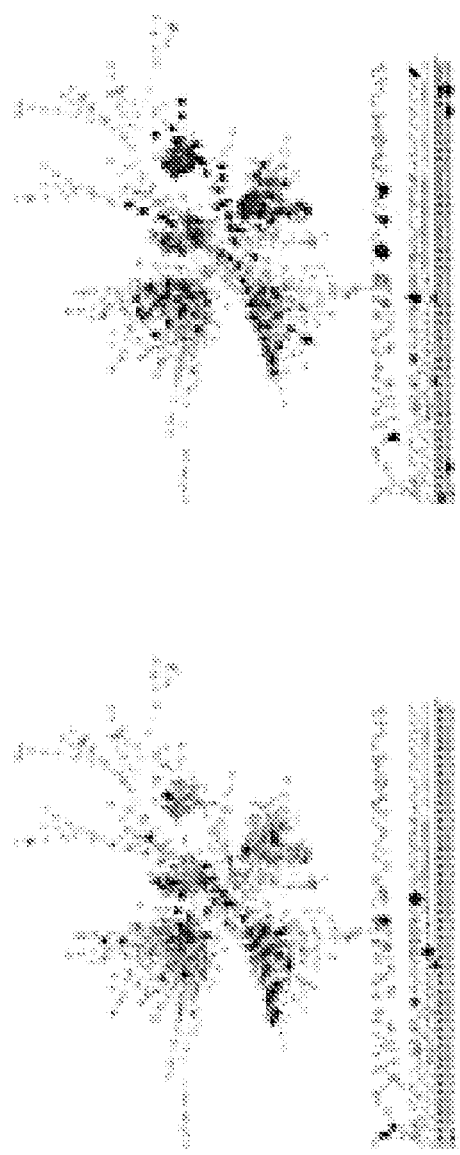
Figure 24:
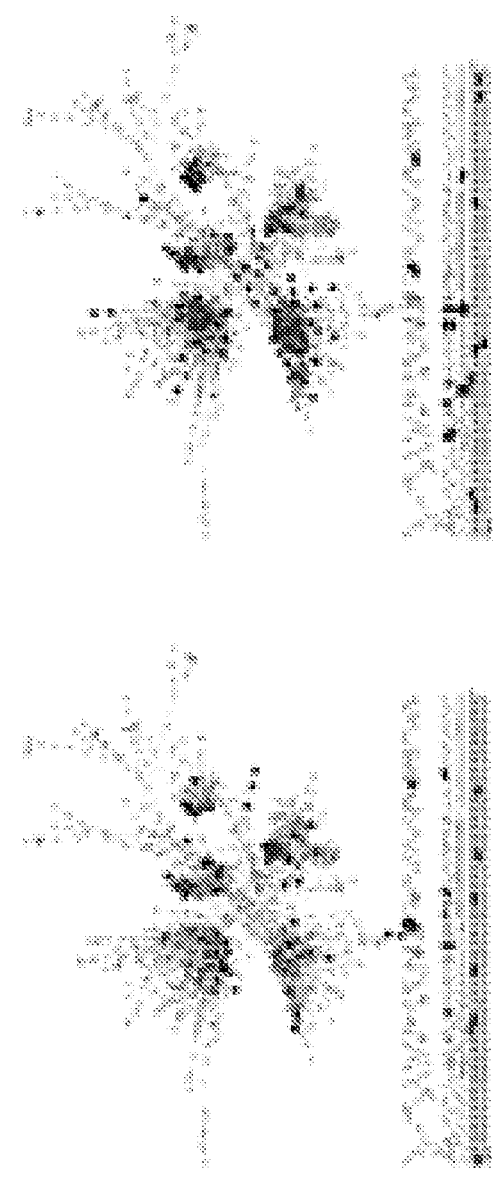
Figure 24:
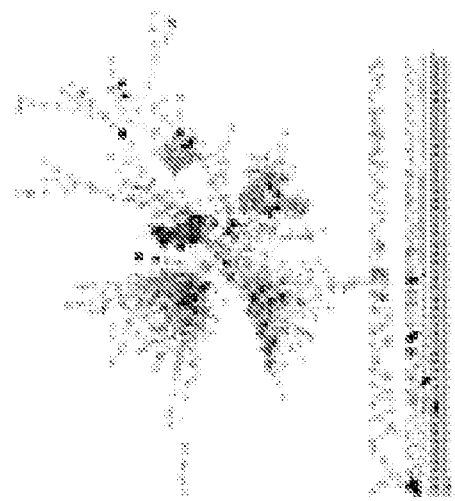
Figure 24:
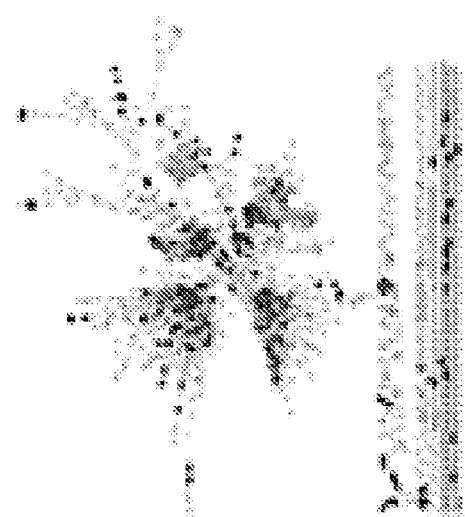
Figure 24:
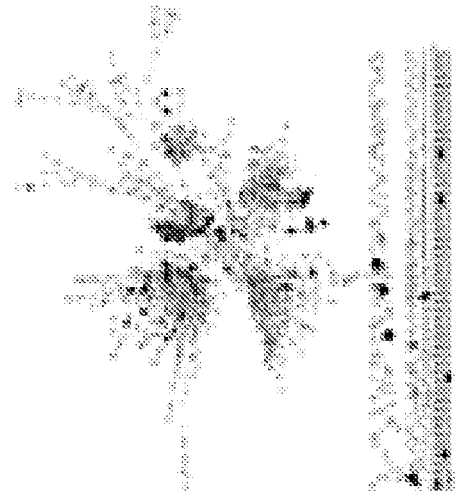
Figure 24:
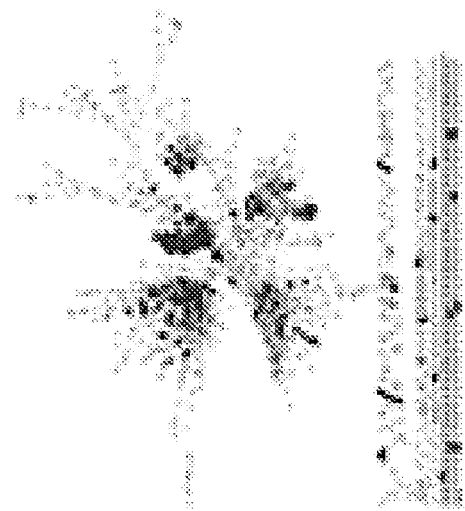
Figure 24:
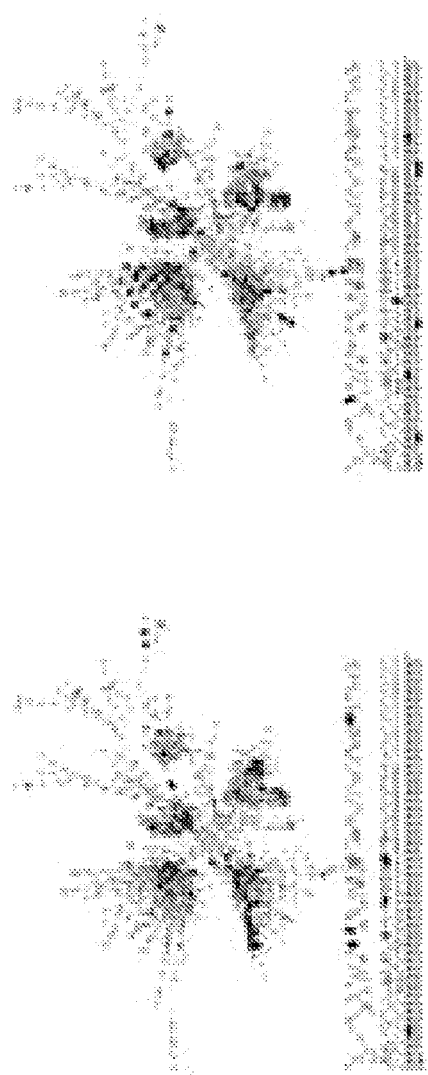
Figure 24:
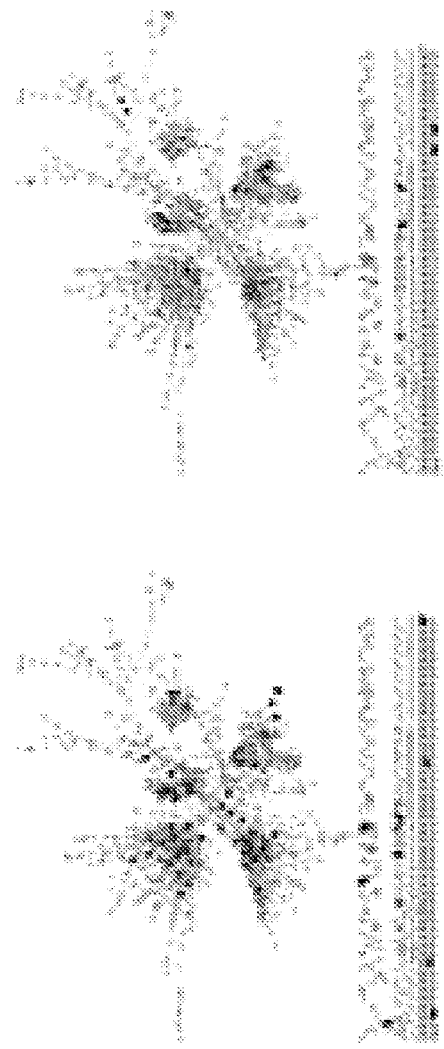
Figure 24:
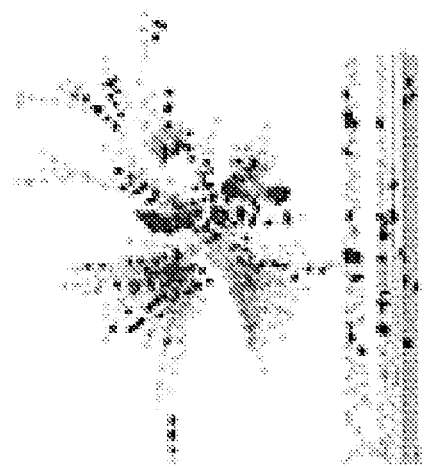
Figure 25:
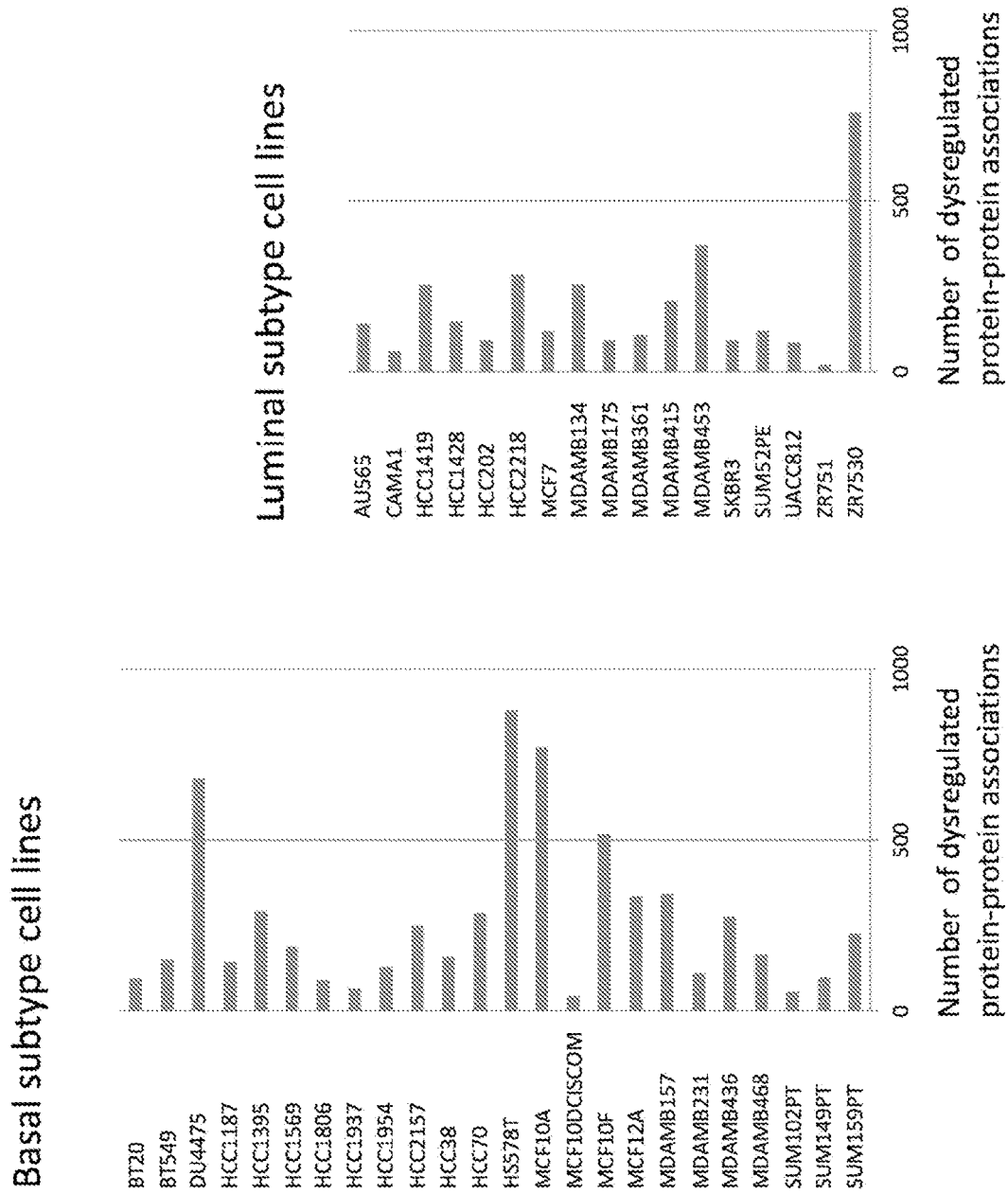
FIG. 25 is a histogram plot showing numbers of dysregulated protein-protein associations in basal and luminal subtype cancer cell lines.

The foregoing methods for identifying outliers can be applied to all globally identified protein-protein association across all cell lines. FIGS. 23 and 24 each show a set of plots for different cell lines, with outliers identified as enlarged dots on each plot. A wide range of dysregulated associations were identified across the cell lines ranging from 20 (0.1%) in ZR751 to 800 dysregulated associations (5.9%) in HS578T, affecting many different large complexes. FIG. 25 is a histogram plot summarizing dysregulated protein-protein associations for the basal and luminal subtype cell lines of FIGS. 23 and 24.

The methods disclosed herein for identifying deregulation between associated proteins in a basal protein-protein interaction network are powerful and capable of revealing deregulation events that are not detected using other analytical methods, as illustrated by FIGS. 22A and 22B. Basal networks are typically established by mapping proteomes of a relatively large number of samples (i.e., cell lines). Deviations among correlated relative concentrations of proteins can be identified for a large number of protein pairs, allowing for a global assessment of deregulation of protein-protein interactions across the entire network.

In addition to identifying deregulation between pairs of proteins in samples/cell lines used to establish the basal network, the proteomes of additional samples of interest can be measured, and changes in correlated relative concentrations of proteins in the samples of interest, relative to the previously established basal network relative concentrations, can be used to elucidate changes in deregulation over time. That is, associated proteins in certain samples that exhibit co-regulation initially (i.e., in the basal network) can be observed, in later acquired samples of interest, to exhibit interaction deregulation as a result of various mutations.

In *Drosophila*, for example, a basal network can be established through mapping proteomes of a set of *Drosophila* mutants showing high phenotypical and/or transcriptional diversity. Identifying protein-protein interaction deregulations in samples corresponding to different aging states can provide important information about which mutations in *Drosophila* are specifically linked to aging.

In human studies, similar approaches can be taken to identifying specific age-related mutations. Basal networks constructed based on samples corresponding to cancer cell lines or fibroblast cultures taken from skin biopsies of young donors can be used to identify changes in protein interaction deregulation among samples from donors (e.g., fibroblasts from skin biopsies) in varying aging states.

Figure 33A:
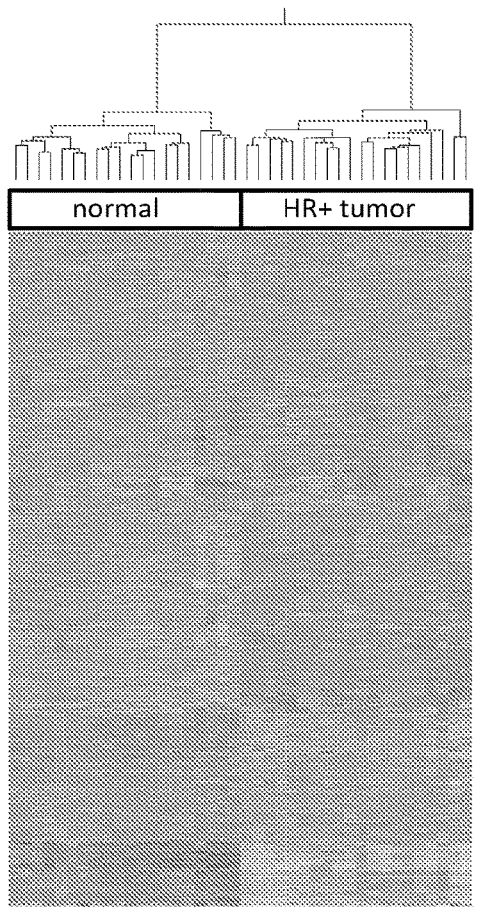
FIG. 33A is a plot showing clustering of the proteomes of 20 luminal-subtype primary breast tumor tissue samples and 20 normal breast tissue samples.

Protein-protein interaction dysregulation can also be identified and mapped in primary tissue samples using the methods and systems disclosed herein. To demonstrate the effectiveness of the methods in this context, tissue samples from 20 luminal-subtype breast tumors and 20 normal breast tissues were obtained and analyzed. FIG. 33A is a plot showing the proteomes of each of the tissue samples, determined quantitatively according to the multiplexed proteomics methods described above. Unsupervised, hierarchical clustering analysis segregated the proteome data into normal and tumor tissue subgroups.

Figure 33B:
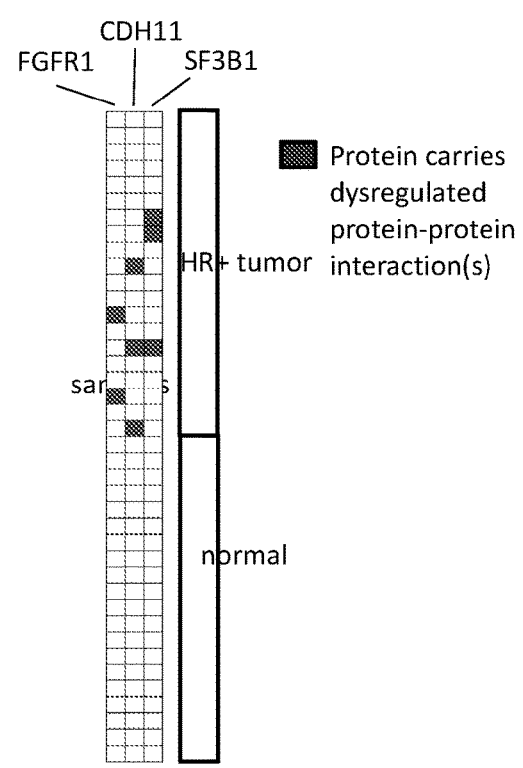
FIG. 33B is a plot showing dysregulated protein-protein interactions in the breast tumor and normal tissue samples of FIG. 33A.

Next, the proteomes of each sample were analyzed to identify dysregulation among protein-protein interactions. FIG. 33B shows a plot of identified dysregulations. Three proteins, FGFR1, CDH11, and SF3B1, known to often carry mutations (driver mutations) in luminal-subtype breast cancer, were found to carry dysregulated protein-protein interactions in some tumor samples, but not in any of the normal tissue samples. Without wishing to be bound by theory, it is expected that proteins with cancer-driving mutations may represent cancer vulnerabilities that can be addressed with therapeutic agents that target the vulnerabilities. The data in FIGS. 33A and 33B shows that methods disclosed herein for mapping protein-protein interaction dysregulation can also be applied to the identification of cancer vulnerabilities in primary tumor samples.

Drug Candidate Screening and Predictive Assessment

The methods disclosed herein for identifying protein-protein dysregulation in proteome networks can be used to predict the potential efficacy of candidate drugs for treating a variety of different diseases. In particular, cell lines representing various cancers (such as breast cancer) can be examined for dysregulation events. Significantly, such events have been discovered to be correlated with vulnerabilities in the cell lines which can be targeted by particular candidate drugs. Accordingly, by identifying protein-protein dysregulations, the potential efficacy of various candidate drugs can be assessed.

To evaluate the functional consequences of dysregulated protein-protein associations, data from a genome-wide shRNA-based drop-out screen on breast cancer cell lines was used. The data was obtained from Marcotte et al., "Functional Genomic Landscape of Human Breast Cancer Drivers, Vulnerabilities, and Resistance," *Cell* 164: 293-309 (2016), the entire contents of which are incorporated herein by reference. A total of 26 cancer cell lines were analyzed, for which both whole genome sequencing data and drop-out screen data were available. Genes defined by Marcotte et al. as "general essential" (essential in all cell lines) were not considered when comparing proteins in dysregulated associations with protein dropout scores. Dropout scores used in the analysis were zGARP scores as described in Marcotte et al., "Essential gene profiles in breast, pancreatic, and ovarian cancer cells," *Cancer Discov.* 2: 172-189 (2012), the entire contents of which are incorporated herein by reference. Genes with a zGARP score smaller than −2 were defined as cell line specific fitness genes.

Figure 26:
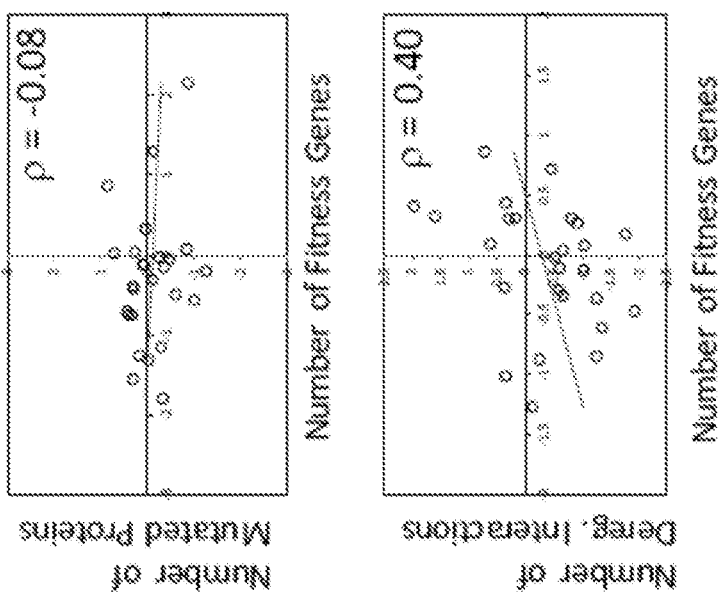
FIG. 26 is a set of plots showing correlations between the number of fitness genes and the number of mutated proteins and number of deregulation interactions across multiple cell lines.

A significant correlation was identified between the number of dysregulated protein-protein associations in each cell line and the number of proteins whose depletion affects the cell lines fitness (Spearman's coefficient $\rho=0.4$) suggesting that dysregulation of protein-protein associations results in higher level of susceptibilities. Notably, there was no correlation between the number of mutated proteins and the number of fitness genes ($\rho=-0.08$). Without wishing to be bound by theory, this absence of a correlation between the number of mutated proteins and the number of fitness genes may be at least partially attributable to the fact that only a limited number of mutations have functional consequences. FIG. 26 shows two plots, with the upper plot illustrating the correlation between the number of fitness genes for a particular cell line and the number of mutated proteins, and the lower plot illustrating the correlation between the number of fitness genes and the number of identified protein-protein dysregulation events for a particular cell line.

Figure 27:
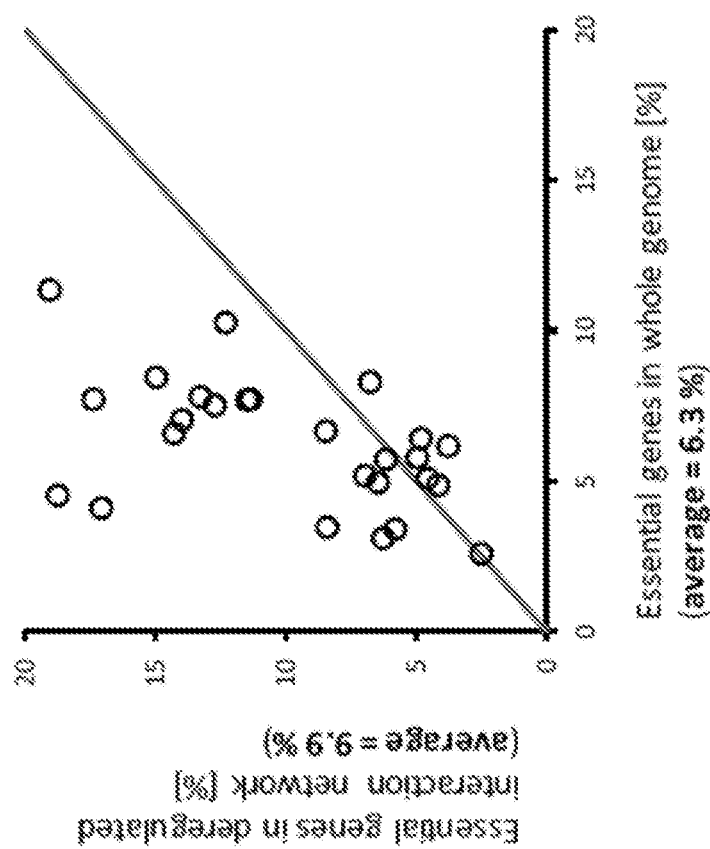
FIG. 27 is a plot showing the percentage of essential genes in a dysregulated interaction network against the percentage of essential genes in the whole genome for a set of cell lines.

It was also observed that in almost all cell lines, fitness gene products were enriched in the group of proteins with dysregulated protein-protein associations, compared to all 15309 genes monitored in the dropout screen. FIG. 27 is a plot showing the percentage of essential genes in the dysregulated interaction network, against the percentage of essential genes in the whole genome. Across the cell lines, the percentage of essential genes in the dysregulated interaction network averaged 9.9%, while the percentage of essential genes in the whole genome averaged 6.3%, so that the observed average enrichment in fitness proteins was 64%. These results show that high-throughput mapping of dysregulated protein-protein associations in cancer cell lines can reveal vulnerabilities of cancer cell lines with high efficiency.

Figure 28:
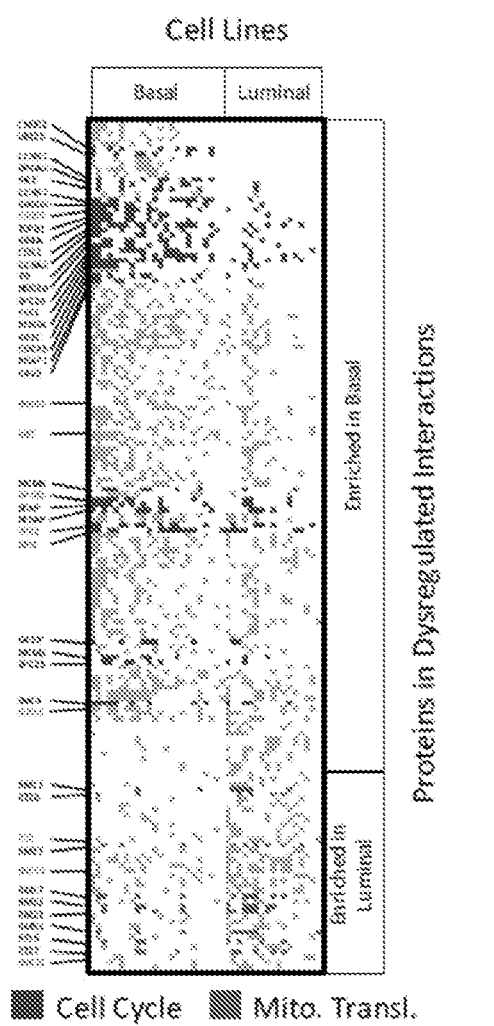
FIG. 28 is a plot showing basal and luminal subtype cancer cell lines, and dysregulated proteins identified in each subtype.

To assess potential efficacy of candidate drugs for treatment of the cancer cell lines, data from all 41 cell lines was analyzed to identify differences in functional modules dysregulated in cancer cell lines of the basal and luminal subtypes. A total of 167 proteins with dysregulated associations in at least 25% of either luminal (n=17) or basal (n=24) cell lines was identified, with a significant difference between the two subtypes determined by hypergeometric testing (p≤0.1). FIG. 28 is a plot showing the basal and luminal subtype cell lines, and dysregulated proteins identified in each subtype.

The identified proteins contained ten known cancer genes: CASC5, ERBB3, EZH2, DPOE1, MET, TPX2, and SUZ12 with dysregulations enriched in basal subtype cell lines, and ERCC3, RS2, and SMCE1 with dysregulations mainly in the luminal cell lines. The DAVID Bioinformatics platform was used for Gene Ontology (GO) category analysis of the proteins enriched in the dysregulated protein-protein association network of basal (117 proteins) and luminal cell lines (49 proteins), considering only "biological process" categories enriched with a Benjamini-Hochberg corrected p-value of ≤0.1 and using all proteins in the network of associated proteins determined as background. An unpaired, unequal variance, two tailed t-test was used to identified drugs significantly differentially affecting cell lines with defects in either mitochondrial biology (corresponding to the GO term Mitochondrial Translation) or the cell cycle (GO term Cell Cycle).

For these tests cell lines were designated as normal or dysregulated using a threshold of number of dysregulated proteins leading to balanced number of cell lines in the two groups compared. The thresholds were more than one cell cycle protein and at least one mitochondrial translation protein per with dysregulated protein-protein associations per cell line. The analysis revealed that 31 cell cycle regulating proteins were affected to diverse extents mainly in the basal cell lines, and 9 mitochondrial ribosomal proteins showed dysregulated associations mainly in luminal cell lines.

To determine how affected cells respond to drugs, the response of the 41 cell lines to 195 drugs spanning a wide range of targets was evaluated. Cells were seeded in 384 well plates and grown in media at variable density to insure optimal proliferation during assays. Drugs were added to the cells the day after seeding for adherent cell lines and the day of seeding for suspension cell lines. A series of nine doses was used with 2-fold dilution steps for a total concentration range of 256 fold. For each drug the maximum concentration was chosen based on prior knowledge of activity on target and in cells or previous data. Viability was determined using CellTiter-Glo (available from Promega Corporation, Australia) after 3 days of drug exposure. All plates were submitted to stringent quality control with the coefficient of variation of replicate control wells (cells with no drug) within a plate <20% and a signal (control wells)/noise (blank wells; no cells) ratio >50. At least 2 biological replicates (different plating days) were acquired for each drug. Drugs were sourced from reputable commercial vendors and academic sources. Estimators of the response to drugs (IC10-IC90, as well as AUC: Area Under the dose response Curve) were obtained. For drug responses estimated by the average of the AUC values of biological replicates, drugs that decreased the viability of cell lines (positive log 2 AUC ratio) associated with dysregulated cell cycle or mitochondrial function were sorted based on their Z-value transformed log 2 t-test p-values. Drugs with a Z-value greater than 2 were selected as strongly affecting the survival of dysregulated cell lines.

Figure 29:
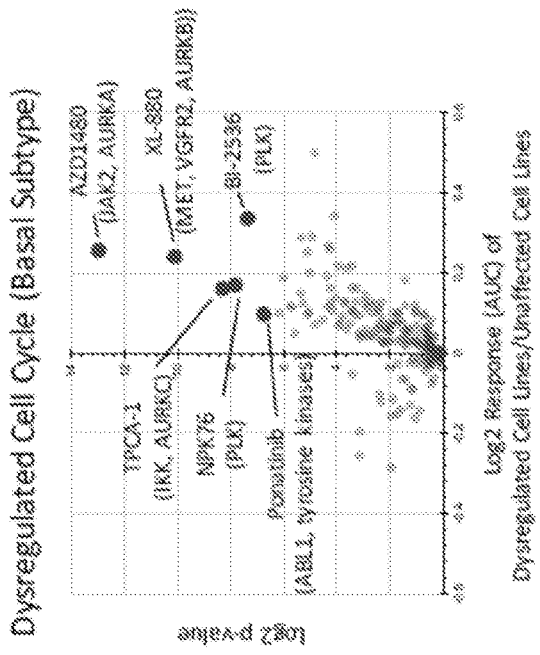
FIG. 29 is a plot showing log 2 p-values plotted against log 2 AUC response values for basal subtype cell lines.
Figure 30:
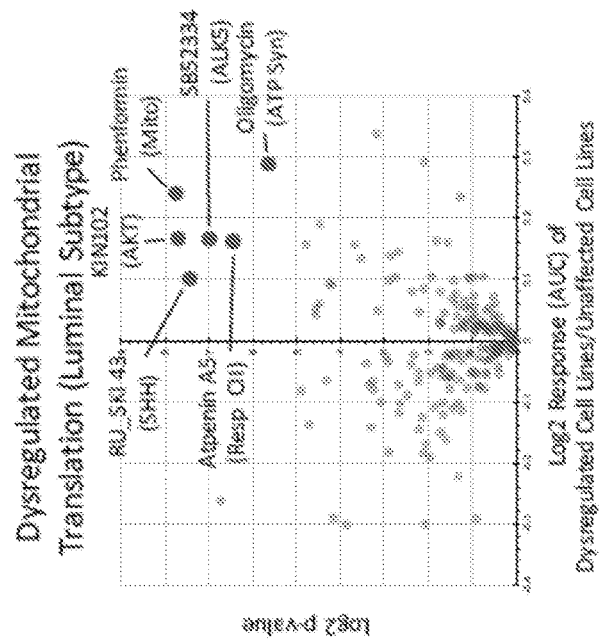
FIG. 30 is a plot showing log 2 p-values plotted against log 2 AUC response values for luminal subtype cell lines.

According to the foregoing methods, six drugs were identified that produced a significantly higher response in cell lines with a dysregulated cell cycle (≥2 cell cycle proteins with disturbed associations) when compared to unaffected cell lines (z-value ≥2 considering all p-values of drugs with higher response in affected cell lines). FIG. 29 is a plot showing log 2 p-values plotted against log 2 AUC response values for basal subtype cell lines, and FIG. 30 is a plot showing log 2 p-values plotted against log 2 AUC response values for luminal subtype cell lines.

The identified drugs included two inhibitors—NPK76 ($\rho=4\times10^{-3}$) and BI-2536 ($\rho=6\times10^{-3}$)—of polo-like kinases known as important cell cycle regulators. Another three drugs identified had nominal targets that are not directly linked to cell cycle: JAK2 (AZD1480, $\rho=1\times10^{-4}$), MET (XL-880, $\rho=1\times10^{-3}$), and IKK (TPCA-1, $\rho=3\times10^{-3}$). However, all three of these drugs have been shown to potently inhibit Aurora Kinases, and XL-880 (foretinib) also inhibits polo-like Kinase 4 (PLK4). Another identified therapeutic, ponatinib, targeted ABL1 but is known to inhibit a wide range of kinases. Dysregulated protein-protein associations encompassing MET enriched in basal cell lines were also identified.

Across 195 drugs tested, three of the significant six associations with a stronger response in cell lines with dysregulation of the mitochondrial ribosome protein complex were observed with phenformin ($p=5\times10^{-3}$) that blocks mitochondrial respiration through inhibition of complex I, atpenin A5 ($p=1.1\times10^{-2}$), a mitochondrial complex II inhibitor, and oligomycin ($p=2\times10^{-2}$), an inhibitor of ATP synthase. As above, a z-score of ≥2 was defined as a significance cutoff value, considering all p-values of drugs with higher response in the affected cell lines.

Taken together, these results demonstrate that predicted dysregulations of functional cellular modules based on deviation from global co-regulation networks is a reliable approach to identify cellular vulnerabilities and drug susceptibilities.

Figure 31:
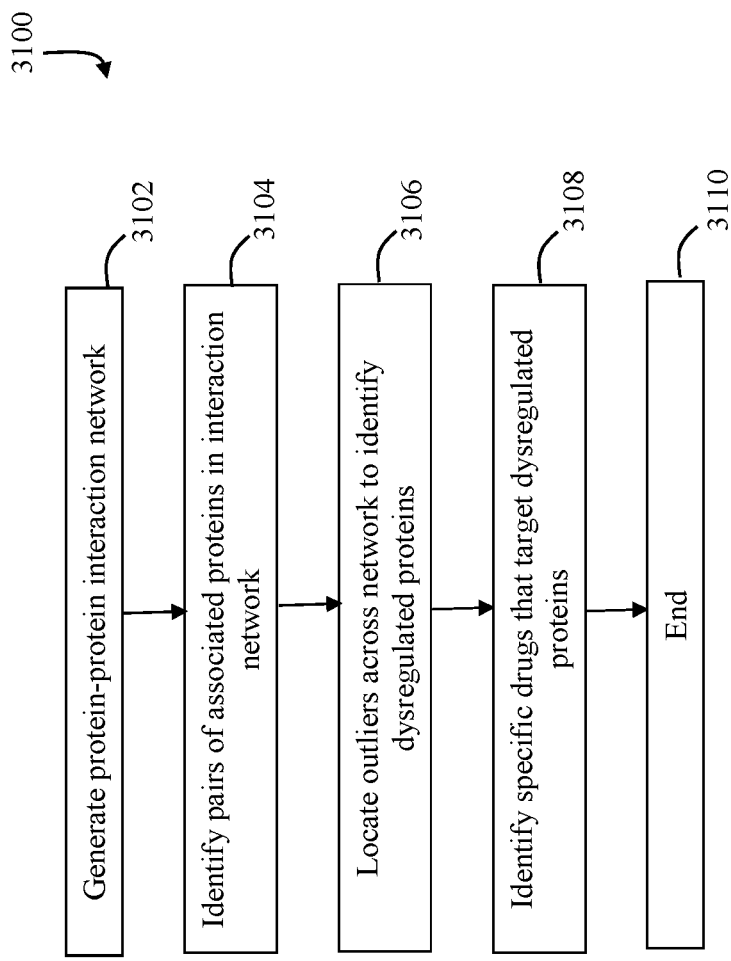
FIG. 31 is a flow chart showing a series of example steps that can be performed to predict the efficacy of drug candidates for treating particular diseases and/or cell lines.

FIG. 31 is a flow chart 3100 showing a series of steps that can be performed to predict the efficacy of drug candidates for treating particular diseases and/or cell lines. The steps shown in FIG. 31, in general terms, can be used to identify protein-protein interaction dysregulations in cell lines. Drug candidates that target the involved proteins, the complexes in which such proteins are involved, and pathways and/or functional modules in which such proteins are embedded, may show enhanced efficacy. As used herein, "functional modules" are a set of biological components (typically a combination of proteins and other cell components such as metabolites and/or genes and their interactions) that cooperate to accomplish, or are attributed to, a specific biological function.

In a first optional step 3102, a protein-protein interaction network is generated by identifying and quantifying proteins expressed across one or more samples (i.e., cell lines) using the methods disclosed above involving mass spectral analysis. This step is optional in that once a protein-protein interaction network is generated, the network can be re-used in subsequent iterations of the sequence of steps to evaluate other drug candidates. Accordingly, while in some embodiments the first step in flow chart 3100 is step 3102, in certain embodiments step 3104 is the first-executed step (i.e., the procedure begins with the protein-protein interaction network having already been determined).

In step 3104, pairs of associated, interacting (i.e., co-regulating) proteins are identified using methods discussed above, including for example comparing relative concentration levels of two pairs of proteins across all samples in the network to generate a correlation metric, such as the Spearman's correlation coefficient or the Pearson correlation coefficient. If the correlation metric exceeds a threshold value, the pair of proteins are deemed to be associated. As discussed previously, a variety of different methods can be used to identify pairs of interacting proteins, and the other steps of flow chart 3100 can implemented without regard to the manner in which protein-protein interactions are identified.

Then, in step 3106, outliers (e.g., correlated concentration outliers) are identified among the pairs of proteins evaluated to identify dysregulated proteins within the samples/cell lines. As discussed above, a variety of different methods can be used to identify correlated concentration outliers, including calculating various distance metrics from a line of best fit that establishes the correlated concentrations. A particular correlated concentration data point can be deemed an outlier if the closest distance from the point to the line of best fit exceeds a threshold value. Alternatively, a particular correlated concentration data point can be deemed an outlier of the distance (e.g., the Mahalanobis distance) from the data point to a centroid or other reference point for the distribution of data points exceeds a threshold value. It should be appreciated that other methods can also be used to identify correlated concentration outliers, including methods involving clustering analysis, nonlinear regression, principal components, and a variety of other techniques.

Next, in step 3108, specific drugs are identified from a set of candidate drugs based on information about the dysregulated protein-protein interactions identified in step 3106. As discussed above, drug efficacy has been observed to be correlated with protein-protein interaction dysregulation. More specifically, dysregulation of interactions between specific proteins within a sample or cell line suggests a vulnerability of the sample or cell line on the basis of the proteins. Specifically, vulnerabilities may be linked to the proteins carrying the dysregulated interactions, to complexes involving the proteins, and/or to pathways/functional modules in which the proteins are embedded.

Accordingly, specific drugs that target (i.e., inhibit) the proteins and/or their complexes, pathways, and functional modules are predicted to have greater efficacy. Thus, in step 3108, specific drug candidates are identified as likely to be effective if they target one or more aspects of the proteins carrying dysregulated protein-protein interactions. The identification can be based on information about one or more of: (a) proteins targeted by specific drug candidates; (b) protein complexes targeted by specific drug candidates; (c) biological pathways targeted by specific drug candidates; and (d) functional modules targeted by specific drug candidates. Specific drug candidates can be identified on the basis of any one or more of the foregoing types of information. In some embodiments, the identification of specific drug candidates in step 3108 can be performed by an electronic processor (e.g., processor 114 of controller 112) based on stored information corresponding to any one or more of the above types of information.

After the specific drugs have been identified, the procedure shown in FIG. 31 ends at step 3110.

The foregoing methods can be used to identify a wide variety of different types of vulnerabilities in cell lines on the basis of protein-protein interaction dysregulation. Observed dysregulations suggest that therapeutic agents that target the involved proteins and/or pathways, protein complexes, and functional modules in which such proteins are embedded may have enhanced efficacy for the cell lines in which such dysregulations occurs.

To demonstrate further the manner in which potential drug candidates can be identified, proteins with dysregulated protein-protein interactions in all of the 41 different breast cancer cell lines discussed above were identified, and then all 41 cell lines were screened against 195 different drug candidates. The drug candidates were screened at different concentrations, and the response to each drug candidate was measured as an area under the curve (AUC). Three known complexes—the BRCA1-associated genome surveillance complex, the centromere, and the proteasome—were selected from the CORUM database, and for each complex, the cell lines evaluated were separated into a first group in which cell lines carried dysregulated protein-protein interactions on any of the proteins in the complex, and a second group in which cell lines carried no dysregulations on any of the proteins in the complex.

Figure 32A:
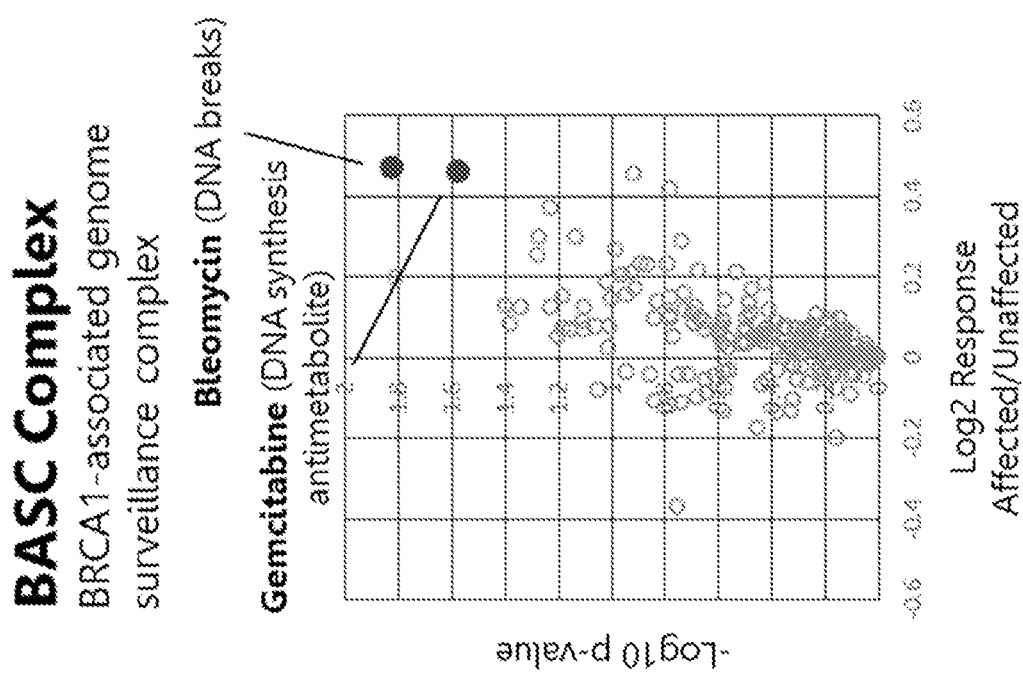
FIG. 32A is a plot showing how protein-protein interaction dysregulation in the BRCA1-associated genome surveillance complex for breast cancer cell lines affects responses of the cell lines to different drug candidates.
Figure 32B:
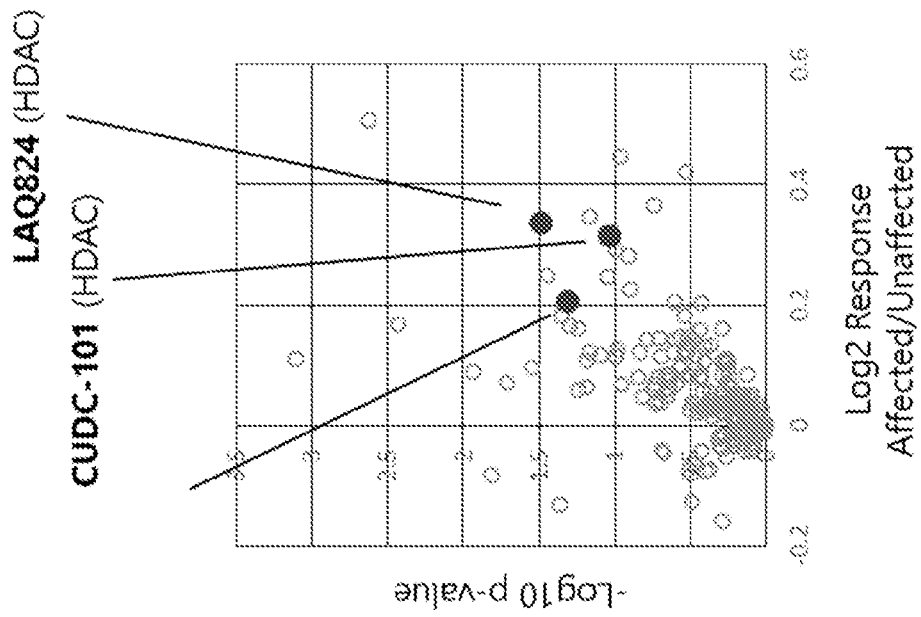
FIG. 32B is a plot showing how protein-protein interaction dysregulation in the centromere for breast cancer cell lines affects responses of the cell lines to different drug candidates.
Figure 32C:
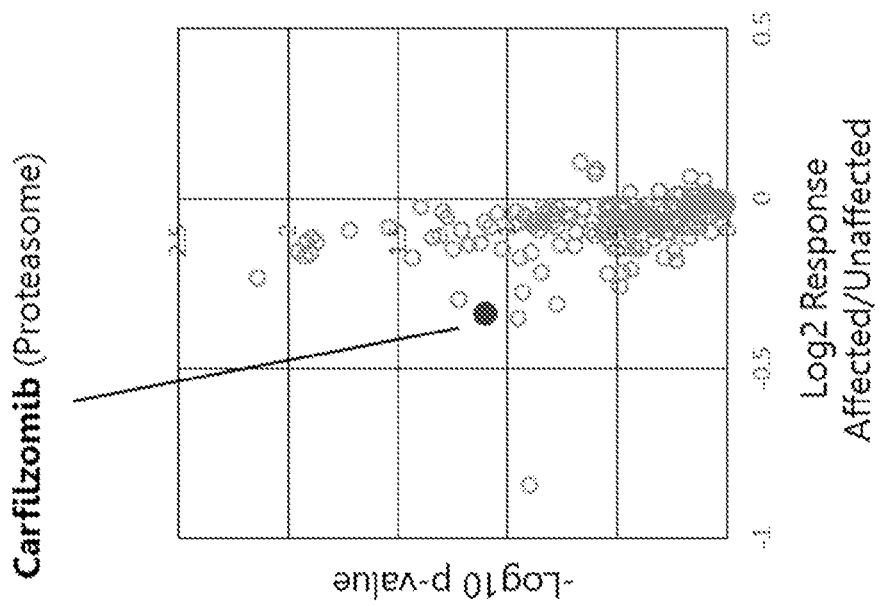
FIG. 32C is a plot showing how protein-protein interaction dysregulation in the proteasome for breast cancer cell lines affects responses of the cell lines to different drug candidates.

The results of this analysis are shown in FIGS. 32A-32C. Each figure is a plot showing how protein-protein interaction dysregulation in one of the selected complexes affects the responses of the evaluated breast cancer cell lines to different drug candidates. In each plot, every data point represents a different drug candidate. The horizontal axis in each plot represents the base 2 logarithm of the ratio of the drug candidate response in cell lines with dysregulation to the drug candidate response in cell lines without dysregulation. The vertical axis in each plot, which corresponds to the base 10 logarithm of the Grubbs test p-value, represents the significance of the drug candidate response difference.

The plot in FIG. 32A shows how protein-protein interaction dysregulation affects responses of the BRCA1-associated genome surveillance complex among the various evaluated cell lines to different drug candidates. Clustering of nearly all of the data points suggests that for most of the drug candidates involved, the observed effect was not significantly different. However, protein-protein interaction dysregulations in the genome surveillance complex were observed to sensitize the cell lines to the chemotherapeutics Bleomycin and Gemcitabine; these are represented by the outlier data points in FIG. 32A.

The plot in FIG. 32B shows how protein-protein interaction dysregulation affects responses of the centromere complex among the various evaluated cell lines to different drug candidates. Dysregulations were observed to sensitize the cell lines to MAC inhibitor drug candidates, including ACY-1215, CUDC-101, and LAQ824, which are represented by the outlier data points in FIG. 32B.

The plot in FIG. 32C shows how protein-protein interaction dysregulation affects responses of the proteasome complex among the various evaluated cell lines to different drug candidates. In particular, the proteasome complex was observed to be densensitized to treatment with a proteasome inhibitor (Carfilzomib). The data in FIG. 32C are, in a certain sense, opposite to the data shown in FIGS. 32A and 32B, in that the data of FIG. 32C are used to identify densensitization among cell lines to particular drug candidates rather than sensitization. Nonetheless, these data also show that dysregulation analysis of protein-protein interaction pathways effectively predicts responses to drug candidates that target the affected proteins, their complexes, and the pathways and functional modules in which they are embedded.

Hardware and Software Implementations

An electronic processor, such as processor 114 of controller 112 or another electronic processor (such as an electronic processor of a general purpose computer or another type of computing device), can be used to perform some or all of the steps of any of the methods disclosed herein. Controller 112, in addition to user interface 116 and display 118, can include a memory and a storage device.

Each of the components of controller 112 can be interconnected using a system bus. General purpose computers and other computing devices that implement the methods disclosed herein can also include memories, storage devices, user interfaces, and displays, and each of these components can be interconnected using a system bus. The electronic processor is capable of processing instructions stored in the memory or on the storage device to display graphical information—including any of the information disclosed herein, in the form of the figures shown herein and in other forms—on display 118.

The memory can be volatile or non-volatile, and can be a computer-readable medium. The storage device, also a computer-readable medium, may be a floppy disk device, a hard disk device, an optical disk device, a tape device, solid-state storage device, or another type of writeable medium. The processor and the memory can be supplemented by, or incorporated in, ASICs (application-specific integrated circuits).

Instructions executed by the electronic processor to perform any of the method steps disclosed herein can be implemented in digital electronic circuitry, or in computer hardware, firmware, or in combinations of these. Alternatively, or in addition, the instructions can be implemented in a computer program product tangibly embodied in an information carrier, e.g., in a machine-readable storage device, for execution by the processor. Suitable storage devices include, but are not limited to, persistent memory devices, storage media such as magnetic media (e.g., hard drives), optical media (e.g., CD-ROM, DVD) including both read-only and re-writeable media, flash memory devices (e.g., USB drives), and any other tangible storage medium suitable for storing instructions that can be read by a computer processor, electronic circuitry, and other devices that function to convert stored data suitable for execution by a computer processor, computing device, or electronic circuit.

The instructions, when executed by a processor such as electronic processor 114, cause the processor to perform the steps and functions disclosed herein. Software-based instructions can be written in any form of programming language, including compiled or interpreted languages, and can be deployed in any form, including as a stand-alone program or as a module, component, subroutine, or other unit suitable for use in a computing environment.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A method of identifying specific drug candidates for disease treatment, the method comprising:
   for pairs of associated expressed proteins in a protein-protein interaction network for a plurality of biological samples, comparing relative concentration values of the associated proteins in each of the biological samples to identify outliers among a distribution of the relative concentration values;
   identifying a set of proteins involved in dysregulated protein-protein interactions in the network based on the outliers; and
   predicting an efficacy of one or more drug candidates from among a set of drug candidates for treating a disease based on the identified set of proteins and information about one or more of proteins, protein complexes, biological pathways, and functional modules targeted by the set of drug candidates.

2. The method of claim 1, further comprising generating the protein-protein interaction network from the plurality of biological samples, wherein the network comprises a set of proteins expressed in the biological samples and concentrations of each member of the set of expressed proteins in each of the biological samples.

3. The method of claim 1, wherein predicting the efficacy of the one or more drug candidates comprises determining, for each drug candidate among the set of drug candidates, whether the drug candidate targets at least one of the proteins involved in dysregulated protein-protein interactions.

4. The method of claim 1, wherein predicting the efficacy of the one or more drug candidates comprises determining, for each drug candidate among the set of drug candidates, whether the drug candidate targets at least one protein complex in which at least one of the proteins involved in dysregulated protein-protein interactions is embedded.

5. The method of claim 1, wherein predicting the efficacy of the one or more drug candidates comprises determining, for each drug candidate among the set of drug candidates, whether the drug candidate targets at least one biological pathway involving at least one of the proteins involved in dysregulated protein-protein interactions.

6. The method of claim 1, wherein predicting the efficacy of the one or more drug candidates comprises determining, for each drug candidate among the set of drug candidates, whether the drug candidate targets at least one functional module involving at least one of the proteins involved in dysregulated protein-protein interactions.

7. The method of claim 1, wherein the plurality of biological samples comprises a set of cancer cell lines.

8. The method of claim 1, wherein the plurality of biological samples comprises a set of breast cancer cell lines.

9. The method of claim 1, wherein identifying the set of proteins involved in dysregulated protein-protein interactions comprises determining, for each protein, whether the protein is involved in dysregulated protein-protein interactions in all of the biological samples.

10. The method of claim 9, wherein the biological samples comprise basal and luminal cell lines, and wherein the set of proteins involved in dysregulated protein-protein interactions comprises proteins that are involved in dysregulated protein-protein interactions in only one of the basal and luminal cell lines.

11. The method of claim 2, wherein generating the protein-protein interaction network comprises identifying the proteins expressed in the biological samples and measuring the concentrations of each member of the set of expressed proteins by performing mass spectral analysis of each of the biological samples.

12. The method of claim 1, further comprising determining whether pairs of expressed proteins in the network are associated by:
calculating a Spearman's correlation coefficient for concentration distributions of each of the expressed proteins in the plurality of biological samples; and
determining whether pairs of expressed proteins are associated based on a value of the calculated Spearman's correlation coefficient.

13. The method of claim 12, further comprising identifying a pair of expressed proteins as associated if the value of the Spearman's correlation coefficient exceeds a threshold value.

14. The method of claim 1, further comprising determining whether pairs of expressed proteins in the network are associated by:
calculating a Pearson correlation coefficient for concentration distributions of each of the expressed proteins in the plurality of biological samples; and
determining whether pairs of expressed proteins are associated based on a value of the calculated Pearson correlation coefficient.

15. The method of claim 1, wherein comparing relative concentration values of the associated proteins in each of the biological samples to identify outliers among the distribution of the relative concentration values comprises identifying as outliers correlated relative concentration values that are positioned at greater than a threshold distance from a set of correlated relative concentration values that defines the distribution.

16. The method of claim 15, wherein the distribution comprises a reference relative concentration value that represents the distribution, and wherein the method comprises, for each member of the distribution of the relative concentration values:
determining a Mahalanobis distance between the correlated relative concentration value associated with the member and the reference relative concentration value; and
designating the member as an outlier if the distance exceeds a threshold distance value.

17. The method of claim 1, wherein comparing correlated relative concentration values of the associated proteins in each of the biological samples to identify outliers among the distribution of the relative concentration values comprises:
determining a line of best fit representing the distribution of the relative concentration values; and
for each member of the distribution of the relative concentration values:
calculating a shortest distance from the member to the line of best fit; and
designating the member as an outlier if the shortest distance associated with the member exceeds a threshold distance value.

18. The method of claim 16, wherein identifying the set of proteins involved in dysregulated protein-protein interactions in the network based on the outliers comprises, for each member of the distribution of the relative concentration values designated as an outlier, determining a sample from among the plurality of biological samples that is associated with the outlier.

19. The method of claim 11, wherein performing mass spectral analysis of each of the biological samples comprises:
ionizing peptides derived from the biological samples to generate peptide ions;
fragmenting a first portion of the peptide ions by collision-induced dissociation to generate a first population of peptide ion fragments;
fragmenting a second portion of the peptide ions by high-energy collision dissociation in an orbital trap to generate a second population of peptide ion fragments;
analyzing the first population of peptide ion fragments by trapping the first population of peptide ion fragments in a linear ion trap to identify a first population of peptides corresponding to the first population of peptide ion fragments;

analyzing the second population of peptide ion fragments in an orbital trap to identify a second population of peptides corresponding to the second population of peptide ion fragments; and identifying a set of proteins expressed in the biological sample based on the first and second populations of peptides.

20. A computer program product tangibly embodying a set of instructions that, when executed by a processor, causes the processor to identify specific drug candidates for disease treatment by:

for pairs of associated expressed proteins in a protein-protein interaction network for a plurality of biological samples, comparing relative concentration values of the associated proteins in each of the biological samples to identify outliers among a distribution of the relative concentration values;

identifying a set of proteins involved in dysregulated protein-protein interactions in the network based on the outliers; and predicting an efficacy of one or more drug candidates from among a set of drug candidates for treating a disease based on the identified set of proteins and information about one or more of proteins, protein complexes, biological pathways, and functional modules targeted by the set of drug candidates.

* * * * *